United States Patent
Idelevich et al.

(10) Patent No.: US 10,928,405 B2
(45) Date of Patent: *Feb. 23, 2021

(54) DEVICES AND METHODS FOR DETERMINING AND/OR ISOLATING CELLS SUCH AS CIRCULATING CANCER OR FETAL CELLS

(71) Applicant: Analiza, Inc., Bay Village, OH (US)

(72) Inventors: Pavel Idelevich, Hingham, MA (US); Arnon Chait, Bay Village, OH (US); Alan Bauer, Jerusalem (IL); Paul David Jackson, Foster City, CA (US)

(73) Assignee: Analiza, Inc., Bay Village, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/208,671

(22) Filed: Dec. 4, 2018

(65) Prior Publication Data

US 2019/0178901 A1 Jun. 13, 2019

Related U.S. Application Data

(63) Continuation of application No. 14/563,151, filed on Dec. 8, 2014, now abandoned, which is a continuation-in-part of application No. 14/312,875, filed on Jun. 24, 2014, now Pat. No. 9,063,127, which is a continuation of application No. 14/225,512, filed on Mar. 26, 2014, now Pat. No. 9,709,556, which is a continuation-in-part of application No. 14/103,170, filed on Dec. 11, 2013, now abandoned, said application No. 14/563,151 is a continuation-in-part of application No. 14/225,512.

(60) Provisional application No. 62/058,884, filed on Oct. 2, 2014.

(51) Int. Cl.
  *G01N 33/84* (2006.01)
  *G01N 33/569* (2006.01)
  *G01N 33/574* (2006.01)
  *G01N 33/50* (2006.01)
  *C12Q 1/6806* (2018.01)

(52) U.S. Cl.
  CPC .......... *G01N 33/84* (2013.01); *C12Q 1/6806* (2013.01); *G01N 33/5091* (2013.01); *G01N 33/56966* (2013.01); *G01N 33/57492* (2013.01); *G01N 2800/385* (2013.01)

(58) Field of Classification Search
  CPC ...................................................... G01N 33/84
  See application file for complete search history.

(56) References Cited

U.S. PATENT DOCUMENTS

| | | | |
|---|---|---|---|
| 5,547,849 A | 8/1996 | Baer et al. | |
| 6,793,642 B2 | 9/2004 | Connelly et al. | |
| 7,507,395 B2 | 3/2009 | Diwu et al. | |
| 7,855,078 B2 | 12/2010 | Evans | |
| 8,062,609 B2 | 11/2011 | Krager et al. | |
| 8,097,404 B2 | 1/2012 | Ribault et al. | |
| 8,548,219 B2 | 10/2013 | Ortyn et al. | |
| 8,551,425 B2 | 10/2013 | Goldkorn et al. | |
| 8,834,794 B2 | 9/2014 | Yazdanpanah et al. | |
| 9,063,127 B1 | 6/2015 | Idelevich et al. | |
| 9,250,242 B2 | 2/2016 | Martin et al. | |
| 2003/0119206 A1 | 6/2003 | Shai | |
| 2005/0287547 A1 | 12/2005 | Seligman | |
| 2007/0015171 A1 | 1/2007 | Bianchi | |
| 2009/0061456 A1 | 3/2009 | Allard et al. | |
| 2011/0195413 A1 | 8/2011 | Lin | |
| 2013/0078667 A1 | 3/2013 | Goodman et al. | |
| 2013/0102021 A1 | 4/2013 | Beacham et al. | |
| 2013/0130226 A1 | 5/2013 | Lim et al. | |
| 2013/0266960 A1 | 10/2013 | Idelevich et al. | |
| 2014/0106388 A1 | 4/2014 | Bangert et al. | |
| 2014/0133733 A1 | 5/2014 | Grady et al. | |

(Continued)

FOREIGN PATENT DOCUMENTS

| CA | 2 654 782 | 1/2008 |
|---|---|---|
| CN | 101438143 | 5/2009 |

(Continued)

OTHER PUBLICATIONS

Zhu & Murthy "Stem Cell Separation Technologies" (2012) Current Opinions in Chemical Engineering, vol. (2)1: 3-7. (Year: 2012).*
Invitation to Pay Additional Fees from International Application No. PCT/US2014/069340 dated Feb. 23, 2015.
International Search Report and Written Opinion from International Application No. PCT/US2014/069340 dated Apr. 23, 2015.
International Preliminary Report on Patentability from International Application No. PCT/US2014/069340 dated Jun. 23, 2016.
Extended European Search Report for International Application No. EP 14870632.8 dated Apr. 18, 2017.

(Continued)

*Primary Examiner* — Teresa E Knight
(74) *Attorney, Agent, or Firm* — Wolf, Greenfield & Sacks, P.C.

(57) ABSTRACT

Some embodiments of the present invention generally relate to devices and methods for determining and/or isolating cells. For example, one aspect is generally directed to methods and devices for detecting, identifying, counting, and/or potentially sorting cells of interest in blood or other biological sample. In some embodiments, blood samples (or other biological fluids) may be treated with signaling entities, such as pH-sensitive entities, that change color or otherwise produce a signal in suitable internal environments. For example, certain cells, such as cancer or fetal cells, may have differences in intracellular pH compared to other cells, which can be detected using pH-sensitive entities. In certain embodiments, the cells may be sorted based on such signaling entities; for example, illumination of cells in a suitable machine for sorting cells (e.g., using fluorescent light) may allow determination of the cells, which may also be recovered or isolated for further manipulation in some cases.

19 Claims, 28 Drawing Sheets

(56) References Cited

U.S. PATENT DOCUMENTS

| | | | |
|---|---|---|---|
| 2015/0160196 A1 | 6/2015 | Idelevich et al. | |
| 2015/0160198 A1 | 6/2015 | Idelevich et al. | |
| 2015/0160246 A1 | 6/2015 | Idelevich et al. | |

FOREIGN PATENT DOCUMENTS

| | | | |
|---|---|---|---|
| CN | | 103866016 A | 6/2014 |
| EP | | 0 057 809 A2 | 1/1982 |
| EP | | 0 221 768 A2 | 10/1986 |
| EP | | 0 499 693 A1 | 11/1991 |
| EP | | 0 582 836 | 7/1993 |
| EP | | 2 064 290 | 9/2004 |
| EP | | 1 984 030 | 8/2007 |
| EP | | 1 597 353 | 8/2013 |
| WO | WO 1992/002632 A1 | | 2/1992 |
| WO | WO 1994/002646 A1 | | 2/1994 |
| WO | WO 1996/034604 A1 | | 11/1996 |
| WO | WO 2000/075237 A3 | | 12/2000 |
| WO | WO 2002/040703 A1 | | 5/2002 |
| WO | WO 2004/076643 A2 | | 9/2004 |
| WO | WO 2005/080944 A1 | | 9/2005 |
| WO | WO 2006/097051 A1 | | 9/2006 |
| WO | WO 2007/065438 A2 | | 6/2007 |
| WO | WO 2007/089911 A2 | | 8/2007 |
| WO | WO 2008/057437 A2 | | 5/2008 |
| WO | WO 2008/076524 A2 | | 6/2008 |
| WO | WO 2008/117195 A2 | | 10/2008 |
| WO | WO 2008/132755 A1 | | 11/2008 |
| WO | WO 2010/078872 A2 | | 7/2010 |
| WO | WO 2011/025976 A2 | | 3/2011 |
| WO | WO 2013/075100 A1 | | 5/2013 |
| WO | WO 2013/119924 A1 | | 8/2013 |
| WO | WO 2013/147114 A1 | | 10/2013 |
| WO | WO 2013/152059 A1 | | 10/2013 |
| WO | WO 2014/138183 A1 | | 9/2014 |
| WO | WO 2015/112999 A1 | | 7/2015 |

OTHER PUBLICATIONS

European Office Action for Application No. EP 14870632.8 dated Apr. 24, 2018.
Agarwal et al., "Commercial landscape of noninvasive prenatal testing in the United States," Prenatal Diagnosis, 2013 (May 17, 2013), 33:521-531.
Boquest et al., Isolation of stromal stem cells from human adipose tissue. Methods Mol Biol. 2006;325:35-46.
Cohen et al., Determination of intracellular pH and compartmentation using diffusion-weighted NMR spectroscopy with pH-sensitive indicators. Magn Reson Med. May 2004;51(5):900-3.
Gambino et al., Acidification of blood is superior to sodium fluoride alone as an inhibitor of glycolysis. Clin Chem. May 2009;55(5):1019-21. doi: 10.1373/clinchem.2008.121707. Epub Mar. 12, 2009.
Gao et al., Decreased intracellular pH induced by cariporide differentially contributes to human umbilical cord-derived mesenchymal stem cells differentiation. Cell Physiol Biochem. 2014;33(1):185-94. doi: 10.1159/000356661. Epub Jan. 24, 2014.
Garciandia et al., Enhanced Na(+)-H+ exchanger activity and NHE-1 mRNA expression in lymphocytes from patients with essential hypertension. Hypertension. Mar. 1995;25(3):356-64.
Gascoyne et al., Dieletrophoretic Separation of Cancer Cells from Blood. IEEE Trans Indus App. 1997;33(3):670-8.
Gulley et al., Genetic tests to evaluate prognosis and predict therapeutic response in acute myeloid leukemia. J Mol Diagn. Jan. 2010;12(1):3-16. doi: 10.2353/jmoldx.2010.090054. Epub Dec. 3, 2009. Review.
Han et al., Fluorescent indicators for intracellular pH. Chem Rev. May 12, 2010;110(5):2709-28. doi: 10.1021/cr900249z. Review.
Harguindey et al.,The role of pH dynamics and the Na+/H+ antiporter in the etiopathogenesis and treatment of cancer. Two faces of the same coin—one single nature. Biochim Biophys Acta. Sep. 25, 2005;1756(1):1-24. Review.
Li et al., Mesenchymal stem cells are injured by complement after their contact with serum. Blood. Oct. 25, 2012;120(17):3436-43. doi:10.1182/blood-2012-03-420612. Epub Sep. 10, 2012.
McNamara et al., Metabolomics: a valuable tool for stem cell monitoring in regenerative medicine. J R Soc Interface. Aug. 7, 2012;9(73):1713-24. doi: 10.1098/rsif.2012.0169. Epub May 23, 2012.
Murphy et al., Platelet storage at 22 degrees C: role of gas transport across plastic containers in maintenance of viability. Blood. Aug. 1975;46(2):209-18.
Nih Stem Cell Information, Stem Cells: Scientific Progress and Future Research Directions, Chapter 10. Assessing Human Stem Cell Safety. 2001. National Institute of Health.
Obokata et al., "Bidirectional development potential in reprogrammed cells with acquired pluripotency," Nature, Jan. 30, 2014, 505:676-687.
Obokata et al., "Stimulus-triggered fate conversion of somatic cells into pluripotency," Nature, Jan. 30, 2014, 505:641-658.
Ozkan et al., "A rapid method for measuring interacellular pH using BCECF-AM," 2002 (date and month unknown), BBA, 2002 (Aug. 15, 2002), 1572:143-148.
Plaks et al., "Circulating tumor cells," Science, 2013 (Sep. 2013), 341:1186-1188 [downloaded from www.sciencemag.org on Sep. 25, 2013].
ReisEberg et al., "Flow cytometry in biotechnology," Appl. Microbiol. Biotechnol, Jun. 23, 2001, 56:350-360.
Sitar et al., The use of non-physiological conditions to isolate fetal cells from maternal blood. Experimental Cell Research. Jan. 15, 2005. 302(2):153-161.
Van Erp et al., Ratiometric measurement of intracellular pH in cultured human keratinocytes using carboxy-SNARF-1 and flow cytometry. Cytometry. 1991;12(2):127-32.
Webb et a., Dysregulated pH: a perfect storm for cancer progression. Nat Rev Cancer. Aug. 11, 2011;11(9):671-7. doi: 10.1038/nrc3110.
Aguilar et al., Murine but not human mesenchymal stem cells generate osteosarcoma-like lesions in the lung. Stem Cells. Jun. 2007;25(6):1586-94. Epub Mar. 15, 2007.

\* cited by examiner

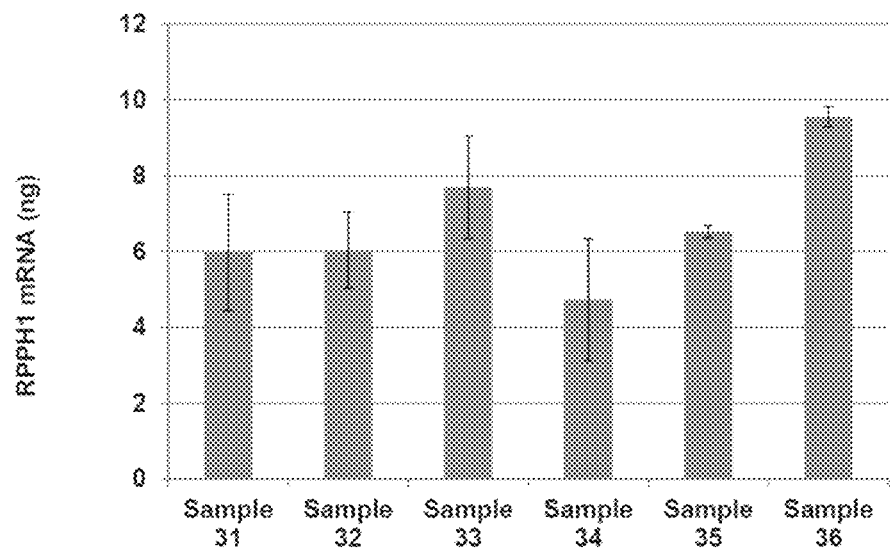

DEVICES AND METHODS FOR DETERMINING AND/OR ISOLATING CELLS SUCH AS CIRCULATING CANCER OR FETAL CELLS

RELATED APPLICATIONS

This application claims priority to all of the following according to the following recitation of priority relationships. This application is a continuation of U.S. patent application Ser. No. 14/563,151, filed Dec. 8, 2014, entitled "Devices and Methods for Determining and/or Isolating Cells Such as Circulating Cancer or Fetal Cells," which is a continuation-in-part of U.S. patent application Ser. No. 14/225,512, filed Mar. 26, 2014, entitled "Devices and Methods for Determining and/or Isolating Cells Such as Circulating Cancer or Fetal Cells," which is a continuation-in-part of U.S. patent application Ser. No. 14/103,170, filed Dec. 11, 2013, entitled "Devices and Methods for Determining and/or Isolating Cells Such as Circulating Cancer or Fetal Cells." Said Ser. No. 14/563,151 is also a continuation-in-part of U.S. patent application Ser. No. 14/312,875, filed Jun. 24, 2014, entitled "Devices and Methods for Determining and/or Isolating Cells Such as Circulating Cancer or Fetal Cells," which is a continuation of said Ser. No. 14/225,512. Ser. No. 14/563,151 also claims priority to U.S. Pat. Apl. Ser. No. 62/058,884, filed Oct. 2, 2014, entitled "Devices and Methods for Retaining Charged Molecules." Each of these is incorporated herein by reference in its entirety.

FIELD

The present invention generally relates to devices and methods for determining, treating, and/or isolating cells of interest, e.g., within a mixture of cells.

BACKGROUND

There are many systems or instances where the isolation of specific cells from a larger number or population of cells is highly desirable. For example, circulating tumor cells (CTC's) are cancer cells that have been displaced from their associated tumors and may enter the blood system or other parts of the vasculature. CTC's may offer information with respect to the condition and progress of a cancer; they may also serve to cause cancerous growths at other points within a body, e.g., at locations where there was no cancerous legion prior to the arrival and plastic growth of the CTC's. Circulating fetal cells (CFC's) are similar to CTC's in that they are often found in very low concentration in the blood; their obvious source is from a developing fetus in the mother's womb. CFC's may offer a rich potential for genetic analysis of a fetus at very early stages of fetal development. Stem cells are also of great potential therapeutic importance and the subject of specific detection and isolation.

Because of the importance of CTC's, stem cells, CFC's, and the like, their determination and/or isolation and use in genetic and medical analyses is extremely valuable. The major challenge with these cell groups is their low circulating numbers: there may be a few tens of such cells per milliliter of blood, as opposed to the millions of white blood cells and the like, and many millions of red blood cells.

SUMMARY

The present invention generally relates to devices and methods for determining, treating, and/or isolating cells of interest, e.g., within a mixture of cells. The subject matter of the present invention involves, in some cases, interrelated products, alternative solutions to a particular problem, and/or a plurality of different uses of one or more systems and/or articles.

In one aspect, the invention is generally directed to methods and devices for rapidly identifying and isolating predetermined cell species within a biological fluid containing a large number of non-target cells. In some embodiments, the invention includes a device for the detection and optionally sorting of circulating tumor or fetal cells, including: a biological fluid containing a plurality of cells; a pH-sensitive dye or other signaling molecule adapted to be internalized by at least some of the plurality of cells; and a machine capable of detecting and optionally sorting cells in response to a signal corresponding to predetermined pH within the cells. In one aspect of the device, the machine capable of detecting said signal and optionally counting cells is a cell cytometer. In another aspect of the device, the machine capable of detecting said signal and optionally sorting cells is a cell sorter.

In one aspect of the device, the circulating tumor cells are associated with at least one of the following cancers: lymphomas, sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, synovioma, mesothelioma, lymphangioendotheliosarcoma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, non-small cell lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia and heavy chain. In another aspect of the device, the pH-sensitive dye is adapted to give a predetermined color at basic pH values. In another aspect of the device, the detection step is followed by a cell sorting step. In another aspect of the device, the cell sorting machine is adapted to include a source of electromagnetic radiation. In another aspect of the device, the cell sorting machine is a fluorescent microscope. In another aspect of the device, the cell sorting machine is a fluorescent microscope with automated slide screening to identify and optionally isolate cells. In another aspect of the device, the electromagnetic radiation is selected from white light, laser light at a predetermined at least one wavelength, visible light at at least one predetermined wavelength, fluorescent light, x-ray radiation, or microwave radiation or a combination of different forms of electromagnetic radiation. In another aspect of the device, the cell sorting machine is adapted to communicate results to a computing device. In another aspect of the device, the computing device is realized as a mobile computing device, smartphone, cellular phone, tablet computer, laptop computer or tabletop computer. In another aspect of the device, the pH-sensitive dye is selected from the following: 2',7'-bis(2-carboxyethyl)-5(6)-carboxyfluorescein tetrakis(acetoxymethyl) ester (BCECF AM), 5(6)-carboxy-2',7'-dichlorofluorescein, 5(6)-carboxyfluorescein, 5(6)-carboxyfluorescein diacetate, 5(6)-carboxyfluorescein N-hydroxysuccinimide ester, 3,6-diacetoxyphthalonitrile, 6,8-dihydroxy-1,3-pyrenedisulfonic acid disodium salt, Eosin diacetate, or naphthofluorescein. In another aspect of the device, the pH-sensitive dye is realized as a plurality of pH-sensitive dyes. In another aspect of the device, one of more dyes that are conjugated to antibodies targeting specific cell antigens are also included. In another aspect of the device, the cell cytometer or sorter identifies and optionally sorts circulating cells in conjunction with a response from the pH-sensitive dye and at least one additional dye that is conjugated to an antibody targeting a specific cell antigen.

In certain embodiments, the invention includes a device comprising a fluid comprising target cells of interest and non-target cells, a pH-sensitive entity internalized within the cells, and a cell cytometer containing the fluid. In some cases, the pH-sensitive entity has a first state within the target cells of interest and a second state within the non-target cells. In another aspect, the invention includes a device comprising a fluid comprising cells, a pH-sensitive entity contained within at least some of the cells, and a cell cytometer containing the fluid. In another aspect, the invention includes a device for identifying a cell type. In some cases, the device includes a fluid comprising target cells and non-target cells, a pH-sensitive that is fluorescent at a pH equal to the intracellular pH of the target cells and is substantially less fluorescent at a pH equal to the intracellular pH of the non-target cells, and optionally, a cell cytometer containing the fluid. In some cases, said target cells have an intracellular pH higher than an intracellular pH of said non-target cells.

In another aspect, the invention includes a device comprising a fluid comprising cells, a pH-sensitive entity contained within at least some of the cells, and a cell cytometer containing the fluid. In another aspect, the invention includes a device for identifying a cell type. In some cases, the device includes a fluid comprising target cells and non-target cells, a pH-sensitive that is fluorescent at a pH equal to the intracellular pH of the target cells and is substantially less fluorescent at a pH equal to the intracellular pH of the non-target cells, and optionally, a cell cytometer containing the fluid. In some cases, said target cells have an intracellular pH higher than an intracellular pH of said non-target cells.

In another aspect, the present invention is generally directed to a device, e.g., a device for determining and/or isolating cells such as cancer cells or fetal cells. In one set of embodiments, for instance, the device comprises a fluid comprising cells, a pH-sensitive entity internalized within at least some of the cells, and a cell cytometer containing the fluid. The invention includes, in another set of embodiments, a method for specifically detecting, and optionally isolating circulating tumor cells including: providing a predetermined volume of a biological fluid, the fluid containing a plurality of cells; adding to the fluid a predetermined amount of a pH-sensitive dye adapted to give a predetermined response when exposed to a given form of electromagnetic radiation when the dye is present in an environment of a known pH range; allowing the plurality of cells in the fluid and the dye to incubate for a predetermined period of time to allow said dye to be internalized within the cells; placing a portion of the biological fluid in a machine capable of detecting and optionally sorting the cells based on detection of said predetermined response corresponding to a specific pH within the cells. In one aspect of the method, the step of detection and optionally sorting is conducted with a laser using a cell cytometer or optionally a cell sorter. In another aspect of the method, the number of cells detected per unit volume of the biological fluid is used to determine the stage of cancer, In yet another aspect of the method, the number of cells detected per unit volume of the biological fluid is used for early detection of cancer, or for monitoring disease progression, or for monitoring response to treatment, or to detect disease recurrence.

In one aspect of the method, there is an additional step of performing genetic, morphology or cytopathology analysis of the circulating tumor cells. In another aspect of the method, there is an additional step of identifying at least one form of cancer associated with the circulating tumor cells. In another aspect of the method, the count of the circulating tumor cells detected by the cell cytometer machine is used to assess a clinical condition. In another aspect of the method, the predetermined period of time is between 1 minute and two hours. In another aspect of the method, the biological fluid is selected from blood, blood serum, cerebral spinal fluid, urine, nipple aspirate, saliva, phlegm, pleural or abdominal exudate or transudate. In another aspect of the method, there is an additional step of incubating the biological fluid with a buffer a predetermined pH prior to the step of adding. In another aspect of the method, a plurality of incubations of the biological fluid are performed with a plurality of buffers, each with a different pH. In another aspect of the method, the cells are selected for further analysis from the groups of isolated cells corresponding to the plurality of buffers. In another aspect of the method, the electromagnetic radiation is selected from white light, laser light at a predetermined at least one wavelength, visible light at at least one predetermined wavelength, fluorescent light, x-ray radiation, microwave radiation or a combination of different forms of electromagnetic radiation. In another aspect of the method, one of more dyes that are conjugated to antibodies or magnetic nanoparticles coated with antibodies targeting specific cell antigens are also included. In another aspect of the method, the cell sorting step is conducted in response to the pH-sensitive dye and at least one additional dye that is conjugated to an antibody, or a magnetic nanoparticles coated with antibodies, targeting a specific cell antigen. In another aspect of the method, the at least one additional antibody that is conjugated to the at least one additional dye is specific to detect epithelial-specific markers or tumor-specific antigens present on the CTC surface: EpCAM, EphB4, HER2, EGFR, CEA, MUC-1, negative selection for CD45, or other antigens known in cancer cell biology. In another aspect of the method, a pre-fractionation step is included to remove predetermined cell fractions before incubating with the pH-sensitive dye. In another aspect of the method, the pre-fractionation step is designed to remove red blood cells by lysing.

The invention additionally includes, in yet another aspect, a method for specifically isolating circulating fetal cells including: providing a predetermined volume of a biological fluid, the fluid containing a plurality of cells; adding to the fluid a predetermined amount of a pH-sensitive dye adapted to give a predetermined response when exposed to a given form of electromagnetic radiation when the dye is present in an environment of a known pH range; allowing the plurality of cells in the fluid and the dye to incubate for a predetermined period of time to allow said dye to be internalized within the cells; placing a portion of the biological fluid in a machine capable of detecting and optionally sorting the cells based on detection of said predetermined response corresponding to a specific pH within the cells.

In one aspect of the method, the step of detection and optionally sorting is conducted with a laser using a cell cytometer or optionally a cell sorter.

In one aspect of the method, there is an additional step of performing kayrotyping, genetic or gene expression analysis or metabolic profiling on the circulating cells. In another aspect of the method, the biological fluid is blood or amniotic fluid. In another aspect of the method, the isolation of circulating fetal cells from blood could be performed as early as 5 or 6 weeks following gestation. In another aspect of the method, the circulating fetal cells isolated from maternal blood are associated with the fetus and not from persistent fetal cells that are related to a prior pregnancy. In another aspect of the method, a pre-fractionation step is included to remove predetermined cell fractions before incubating with the pH-sensitive dye. In another aspect of the method, the pre-fractionation step is designed to remove red blood cells by lysing. In another aspect of the method, the pH-sensitive dye is selected from the following: 2',7'-bis(2-carboxyethyl)-5(6)-carboxyfluorescein tetrakis(acetoxymethyl) ester (BCECF AM), 5(6)-carboxy-2',7'-dichlorofluorescein, 5(6)-carboxyfluorescein, 5(6)-carboxyfluorescein diacetate, 5(6)-carboxyfluorescein N-hydroxysuccinimide ester, 3,6-diacetoxyphthalonitrile, 6,8-dihydroxy-1,3-pyrenedisulfonic acid disodium salt, Eosin diacetate, naphthofluorescein. In another aspect of the method, the genetic analysis includes a search for genetic abnormalities. In another aspect of the method, the pH-sensitive dye is realized as a plurality of pH-sensitive dyes. In another aspect of the method, the pH-sensitive dye is adapted to give a predetermined fluorescent radiation at basic pH values. In another aspect of the method, the cell sorting machine is adapted to include a source of electromagnetic radiation. In another aspect of the method, the electromagnetic radiation is selected from white light, laser light at a predetermined at least one wavelength, visible light at at least one predetermined wavelength, fluorescent light, x-ray radiation, or microwave radiation or a combination of different forms of electromagnetic radiation. In another aspect of the method, one of more dyes that are conjugated to antibodies, or magnetic nanoparticles coated with antibodies, targeting specific cell antigens are also included. In another aspect of the method, the cell sorting step is conducted in response to the pH-sensitive dye and at least one additional dye that is conjugated to an antibody targeting a specific cell antigen. In another aspect of the method, the antibody is specific to CD4, CD8, CD45, CD71, anti-epsilon globin, and fetal hemoglobin. In another aspect of the method, further selection of fetal cells at early stage of pregnancy is performed using two additional antibody types, specific to CD4 and CD8, respectively, whereas cells missing both or having both antigens are further selected as fetal cells, and those displaying only one type of antigen CD4 or CD8 are recognized as maternal cells. In another aspect of the method, the cell sorting machine is adapted to communicate results to a computing device. In another aspect of the method, the computing device is realized as a mobile computing device, smartphone, cellular phone, tablet computer, laptop computer or tabletop computer. In another aspect of the method, the cells are selected for further analysis from the groups of isolated cells from a plurality of buffers. In another aspect of the method, there is an additional step of performing morphological analysis of the circulating fetal cells, after placing of sorted cells on the glass slide and staining by one of the conventional staining, for instance, Giemza stain, H&E stain, etc.

In another aspect, the present invention is generally directed to a method of determining cells of interest within a fluid. In one set of embodiments, the method comprises exposing a fluid containing cells to a pH-sensitive entity, determining the pH-sensitive entity within at least some of the cells within the fluid, and determining cells of interest based on the determination of the pH-sensitive entity within the cells.

In another aspect of the method, there is a step of immunostaining with organ-specific antibodies for investigation of localization of a tumor, or tissue origin of fetal cells. The invention includes, in another aspect, a method of determining target cells of interest within a fluid. In some embodiments, the method includes exposing a fluid containing target cells of interest and non-target cells to a pH-sensitive entity, determining the pH-sensitive entity internally within at least some of the cells within the fluid, and determining the target cells of interest based on the determination of the pH-sensitive entity within the cells. In some cases, the pH-sensitive entity has a first state within the target cells of interest and a second state within the non-target cells.

The invention includes, in another aspect, a method of determining target cells of interest within a fluid. In some embodiments, the method includes exposing a fluid containing target cells of interest and non-target cells to a pH-sensitive entity, determining the pH-sensitive entity internally within at least some of the cells within the fluid, and determining the target cells of interest based on the determination of the pH-sensitive entity within the cells. In some cases, the target cells of interest have an intracellular pH at least about 0.1 pH units higher than an intracellular pH of the non-target cells.

The invention includes, in another aspect, a method of determining cells of interest within a fluid. In some embodiments, the method includes exposing a fluid containing cells to a pH-sensitive entity, determining the pH-sensitive entity internally within at least some of the cells within the fluid, and determining cells of interest based on the determination of the pH-sensitive entity within the cells.

The invention includes, in another aspect, a method of determining cells of interest. In some embodiments, the method includes exposing a fluid containing target cells and non-target cells, wherein an intracellular pH of said target cells is at least about 0.1 pH units higher than an intracellular pH of said non-target cells, to a pH-sensitive entity able to fluoresce at or about said intracellular pH of said at least one target cell, determining said pH-sensitive entity in said at least one target cell, and determining cells of interest based on the determination of the pH-sensitive entity within said at least one target cell.

The invention includes, in another aspect, a method of determining cells of interest within a fluid. In some embodiments, the method includes exposing a fluid containing cells to a non-specific signaling entity, determining the non-specific signaling entity internally within at least some of the cells within the fluid, and determining cells of interest based on the determination of the non-specific signaling entity within the cells.

The invention includes, in yet another aspect, a method for isolating totipotent, pluripotent or multipotent stem cells, including: providing a biological fluid including stem cells and differentiated cells; exposing the fluid to a pH-sensitive entity, wherein the pH-sensitive entity has a first state within the stem cells of interest and a second state within the differentiated cells; detecting the pH-sensitive entity internally within the stem cells; and, isolating the stem cells with the pH sensitive entity displaying the first state. In one aspect of the method, the biological fluid is selected from blood, cerebral spinal fluid, urine, cervical fluid, nipple aspirate, saliva, phlegm, pleural or abdominal exudate or transudate. In another aspect of the method, the biological fluid is prepared from a homogenized tissue sample. In another aspect of the method, there is an additional step of characterizing the stem cells. In another aspect of the method, there is an additional step of freezing the stem cells for storage. In another aspect of the method, there is an additional step of transferring the stem cells to a growth medium adapted to preserve stem cell characteristics of the stem cells. In another aspect of the method, there is an additional step of concentrating the stem cells. In another aspect of the method, there is an additional step of storing the stem cells for future medical use. In another aspect of the method, the storing is performed with media formulated to encourage maintenance of stem cell pluripotentcy, such as TeSR-E8 medium from StemCell Technologies. In another aspect of the method, the storing includes cryopreservation of the stem cells. The invention also provides, in another aspect, a method for isolating totipotent or pluripotent embryonic or fetal stem cells, including: providing a biological fluid from a pregnant woman or fetus, wherein the fluid is adapted to include embryonic or fetal stem cells and differentiated maternal and/or fetal cells; exposing the fluid to a pH-sensitive entity, wherein the pH-sensitive entity has a first state within the embryonic or fetal stem cells of interest and a second state within the maternal and/or fetal cells; detecting the pH-sensitive entity internally within the embryonic or fetal stem cells; and, isolating the embryonic or fetal stem cells with the pH sensitive entity displaying the first state. In one aspect of the method, the pH-sensitive entity is selected from more of 2',7'-bis(2-carboxyethyl)-5 (6)-carboxyfluorescein tetrakis(acetoxymethyl) ester (BCECF AM), 5(6)-carboxy-2',7'-dichlorofluorescein, 5(6)-carboxyfluorescein, 5(6)-carboxyfluorescein diacetate, 5(6)-carboxyfluorescein N-hydroxysuccinimide ester, 3,6-diacetoxyphthalonitrile, 6,8-dihydroxy-1,3-pyrenedisulfonic acid disodium salt, Eosin diacetate, or naphthofluorescein. In another aspect of the method, there is an additional step of transferring the embryonic or fetal stem cells to a growth medium adapted to preserve stem cell characteristics of the stem cells. In another aspect of the method, there is an additional step of concentrating the embryonic or fetal stem cells. In another aspect of the method, there is an additional step of subdividing the isolated cells according to their expression of metabolic or cell surface markers characteristic of stem cell subtypes. In another aspect of the method, there is an additional step of storing the embryonic or fetal stem cells for future medical use. In another aspect of the method, the storing is performed with media formulated to encourage maintenance of stem cell pluripotentcy, such as TeSR-E8 medium from StemCell Technologies. In another aspect of the method, the storing includes cryopreservation of the embryonic or fetal stem cells. In another aspect of the method, the pH-sensitive entity is fluorescent within the embryonic or fetal stem cells and is substantially less fluorescent in the differentiated maternal and/or fetal cells. In another aspect of the method, the pH-sensitive entity is fluorescent within the differentiated maternal and/or fetal cells and is substantially less fluorescent in the embryonic or fetal stem cells. In another aspect of the method, the pH-sensitive entity is fluorescent at a pH of greater than about 7.2 and substantially less fluorescent at a pH of less than about 7. In another aspect of the method, there is an additional step of utilizing some of the embryonic or fetal stem cells for therapeutic use. The invention, in yet another aspect, also includes a device for isolating totipotent, pluripotent or multipotent stem cells, comprising: a fluid comprising target pluripotent stem cells of interest and non-target differentiated cells; a pH-sensitive entity adapted to be internalized within all cells in the fluid, wherein the pH-sensitive entity has a first state within the stem cells of and a second state within the non-target differentiated cells; and, a cell selector unit adapted to identify the first state of the pH-sensitive entity. In one aspect of the device, the cell selector is realized as a cell cytometer or microscope adapted to able to count cells. In another aspect of the device, the cell cytometer or microscope is adapted to isolate and/or sort cells. In another aspect of the device, the pluripotent stem cells are associated with a human organ. In another aspect of the device, the pluripotent stem cells are associated with a fetal source. In another aspect of the device, the fluid is selected from blood, blood serum, cerebral spinal fluid, urine, cervical fluid, nipple aspirate, saliva, phlegm, pleural or abdominal exudate or transudate.

In one aspect, the invention is generally directed to methods and devices for rapidly identifying and isolating predetermined cell species within a biological fluid containing a large number of non-target cells by virtue of a property associated with the predetermined cells. In other embodiments, the identified cells may be treated with a therapeutic agent.

In another aspect, the invention provides for a method for introducing a charged compound into an internal region of at least one target cell in a fluid, including: providing an uncharged compound adapted to be dissolved in a chemically polar solvent; dissolving the uncharged compound in a polar solvent; providing a fluid sample including at least one first target cell and at least one second non-target cell, wherein the at least one first target cell is adapted to convert the uncharged compound into a charged compound; adding the uncharged compound in the solvent to the fluid; incubating the uncharged compound with the fluid for a predetermined period of time; and, allowing the uncharged compound to be converted into the charged compound in the at least one first target cell, wherein the charged compound is adapted not to pass through a cellular membrane.

In one aspect of the method, the fluid is realized as blood, vaginal fluid, cervical fluid, blood serum, cerebral spinal fluid, urine, nipple aspirate, sputum, pleural or abdominal exudate or transudate, or amniotic fluid. In another aspect of the method, the predetermined period of time is half an hour, one hour, two hours, twenty-four hours. In another aspect of the method, the charged compound is realized as a plurality of charged compounds. In another aspect of the method, the uncharged compound is radioactive. In another aspect of the method, the uncharged compound is selected from 2',7'-bis (2-carboxyethyl)-5(6)-carboxyfluorescein tetrakis(acetoxymethyl) ester (BCECF AM), 5(6)-carboxy-2',7'-dichlorofluorescein, 5(6)-carboxyfluorescein, 5(6)-carboxyfluorescein diacetate, 5(6)-carboxyfluorescein N-hydroxysuccinimide ester, 3,6-diacetoxyphthalonitrile, 6,8-dihydroxy-1,3-pyrenedisulfonic acid disodium salt, Eosin diacetate, or naphthofluorescein. In another aspect of the method, the chemical property is realized as a basic pH value higher than 7.0, higher than 7.5, higher than 8.0. In another aspect of the method, the chemical property is realized as an enzyme or metallic catalyst. In another aspect of the method, the enzyme has an esterase property. In another aspect of the method, the enzyme has a protease property. In another aspect of the method, the solvent is water miscible. In another aspect of the method, the at least one first target cell is realized as a plurality of first target cells. In another aspect of the method, the first target cells are selected from circulating tumor cells, circulating fetal cells, or stem cells. In another aspect of the method, the stem cells are realized as fetal stem cells, cord blood stem cells, embryonic stem cells, adult stem cells, tissue-specific stem cells, and induced pluripotent stem cells. In another aspect of the method, the charged compound is adapted to have a detectable quality. In another aspect of the method, the detectable quality is selected from color, fluorescence, energy release, nuclear particle release, electromagnetic radiation release, chemical reactivity, biological reactivity, chemical polarity, or solubility. In another aspect of the method, the internal region is realized as a cytoplasm. In another aspect of the method, the internal region is realized as an organelle. In another aspect of the method, the organelle is realized as a mitochondrion. In another aspect of the method, the circulating tumor cells are derived from lymphomas, sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, synovioma, mesothelioma, lymphangioendotheliosarcoma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, non-small cell lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia. In another aspect of the method, the first target cell and the second non-target cell are human cells. In another aspect of the method, the first target cell and the second non-target cell are human cells. In another aspect of the method, the polar solvent is water. In another aspect of the method, the polar solvent is DMSO. In yet another set of embodiments, the invention includes a device for introducing a charged compound into an internal region of at least one target cell, including: a fluid containing first target cells and second non-target cells, wherein the first target cells include cytosols having a basic pH property and wherein the second non-target cells include cytosols having a neutral or acidic pH property; and, an uncharged compound adapted to freely pass into the cytosols of the first target cells and the second non-target cells, wherein the uncharged compound is adapted to be converted at a basic pH into at least one charged compound adapted to remain in the cytosols of the first target cells.

In one aspect of the device, the first target cells are selected from circulating tumor cells, circulating fetal cells, or stem cells. In another aspect of the device, the stem cells are realized as fetal stem cells, cord blood stem cells, embryonic stem cells, adult stem cells, tissue-specific stem cells, and induced pluripotent stem cells. In another aspect of the device, the at least one charged compound is adapted to have a detectable quality. In another aspect of the device, the detectable quality is selected from color, fluorescence, energy release, chemical reactivity, biological reactivity, chemical polarity, or solubility.

The invention, in yet another aspect, includes a method for delivering a therapeutic compound to a predetermined cell type in a mixed cell environment, including: providing a sample including at least one first target cell and at least one second non-target cell, wherein the at least one first target cell has a chemical property in cytoplasm not found in a cytoplasm of the second non-target cell; adding to the sample an uncharged compound adapted to pass through outer membranes and into internal regions of the at least one first target cell and the at least one second non-target cell, wherein the uncharged compound is therapeutically inactive; incubating the uncharged compound with the fluid for a predetermined period of time; and, allowing the chemical property of the first target cell to convert the uncharged compound into at least one charged compound adapted not to pass out of the cytoplasm of the at least one first target cell, wherein the charged compound has a therapeutic property.

In one aspect of the method, the therapeutic property is related to anti-cancer, anti-bacterial, or anti-inflammatory behavior. In another aspect of the method, the sample is a cancerous tumor. In another aspect of the method, the predetermined period of time is half an hour, one hour, two hours, twenty-four hours. In another aspect of the method, the at least one charged compound is realized as a plurality of charged compounds. In another aspect of the method, there is an additional step of dissolving the uncharged compound in a polar solvent prior to the step of adding. In another aspect of the method, the uncharged compound is radioactive. In another aspect of the method, the uncharged compound emits gamma rays, beta particles, and/or alpha particles. In another aspect of the method, the chemical property is realized as a basic pH value higher than 7.0, higher than 7.5, higher than 8.0. In another aspect of the method, the chemical property is realized as an enzyme or metallic catalyst. In another aspect of the method, the enzyme has an esterase or protease property. In another aspect of the method, the at least one first target cell is realized as a plurality of first target cells. In another aspect of the method, the tumor is associated with lymphomas, sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, synovioma, mesothelioma, lymphangioendotheliosarcoma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, non-small cell lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia.

The invention, in still another aspect, includes a method for delivering a signaling compound to a predetermined cell type in a mixed cell environment, including: providing a surgical sample including a plurality of first target cells and a plurality of second non-target cells, wherein the first target cells include a chemical property in cytoplasms not found in cytoplasms of the second non-target cells; adding to the sample an uncharged compound adapted to pass through outer membranes and into internal regions of the first target cells and the second non-target cells; incubating the uncharged compound with the fluid for a predetermined period of time; and, allowing the chemical property of the first target cells to convert the uncharged compound into at least one charged compound adapted not to pass out of the cytoplasm of the first target cells, wherein the charged compound has a therapeutic property.

In one aspect of the method, the uncharged compound is realized as BCECF AM. In another aspect of the method, the first target cells are located in a margin of a tumor. In another aspect of the method, the first target cells and second non-target cells are subjected to PET-CT. In another aspect of the method, there is a step of immunostaining with organ-specific antibodies for investigation of localization of a tumor. In another aspect of the method, there is a step of immunostaining with organ-specific antibodies for investigation of localization of a tumor. In another aspect of the method, the tumor is drug-resistant. In another aspect of the method, the tumor is multi drug-resistant.

In one aspect, the present invention is generally directed to a method of determining target cells of interest within a fluid. In one set of embodiments, the method comprises exposing a fluid containing target cells of interest and non-target cells to an unchanged compound, wherein the target cells of interest internally convert at least some of the uncharged compound into a charged compound; determining the charged compound within at least some of the cells within the fluid; and determining the target cells based on the determination of the charged compound within the cells.

The present invention, in another aspect, is generally directed to a device. The device, in certain embodiments, comprises a fluid comprising target cells of interest and non-target cells; a compound internalized within the cells, wherein the compound is charged within the target cells of interest and uncharged within the non-target cells; and a detector for determining the compound internalized within the cells.

According to still another aspect, the present invention is generally directed to a surgical method. In one set of embodiments, the method includes exposing a sample arising from a subject containing target cells of interest and non-target cells to an unchanged compound, wherein the target cells of interest internally convert at least some of the uncharged compound into a charged compound; determining the charged compound within at least some of the cells within the subject; and removing target cells of interest or non-target cells of interest from the subject based on the determination of the charged compound within the cells.

In another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 15A-15C illustrates determination of carcinoma cells, in accordance with certain embodiments of the invention;

FIGS. 16A-16C illustrate mRNA isolated from cells isolated from blood obtained from non-pregnant women with prior male pregnancies, in accordance with certain embodiments of the present invention;

DETAILED DESCRIPTION

Figure 1:
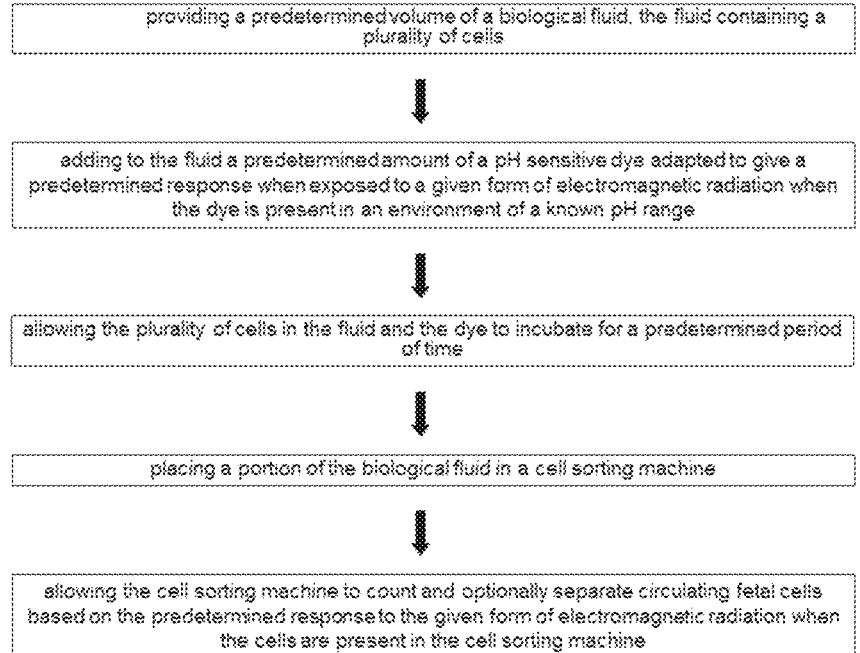
FIG. 1 shows a method according to one embodiment of the invention.

Some embodiments of the present invention generally relate to devices and methods for determining and/or isolating cells. For example, one aspect is generally directed to methods and devices for detecting, identifying, counting, and/or potentially sorting cells of interest in blood or other biological sample. In some embodiments, blood samples (or other biological fluids) may be treated with signaling entities, such as pH-sensitive entities, that change color or otherwise produce a signal in suitable internal environments. For example, certain cells, such as cancer or fetal cells, may have differences in intracellular pH compared to other cells, which can be detected using pH-sensitive entities. In certain embodiments, the cells may be sorted based on such signaling entities; for example, illumination of cells in a suitable machine for sorting cells (e.g., using fluorescent light) may allow determination of the cells, which may also be recovered or isolated for further manipulation in some cases.

For example, the present invention, in some embodiments thereof, relates to systems and devices for determining cells that may represent a very small proportion of cells in a fluid such as blood, in some cases quickly and facilely. Examples of such cells include, but are not limited to, circulating tumor or fetal cells. The present invention, in some embodiments, provides for isolation of such cells, e.g., for potential genetic or other investigation. Certain embodiments of the present invention could be employed for a wide variety of applications including, but not limited to, cancer screening, genetic testing, individualized medicine to include customization of therapy based on genetic or other features found in cells such as tumor cells, assessment of metastatic potential, recurrence monitoring, or other purposes. Other examples include, but are not limited to, pre-natal screening, genetic testing to assess potential medical conditions, or other purposes.

Some embodiments of the invention are generally directed to the determination of cells, such as tumor cells or fetal cells, within a larger number or population of cells. In some cases, less than about 1% of the population of cells may be the cells which are desired to be determined and/or isolated; in other cases, this may be less than about 0.1%, less than about 0.01%, less than about 0.001%, less than about $10^{-4}$%, less than about $10^{-5}$%, or less than about $10^{-6}$%. The cells may be suspended in blood, or another fluid (e.g., saline, cell media, amniotic fluid, etc.).

In some cases, the present invention generally relates to devices and methods for determining, treating, and/or isolating cells, e.g., within a mixture of cells. In some embodiments, the present invention is generally directed to devices and methods for allowing an uncharged molecule to enter a cell and be converted into a charged molecule, for instance, in cells of interest. The charged molecule, unlike its uncharged precursor, may be one that cannot pass back out through the cellular membrane, and thus may remain "trapped" within the cell. The charged molecule may be determinable, for example, via fluorescence, and/or the charged molecule may include therapeutic features such as radioactive ionization and/or enzyme inhibitory behavior. In some aspects, properties of target cells, such as high pH and/or unique enzymatic features, may allow for the specific conversion of uncharged molecule to charged molecules in cells of interest. Circulating tumor cells, stem cells, and circulating fetal cells are non-limiting examples of such cells.

For example, certain aspects of the present invention are generally directed to systems and methods for introducing an uncharged compound into a cell, and allowing the uncharged compound to become charged while in the cell. In some cases, the compound, once charged, is unable to readily exit the cell, and thus may remain lodged within the cell. The compound may be detectable (e.g., fluorescent or radioactive), and/or the compound may have desired effects on the cell (e.g., by treating the cell or killing the cell). In some cases, if a population of cells is present, some cells may be able to convert the uncharged compound into a charged compound, while other are unable (or less able) to do so. In this way, different types of cells may be distinguished, e.g., fetal cells and maternal cells, cancer cells and non-cancer cells, etc.

Figure 2:
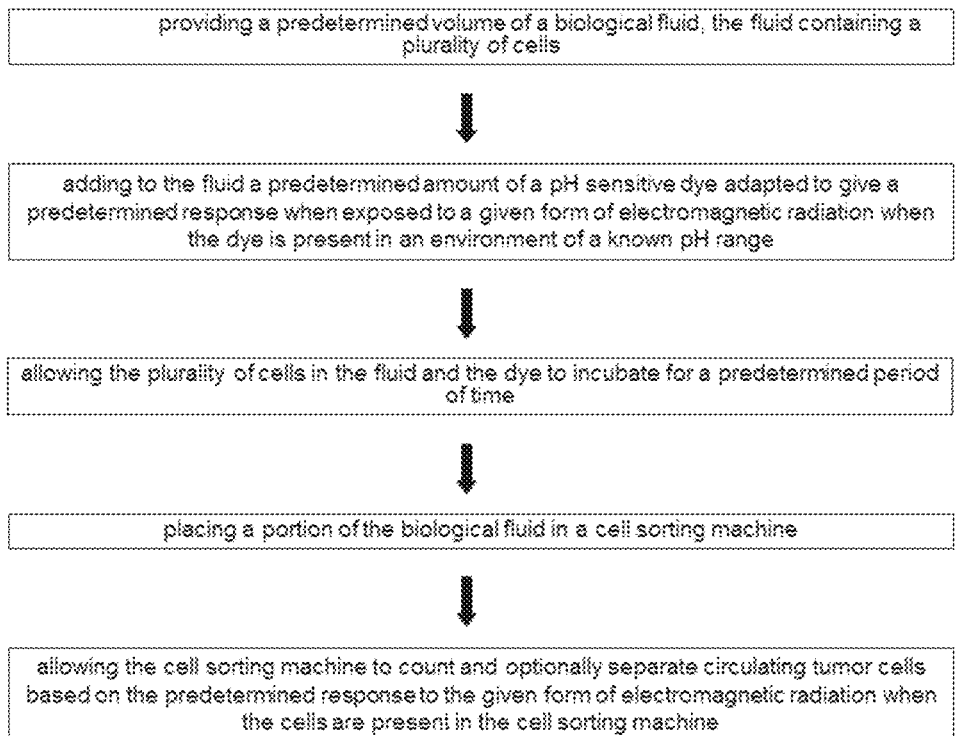
FIG. 2 shows a method according to another embodiment of the invention.

Non-limiting examples of methods according to various embodiments of the invention are shown in FIGS. 1 and 2. As another non-limiting example, FIGS. 3A-3D show schematic views of aspects of a device according to one set of embodiments. In this example, fluid sample 305 includes cells 310, where a plurality of said cells 310 are non-target cells 315 and a small percentage are target cells 320. For example, the target cells may be tumor cells, fetal cells, or other cells which are desired to be determined and/or isolated.

Figure 3A:
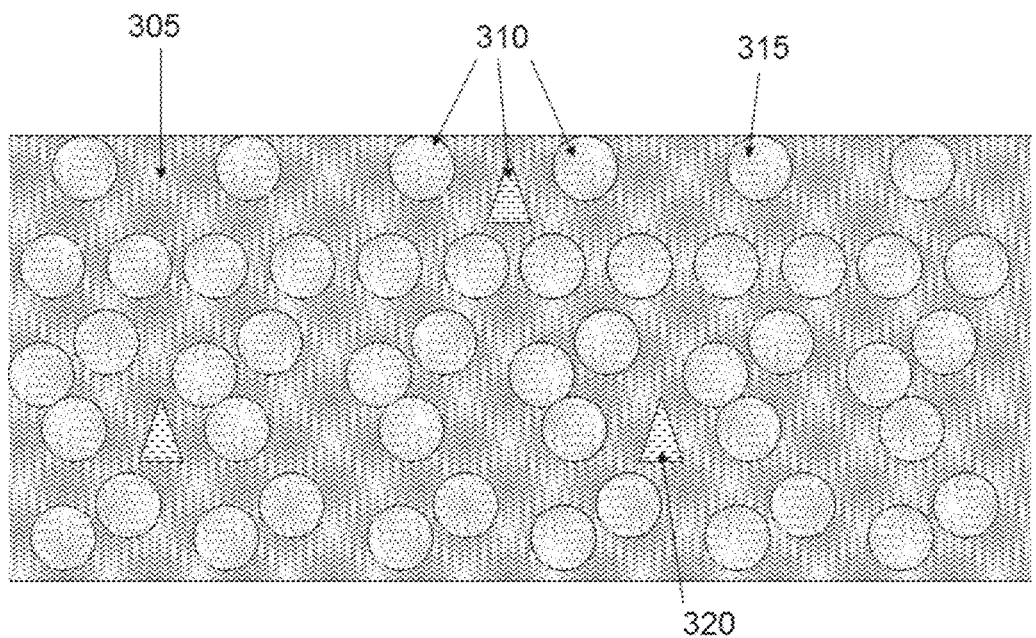
FIGS. 3A-3D shows a method according to yet another embodiment of the invention.
Figure 3B:
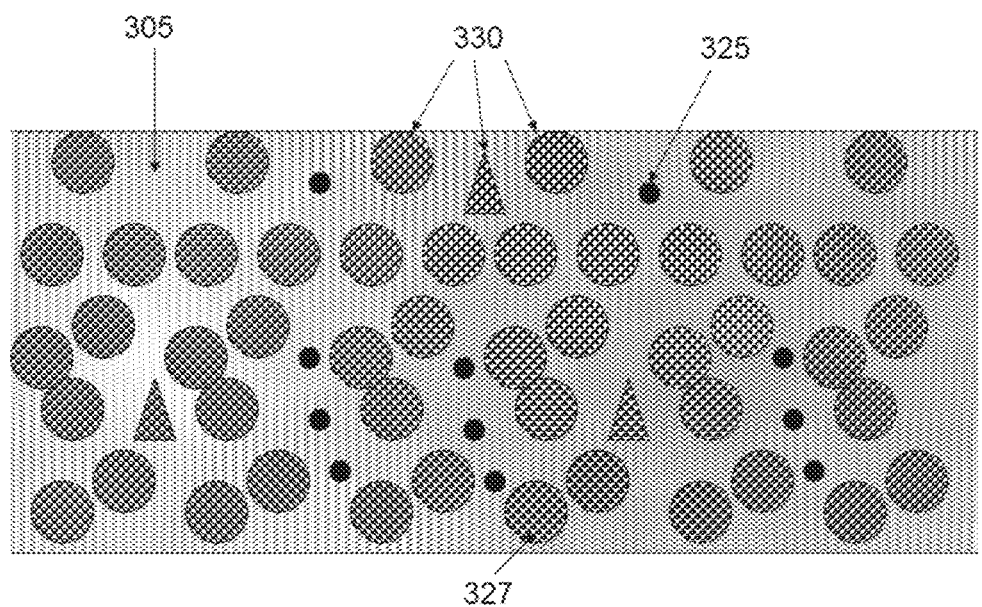

In FIG. 3B, pH-sensitive entity 325 is added to the fluid sample 305 and allowed to incubate with the fluid sample 305 for a predetermined period of time, e.g., between 1 minute and two hours. As shown in FIG. 3B, a portion of entity 325 enters cells due to the entity's ability to pass through cellular membranes. The cell-internalized pH-sensitive entity is shown as small black balls 327 in cells 330 containing the entity.

Figure 3C:
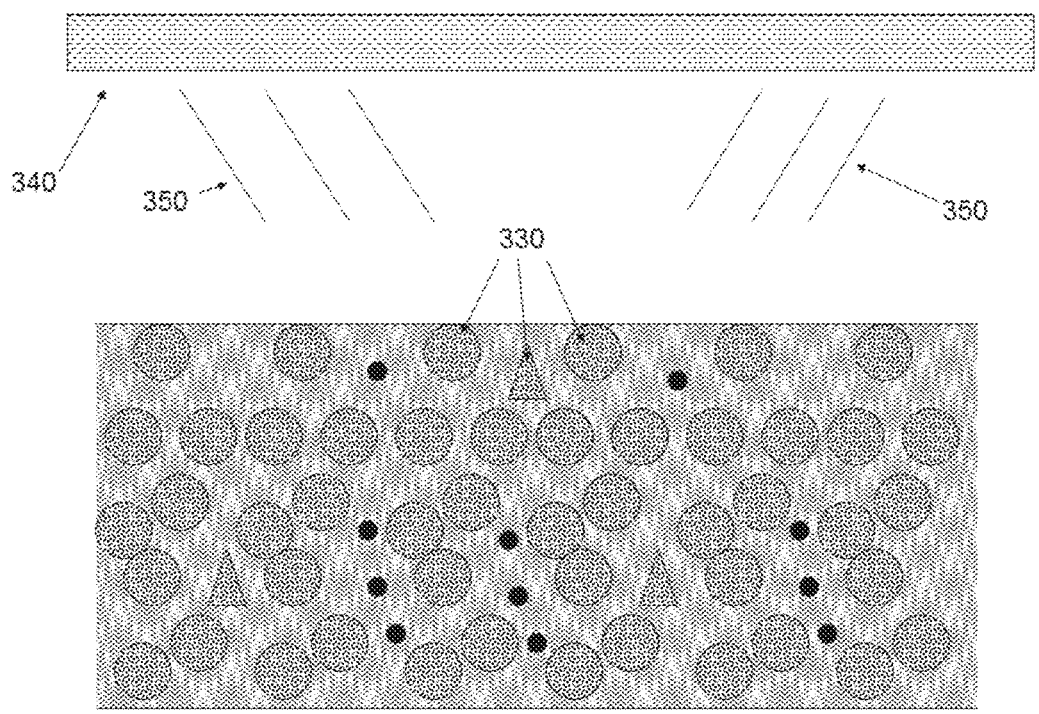
Figure 3D:
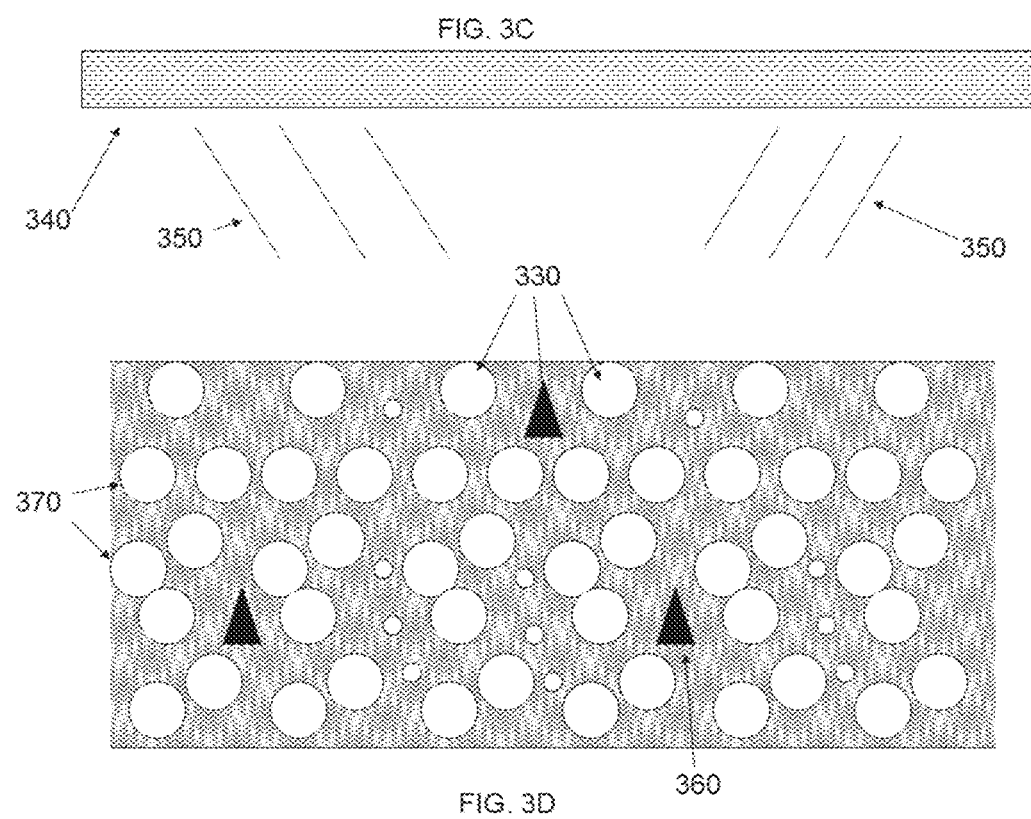

FIG. 3C shows entity-containing cells 330 in cell sorting machine 340 adapted to provide electromagnetic radiation 350 in the form of fluorescent light, in this particular example. FIG. 3D shows a view of the entity-containing cells 330 as seen after illumination with fluorescent light. Cells 360 show a predetermined color whereas the other cells 370 either show no color or show non-target color, for instance, based on the response of the entity to their intercellular pH levels. As a non-limiting example, cells 360 may fluoresce at a known wavelength when treated with a light of another, prescribed wavelength, whereas white blood cells and other cells found in the fluid sample 305 show other colors or no colors at all. Other examples are discussed herein. Determination of cells 360 allow for detection, identification, counting, sorting, and/or other manipulation of the cells, e.g., using suitable cell cytometers or the like. Subsequent analysis of the cells may include, but is not limited to, genetic analysis, morphology analysis, cytopathology analysis, or biochemical treatment.

In one set of embodiments, as discussed, a signaling molecule, or other signaling entity, is added to the fluid containing the cells or the cells are otherwise exposed to the signaling molecule or entity in some fashion. The signaling entity may be internalized by the cells, e.g., actively or passively. In some cases, once internalized, the signaling entity may change in some fashion in some of the cells (e.g., the cells of interest), while the signaling molecule may not change (or may change in a different way) in other cells. As a non-limiting example, the signaling entity may be pH-sensitive and/or may produce different "colors" or emissions at different pHs. The cells may then be determined and/or isolated using any suitable technique known in the art, based on the signaling entity, as discussed herein. For instance, in one set of embodiments, the cells may be separated using a flow cytometer or a cell sorter machine, such as a fluorescence-activated cell sorting (FACS) system. Thus, for example, cells having one intracellular pH (representing a first cell type, such as a tumor cell or a fetal cell) may be separated from cells having a different intracellular pH (representing cells of a second type, such as non-tumor or maternal cells).

Without wishing to be bound by any theory, it should be understood that certain cell types, such as cancer cells, stem cells, or fetal cells, may engage in metabolic behavior that significantly alters their internal cellular pH, e.g., to distinguish these cells from the majority of cells in a that are not tumor, stem or fetal cells, and/or there may be other changes that modify the polarity of their cytoplasm that can be determined or observed as changes in pH. It is believed that this is reflective of reactions and processes going on in such cells, and may thus provide information not reflected in other aspects of these cells, such as their relative size or relative abundance of certain cell membrane antigens. For example, in the case of circulating cancer cells, a change in intracellular pH may indicate the existence of specific functional attributes that may be useful for clinical applications, e.g., further indicating metastatic potential of the cells. For instance, in some cases, the intracellular pH of normal cells may be between about 6.8 and about 6.9, while the pH of the cancer cells may be higher than this; for instance, the pH of a cancer cell may be between 7.2 and about 7.4. In some cases, these pH changes may be significant, e.g., resulting in a change of at least about 0.1, at least about 0.2, at least about 0.3, at least about 0.4, at least about 0.5, at least about 0.7, at least about 1, at least about 1.2, at about 1.5, at least about 1.7, at least about 2, or more pH units, relative to normal intracellular pHs. In some cases, the pH changes may be significant. For example, there may be a change of at least about 0.5, at least about 1, at about 1.5, at least about 2, or more pH units, relative to normal intracellular pHs.

However, while some embodiments of the instant invention may be directed to the determination and/or isolation of cancer cells, tumor cells, fetal cells, etc., it should be understood that these are by way of example only, and that other cell types, e.g., exhibiting changes in pH due to enhanced metabolism, disease states, external conditions (e.g., toxins or poisons, concentration of CO or $CO_2$), or the like, may also be determined and/or isolated in other embodiments of the invention.

In addition, it should also be understood that fluids other than blood may be analyzed in other embodiments of the invention; for example, the cells may be present in other fluids such as blood, blood serum, vaginal fluid, cervical fluid, cerebral spinal fluid, urine, nipple aspirate, phlegm, sputum, pleural abdominal exudate or transudate, amniotic fluid, saline, cell media, water, or the like. In some cases, the fluid may be one that arises biologically, e.g., from an organism such as a human. The cells may be human and/or non-human cells. For example, in one embodiment, non-human cells present within blood (or other fluid) may be separated from human cells, e.g., on the basis of intracellular pH or other conditions.

If a signaling entity is present, the signaling entity may generally be a material that responds to electromagnetic radiation or other energy directed at it. In some cases, the signaling entity can specifically bind to an analyte; however, in other cases, the signaling entity can bind nonspecifically or otherwise interact with various analytes, or to other species (e.g., $H^+$ in the case of some pH-sensitive entities). The signaling entity may be a single type of molecule, or a plurality of different types of molecules in some cases. Color generation or fluorescence is one of a number of possible responses including, but not limited to, energy release, or chemical reactivity. Thus, a signaling entity, as used herein, is not limited to only color changes. It should also be understood that color generally refers to any response of the entity to treatment with electromagnetic radiation. Fluorescence, light, Raman, or other quantum-related phenomena are non-limiting examples of a response that may be referred to as a "color" change. Examples of suitable electromagnetic radiation include, but are not limited to, white light, laser light at a predetermined at least one wavelength, visible light at at least one wavelength, fluorescent light, X-ray radiation, microwave radiation, etc. or a combination of different forms of electromagnetic radiation, including but not limited to any combination of any of these. Those of ordinary skill in the art will be able to readily determine suitable electromagnetic radiation based on the signaling entity used.

In addition, it should be understood that in some cases, the fluid (e.g., blood) may undergo pre-treatment with chemicals, physical conditions, etc., for example, prior to or simultaneously with the addition of one or more signaling entities. For example, the fluid may be filtered, treated with an anticoagulant (e.g., citrate or heparin), acidified, centrifuged, or the like. As another example, the fluid may be exposed to one or more buffers. In some cases, the buffers may include buffers at different pH's.

In one set of embodiments, the signaling entity is pH-sensitive. pH sensitivity, as discussed herein, includes not only the usual definition of hydrogen ion activity in solution, but also a more extended description that includes solution polarity and the like, at least in some embodiments. The pH-sensitive entity may have at least a first color (or other determinable state) at a first pH and a second color (or other determinable state) at a second pH different from the first pH. The first pH and the second pH may be separated by at least about 0.5, at least about 1, at about 1.5, at least about 2, at least about 2.5, at least about 3, at least about 4, or at least about 5 pH units. In some cases, certain cells, such as some types of cancer cells or fetal cells, may exhibit differences in intracellular pH compared to other cells, which can be detected using pH-sensitive signaling entities.

In some cases, the signaling entity may be able to permeate cellular membranes or otherwise enter a cell, e.g., into the cytoplasm. In some cases, the signaling entity can diffuse passively across a cellular membrane; in other cases, however, the signaling entity enters a cell through active processes (e.g., via phagocytosis, pinocytosis, stimulation of cell-surface receptors, or the like). The signaling entity may also be able to adapt forms and color schemes that are reflective of the pH or solvent polarity environments associated with the inner regions of such cells, and in some cases, in response to modifying molecules that may be present in such regions (e.g., enzymes). The signaling entity may be biocompatible in some fashion, although in certain cases, the signaling entity need not be biocompatible; for example, exposure of the cells to the signaling entity may injure or kill the cells, although determination of the signaling entity may still occur.

The signaling entity may be excited in some fashion, e.g., using suitable electromagnetic energy, to allow for the identification or determination of such cells, e.g., due to the unique pH-associated color found in those cells. For example, the signaling entity may exhibit fluorescence, phosphorescence, a change in absorption (e.g., at particular wavelengths), or the like. Examples of suitable electromagnetic energy include, but are not limited to, white light, laser light at a predetermined at least one wavelength, visible light at at least one wavelength, fluorescent light, X-ray radiation, microwave radiation, etc. or a combination of any of these and/or other types of electromagnetic energy.

The following are non-limiting examples of pH-sensitive entities that may be used in various embodiments: 2',7'-bis (2-carboxyethyl)-5(6)-carboxyfluorescein tetrakis(acetoxymethyl) ester (BCECF AM), 5(6)-carboxy-2',7'-dichlorofluorescein, 5(6)-carboxyfluorescein, 5(6)-carboxyfluorescein diacetate, 5(6)-carboxyfluorescein N-hydroxysuccinimide ester, 3,6-diacetoxyphthalonitrile, 6,8-dihydroxy-1,3-pyrenedisulfonic acid disodium salt, Eosin diacetate, or naphthofluorescein. Other pH-sensitive entities may also be used in some cases. In some embodiments, the pH-sensitive entity may be one whose color profile at various pH value changes, and which has some ability to enter a cell, e.g., passively or through diffusion. In some cases, the pH-sensitive entity may be one that fluoresces after undergoing chemical modification via intracellular enzymes. Many such pH-sensitive entities can be obtained commercially. However, it should be understood that the pH-sensitive entities can also include not only pH dyes per se, but also other entities that show color changes or other discriminatory behavior relative to pH or the like.

In one set of embodiments, a signaling entity (e.g., one that is pH-sensitive) may be used to distinguish a target cell of interest (e.g., a cancer cell or a fetal cell, etc.) from other surrounding cells that are not of interest (e.g., respectively, normal cells or maternal cells, or even fetal cells associated with prior pregnancy, etc.). Other examples are discussed herein. In some cases, for example, the signaling entity may have a first state in a first type of cell (e.g., the target cell) and a second state in a second type of cell (e.g., a non-target cell), where the first state and the second state are different; for instance, the first state may be fluorescent, while the second may be less fluorescent (or substantially less fluorescent).

As an example, with respect to a pH-sensitive entity, the first type of cell may have a first intracellular pH, and the second type of cell may have a second intracellular pH, where the pH's are different by at least about 0.1, at least about 0.2, at least about 0.3, at least about 0.4, at least about 0.5, at least about 0.7, at least about 1.0, at least about 1.2, at least about 1.5, at least about 1.7, at least about 2.0 pH units, or more in some cases. If the pH-sensitive entity has different states in the first and second cell types, then the cell types may be distinguished from each other, e.g., as is discussed herein.

For instance, at a first pH (e.g., the intracellular pH of a target cell), the pH-sensitive entity may be fluorescent, and at a second pH (e.g., the intracellular pH of a non-target cell), the pH-sensitive entity may be substantially less fluorescent, e.g., producing emissions at an intensity that is less than about 50%, less than about 20%, less than about 10%, less than about 5%, less than about 2%, or less than about 1% of the first pH. In some cases, the first pH and the second pH may differ by at least about 0.5 pH units, at least about 1.0 pH unit, at least about 1.5 pH units, at least about 2.0 pH units, or more in some cases. For example, the pH-sensitive entity may be fluorescent at a pH of greater than about 7.5 and substantially less fluorescent at a pH of less than about 7, the pH-sensitive entity may be fluorescent at a pH of greater than about 7 and substantially less fluorescent at a pH of less than about 6.5, the pH-sensitive entity may be fluorescent at a pH of greater than about 6.5 and substantially less fluorescent at a pH of less than about 6, the pH-sensitive entity may be fluorescent at a pH of greater than about 6 and substantially less fluorescent at a pH of less than about 5.5, etc. (In addition, in other embodiments, any of the roles discussed here may be reversed, e.g., the pH-sensitive entity may be fluorescent at a pH of a non-target cell and substantially less fluorescent at the pH of a target cell.)

By determining fluorescence of cells within a population of cells within a sample, the first and second cell types may be distinguishable from each other. In contrast, although pH-sensitive entities or other signaling entities have previously been used to study cells, such entities have not been used to distinguish different cell types from each other.

As mentioned, various embodiments of the present invention are generally directed to the determination and/or isolation of cells of interest from a population of cells. The volume of fluid containing the cells to be analyzed may be any suitable volume, for example, femtoliters, microliters, milliliters, liters, etc. In some cases, these cells may represent a very small part of the population of cells, as previously discussed. In certain embodiments, the cells may be determined, i.e., a population of cells is studied to identify whether certain cells are present, and/or how many of those cells are present. Thus, the determination may be qualitative and/or quantitative, in various applications. In certain embodiments, the cells of interest may be isolated from the population of cells. For example, these cells may be separated from the population of cells and placed at a first location (e.g., a collection chamber), while the other cells are placed at a second location (e.g., a second collection chamber), or perhaps discarded. In some cases, the isolated cells may be further analyzed, e.g., genetically, morphologically, cytopathologically, phenotypically, etc., e.g., as discussed herein. As a non-limiting example, the genetic analysis may include a search for genetic abnormalities such as chromosome defects.

According to one set of embodiments, the cells of interest may be ones that exhibit a change in intracellular pH or other internal characteristic. For example, tumor cells often exhibit varying pH's, as compared to non-tumor cells. Without wishing to be bound by any theory, it is believed that this may be due to altered metabolic states present within the tumor cells, increased metabolism of the tumor cells relative to non-tumor cells, and/or other factors. For example, tumor cells often have the ability to use anaerobic glycolysis, even if oxygen is plentiful. Such tumor cells may be able to keep their intracellular pH at an alkaline level (e.g., around 7.4), compared to normal cells, for optimal functioning of anaerobic glycolysis. This may occur even if the extracellular pH surrounding the tumor cells is relatively acidic (e.g., around a pH of 6.8), e.g., due to the production of lactate, an end product of anaerobic glycolysis. This may occur, for instance, due to activation or overexpression of $Na^+/H^+$ pumps within the tumor cells. In contrast, normal cells may have slightly acidic intracellular pH's (e.g., around 6.8), with slightly alkaline extracellular pH's (e.g., around 7.4). Thus, since the intracellular pH of tumor cells differs from the intracellular pH of normal cells, a suitable pH-sensitive entity, such as those described herein, may be used to determine or identify the tumor cells. Thus, in one set of embodiments, tumor cells may be determined and/or isolated using suitable pH-sensitive entities, or other signaling entities such as discussed herein.

Examples of cancer or tumor cells that may be determined, e.g., using any of the methods described herein in fluids (such as blood) include, but are not limited, lymphomas, sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, synovioma, mesothelioma, lymphangioendotheliosarcoma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, non-small cell lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia. The cancer cells present may also represent a plurality of distinct cancers, in certain cases. In addition, in some cases, the stage of cancer may be determined. In some embodiments, the cancer or tumor cells are drug-resistant, or multi-drug-resistant.

As another example, fetal cells in early gestational stages often exhibit altered intracellular pHs or metabolic states, compared to maternal cells. While rare, occasionally fetal cells may cross the placenta and enter the mother's bloodstream. These cells can be identified or determined within the mother's blood (or within other suitable fluids), e.g., due to their differences in intracellular pH, in accordance with certain embodiments of the invention. Thus, in some embodiments, the present invention is generally directed to the determination and/or isolation of fetal cells from maternal cells. In some cases, the gestational age of the fetus may be determined, e.g., less than 4 weeks, less than 5 weeks, less than 6 weeks, less than 7 weeks, less than 8 weeks, less than 9 weeks, less than 10 weeks, etc.

As yet another example, stem cells may be distinguished from normal or non-stem cells in certain embodiments. In some cases, stem cells may exhibit altered intracellular pHs or metabolic states, compared to non-stem cells. The stem cells may be present, for example, in circulating blood, or in a tissue or fluid sample. For instance, the stem cells may be fetal stem cells, cord blood stem cells, embryonic stem cells, adult stem cells, tissue-specific stem cells, or induced pluripotent stem cells.

In addition, in one set of embodiments, the fluid may be acidified prior to (or after) exposure of the fluid to the pH-sensitive entity (or other signaling entity), e.g., to increase the acidity of the fluid (decrease the pH of the fluid). In one set of embodiments, the fluid may be acidified by exposure to a suitable acid, such as ethylenediaminetetraacetate acid, citric acid, ascorbic acid, dehydroascorbic acid, or the like. In some cases, the acids are those that are useful for preservation or to prevent blood coagulation, etc. The acid may be added in an amount able to decrease the pH of the fluid by at least about 0.2, at least about 0.3, at least about 0.4, at least about 0.5, at least about 0.7, at least about 1 pH units, or more in some cases. In some cases, the pH is not modified by more than about 3.0, about 2.5, about 2.0, about 1.5, or about 1.0 pH units. The acid may also be present in concentrations or pH's that are insufficient to cause extended or substantial cell death within the fluid.

In certain embodiments, the fluid may be acidified by waiting a sufficient time (e.g., with or without exposure to an acid); for example, the fluid may be kept in an open or closed container for at least about 3 hours, at least about 6 hours, at least about 9 hours, at least about 12 hours, at least about 18 hours, at least about 24 hours, at least about 30 hours, at least about 2 days, at least about 3 days, at least about 4 days, etc., and/or any range between any of these numbers. As a non-limiting example, a fluid such as blood may be kept in a container for between 24-30 hours. The fluid may be kept under such conditions at any suitable temperature, e.g., around body temperature (about 37° C.), around room temperature (about 25° C.), within a refrigerator (about 4° C.), etc. Without wishing to be bound by any theory, it is believed that cells within the fluid may continue to be metabolically active (e.g., producing acid by-products, such as lactic acid), or consume oxygen and/or produce carbon dioxide (which may form carbonic acid within the fluid), which may facilitate acidification of the fluid. Thus, in certain embodiments, the fluid may be acidified by waiting for a sufficient time.

With respect to fluid acidification, without wishing to be bound by any theory, it is believed that, somewhat counterintuitively, acidification of the fluid may promote the ability to determine or distinguish target cells from other non-target cells within the fluid using a pH-sensitive entity, at least in certain embodiments of the invention. It is believed that certain cell types, such as cancer cells or fetal cells, are metabolically active and/or have the ability to resist acidification to a greater degree than other types of cells. For example, cancer cells often exist in relatively acidic environments with poor or insufficient blood flow, and hence may exhibit more efficient mechanisms at controlling the intracellular pH even when the extracellular pH is acidic. Fetal cells may also be more metabolically active and thus be able to resist acidification to a greater extent than maternal cells. Accordingly, by acidifying the fluid, cells of interest that can resist acidification can be more readily determined or distinguished, compared to other cells that cannot resist acidification to the same degree. Thus, even though a pH-sensitive entity is used in certain embodiments, the fluid may also be acidified, before and/or after exposure of the fluid to the pH-sensitive entity.

Once exposed to a suitable signaling entity, such as a pH-sensitive entity, cells exhibiting a first characteristic (such as a first pH, e.g., an intracellular pH) may be determined and/or isolated from cells exhibiting a second characteristic (such as a second pH, e.g., an intracellular pH). Many techniques for separating cells on the basis of a signaling entity are available. For example, in some embodiments, a cell sorting machine may be used. Cell sorting machines may include flow cytometry devices and the like. A cell cytometer or a flow cytometer generally describes a machine capable of identifying, determining, and/or counting cells based on a signal emitted from the cells. Cell cytometers, amongst other devices, allow rapid determination or counting of cells based on a differential response to, e.g., electromagnetic radiation. The count of cells may be reported using any suitable technique, for example, as absolute numbers (e.g., number of cells), as a density (e.g., count in a given volume of biological fluid), in proportion to other cells in the same fluid, or the like. This may suitable in some applications, e.g., for clinical purposes, assessing metastatic potential of tumor cells, or the like.

Cell cytometers may also include additional component to further sort cells based on such response, in certain instances. For example, the cell cytometer may incorporate multiple detection stages to provide negative or positive selection of cells. Computing devices and other elements may also be used for control of processes, as well as for data analysis and storage, in some cell sorting machines. Examples include a mobile computing device, smartphone, cellular phone, tablet computer, laptop computer, or tabletop computer. Cell sorting machines may also be fixed or mobile. Many such cell sorting machines are readily available commercially. The cell sorter machine may also be used in conjunction with suitable pre-treatment steps in various embodiments, e.g., a step to first remove certain cell fractions, e.g., red blood cell, using a device, a filter, or the like.

In some embodiments, the cell sorting machine may incorporate more than one detection stage, e.g., to provide negative or positive selection of cell types, to further improve isolation of cells, etc. For example, in some cases, antibodies may be used for detection. The antibodies may be free or attached to a magnetic particle, such as a nanoparticle. As a specific non-limiting example, antibodies for CD45 may be used to further isolate leukocytes from a pH-responsive isolate of cells in order to enhance the fraction of tumor cells in the isolated cell fraction. In some cases, the cells may be exposed to antibodies able to recognize a tumor-specific antigen, such as EpCAM, EphB4, HER2, EGFR, CEA, MUC-1, CD45, or other tumor-specific antigens known to those of ordinary skill in the art. In some cases, the antibodies are organ-specific antibodies, e.g., for determining the location of a tumor. For instance, the antibodies may be used for immunostaining purposes.

In another set of embodiments, determination of cells and/or sorting may occur using fluorescence microscopy. For instance, in one set of embodiments, the cells may be positioned slides, petri dishes, etc. for analysis using a fluorescence microscope. In some cases, this process may be automated or semi-automated. For example, a plurality of cells may be analyzed or automatically screened using a fluorescence microscope to determine which cells are fluorescent and which cells are not fluorescent (or are less fluorescent), e.g., as discussed herein. A person may analyze the fluorescence of the cells, or in some cases, the images may be analyzed using a computer programmed with appropriate image analysis techniques. Many such programs for image analysis of fluorescent samples are commercially available.

As another non-limiting example, separation may use antibodies able to recognize certain cell antigens. For example, the antibody may recognize cell antigens such as CD4, CD8, CD45, CD71, anti-epsilon globin, or the like. As an example, the cells may be exposed to antibodies for fetal hemoglobin, thus separating fetal red blood cells from the initial isolated cell fraction based on factors such as pH. The remaining cells in that fraction may further be isolated in some cases using, for instance, CD4 and CD8 antibodies; for example, further selecting either cells negative for both CD4 and CD8, or positive for both CD4 and CD8 would provide for further isolation of fetal white cells. Negative selection for single positive cells (single positive or for CD4 or for CD8) also can be used in some cases. In some cases, the stem cells may be utilized for various purposes, e.g., for research or for therapeutic uses, etc.

It should be understood that in some cases, the devices or methods discussed herein may be fully or partially integrated into one or more larger devices, including human diagnostic equipment. It should also be understood that some embodiments may allow for measurement of many samples, e.g., either sequentially or simultaneously, and single experiments discussed herein are for convenience only and are not intended to be limiting.

Figure 4:
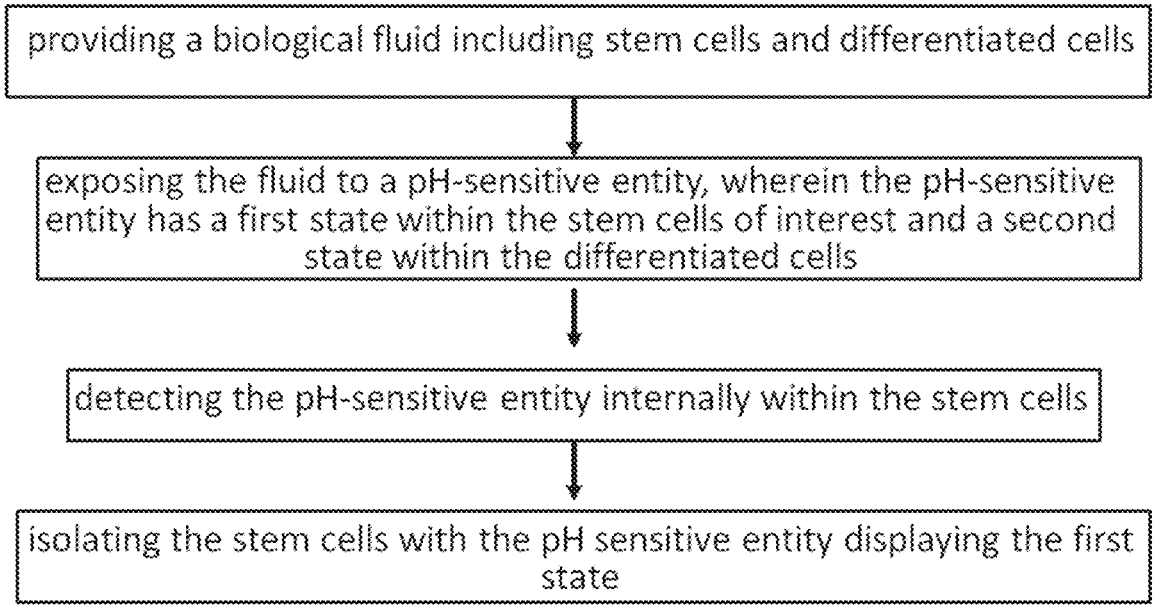
FIG. 4 shows a flowchart for a method according to one embodiment of the invention.

One example embodiment of the invention is now discussed with respect to FIG. 4 which shows a flowchart for a method, e.g., using stem cells. Although stem cells are discussed here, this is by way of example only, and other cells may also be used, e.g., any of the cells discussed herein. As shown in FIG. 4, the method may be a method for isolating totipotent, pluripotent or multipotent stem cells, including: providing a biological fluid including stem cells and differentiated cells; exposing the fluid to a pH-sensitive entity, wherein the pH-sensitive entity has a first state within the stem cells of interest and a second state within the differentiated cells; detecting the pH-sensitive entity internally within the stem cells; and, isolating the stem cells with the pH sensitive entity displaying the first state.

In some cases, a biological fluid is used. The biological fluid may be, for example, blood, cerebral spinal fluid, urine, cervical fluid, nipple aspirate, saliva, phlegm, pleural or abdominal exudate, transudate, or the like. In another embodiment, the biological fluid is prepared from a homogenized tissue sample.

In some cases, additional techniques of using, analyzing, or characterizing the stem cells may be used, and those of ordinary skill in the art will be aware of a variety of techniques for using, manipulating, storing, analyzing, etc. stem cells. For example, the stem cells may be stored in some embodiments. The cells may be stored, for example, for future medical use. Any technique for storing or preserving cells known to those of ordinary skill in the art may be used. For example, the cells may be stored in a frozen state (e.g., the storing may include cryopreservation of stem cells), and/or the storing may be performed with media formulated to encourage maintenance of stem cell pluripotentcy, such as TeSR-E8 medium from StemCell Technologies. As another example, in some cases, stem cells (e.g., isolated as discussed herein) may be transferred to a growth medium adapted to preserve stem cell characteristics of the stem cells. In some cases, the stem cells may be concentrated using known techniques. In another aspect of the method, there is an additional step of storing the stem cells In some cases, the stem cells may be identified or isolated. Stem cells allow for incredible functionality of action through their differentiation. For example, in many tissue or biological fluid samples, there is a small percentage of totipotent, pluripotent or multipotent stem cells. Identifying them may be useful in allowing for their subsequent isolation.

In some cases, for instance, a non-specific dye is added to a biological fluid. The dye may generally enter all cells, both those of interest as well as non-target cells. Non-limiting examples of dyes include any of the ones discussed herein. As a non-limiting example, a dye may be used that is adapted to have a first property in a cytosolic pH that is basic, while the dye has a second property in a cytosolic pH that is neutral or acidic. Without wishing to be bound by any theory, it is believed that the higher pH generally associated with such stem cells may generally be associated with increased glucose anabolism and associated H+/cation exchange to create a more basic environment. In some cases, the dye may be fluorescent or otherwise identifiable in the higher pH environment associated with stem cells, e.g., as discussed herein.

Once such target cells have been determined in some fashion (e.g., visualized), they may optionally be counted and/or collected. For example, collected cells may be treated using protocols known to those of ordinary skill in the art that may allow for storage of stem cells with their full capabilities intact.

Figure 5:
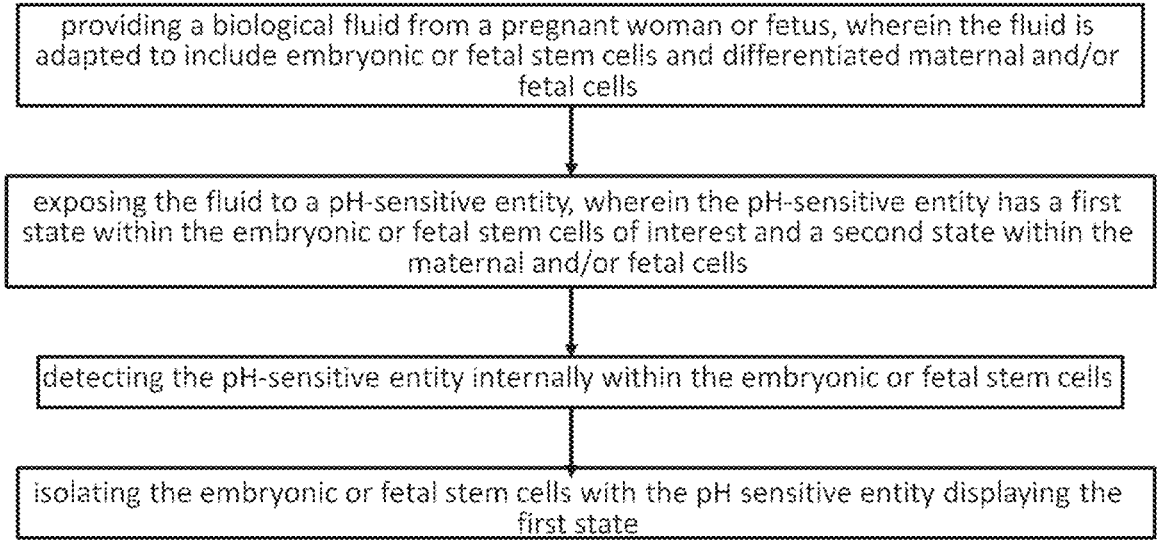
FIG. 5 shows a flowchart for a method according to another embodiment of the invention.

FIG. 5 illustrates another example embodiment showing a method for isolating totipotent or pluripotent embryonic or fetal stem cells, including providing a biological fluid from a pregnant woman or fetus, wherein the fluid is adapted to include embryonic or fetal stem cells and differentiated maternal and/or fetal cells; exposing the fluid to a pH-sensitive entity, wherein the pH-sensitive entity has a first state within the embryonic or fetal stem cells of interest and a second state within the maternal and/or fetal cells; detecting the pH-sensitive entity internally within the embryonic or fetal stem cells; and, isolating the embryonic or fetal stem cells with the pH sensitive entity displaying the first state.

In some cases, the pH-sensitive entity may be a dye or other entity discussed herein. For example, the pH-sensitive entity may be 2',7'-bis(2-carboxyethyl)-5(6)-carboxyfluorescein tetrakis(acetoxymethyl) ester (BCECF AM), 5(6)-carboxy-2',7'-dichlorofluorescein, 5(6)-carboxyfluorescein, 5(6)-carboxyfluorescein diacetate, 5(6)-carboxyfluorescein N-hydroxysuccinimide ester, 3,6-diacetoxyphthalonitrile, 6,8-dihydroxy-1,3-pyrenedisulfonic acid disodium salt, Eosin diacetate, or naphthofluorescein, etc.

As mentioned, in some embodiments, the pH-sensitive entity is fluorescent within the embryonic or fetal stem cells, and may be substantially less fluorescent in the differentiated maternal and/or fetal cells. In some cases, the pH-sensitive entity may be fluorescent within the differentiated maternal and/or fetal cells and is substantially less fluorescent in the embryonic or fetal stem cells. For example, in one set of embodiments, the pH-sensitive entity is fluorescent at a pH of greater than about 7.2 and substantially less fluorescent at a pH of less than about 7.

Without being bound by any theory, it should be understood that certain cell types, such as embryonic or fetal stem cells and adult stem cells, may engage in metabolic behavior that significantly alters their internal cellular pH, and/or there may be other changes that modify the polarity of their cytoplasm that can be determined as changes in pH. It is believed that this is reflective of reactions and processes going on in such cells, and may thus provide information not reflected in other aspects of these cells, such as their relative size or relative abundance of certain cell membrane antigens. For example, in the case of circulating pluripotent cells, a change in pH may indicate the existence of specific functional attributes that may be useful for clinical applications. In some cases, these pH changes may be significant, e.g., resulting in a change of at least about 0.5, at least about 1, at about 1.5, at least about 2, or more pH units, relative to normal intracellular pH values.

However, while some embodiments of the instant invention may be directed to the determination and/or isolation of fetal or adult pluripotent stem cells, it should be understood that these are by way of example only, and that other cell types, e.g., exhibiting changes in pH due to enhanced metabolism, disease states, external conditions (e.g., toxins or poisons, concentration of CO or $CO_2$), or the like, may also be determined and/or isolated in other embodiments of the invention. In addition, it should also be understood that fluids other than blood may be analyzed in this and other embodiments of the invention; for example, the cells may be present in other fluids such as blood serum, cerebral cervical liquid, spinal fluid, urine, nipple aspirate, phlegm, pleural abdominal exudate or transudate, amniotic fluid, saline, cell media, water, or the like. In some cases, the fluid may be one that arises biologically, e.g., from an organism such as a human. The target and non-target cells may be human and/or non-human cells. For example, in one embodiment, non-human cells present within blood (or other fluid) may be separated from human cells, e.g., on the basis of pH or other conditions. The signaling entity may in some cases, be responsive to electromagnetic radiation or other energy directed at it. In some cases, the signaling entity can specifically bind to a target cell; however, in other cases, the signaling entity can interact nonspecifically or otherwise interact with various target cells, or to other species (e.g., $H^+$ in the case of some pH-sensitive entities). The signaling entity may be a single type of molecule, or a plurality of different types of molecules in some cases. Color generation and fluorescence are non-limiting examples of a number of possible responses including, but not limited to, energy release, or chemical reactivity. Thus, a signaling entity, as used herein, is not limited to only color or fluorescence changes, and is sometimes refers to as a "dye" generically herein. It should also be understood that color generally refers to any response of the entity to treatment with electromagnetic radiation. Fluorescence, light, Raman, or other quantum-related phenomena are non-limiting examples of a response that may be referred to as a "color" change. In the present invention "fluorescence" or "fluorescent" generally refer to any response. Examples of suitable electromagnetic radiation include, but are not limited to, white light, laser light at a predetermined at least one wavelength, visible light at at least one wavelength, fluorescent light, X-ray radiation, microwave radiation, etc. or a combination of different forms of electromagnetic radiation, including but not limited to any combination of any of these. Those of ordinary skill in the art will be able to readily determine suitable electromagnetic radiation based on the signaling entity used.

In addition, it should be understood that in some cases, a fluid (e.g., blood, homogenized tissue samples, or other biological fluids such as those discussed herein) may undergo pre-treatment with chemicals, physical conditions, etc., for example, prior to and/or simultaneously with the addition of one or more signaling entities. For example, a fluid may be filtered, treated with an anticoagulant (e.g., citrate or heparin), acidified, centrifuged, or the like. As another example, the fluid may be exposed to one or more buffers. In some cases, the buffers may include buffers at different pH values.

In one set of embodiments, the signaling entity is pH-sensitive. pH sensitivity, as discussed herein, includes not only the usual definition of hydrogen ion activity in solution, but also a more extended description that includes solution polarity and the like, at least in some embodiments. The pH-sensitive entity may have at least a first color (or other determinable state) at a first pH and a second color (or other determinable state) at a second pH different from the first pH. The first pH and the second pH may be separated by at least about 0.5, at least about 1, at about 1.5, at least about 2, at least about 2.5, at least about 3, at least about 4, or at least about 5 pH units. In some cases, certain cells, such as some types of fetal or adult stem cells, may exhibit differences in intracellular pH compared to other cells in the milieu, which can be detected using pH-sensitive signaling entities.

In some cases, the signaling entity may be able to permeate cellular membranes or otherwise enter a cell, e.g., into the cytoplasm, generally due to being uncharged and aromatic. In some cases, the signaling entity can diffuse passively across a cellular membrane; in other cases, however, the signaling entity enters a cell through active processes (e.g., via phagocytosis, pinocytosis, stimulation of cell-surface receptors, or the like). The signaling entity may also be able to adapt forms and color schemes that are reflective of the pH or solvent polarity environments associated with the inner regions of such cells, and in some cases, in response to modifying molecules that may be present in such regions (e.g., enzymes). The signaling entity may be biocompatible in some fashion, although in certain cases, the signaling entity need not be biocompatible; for example, exposure of the cells to the signaling entity may injure or kill the cells, although determination of the signaling entity may still occur.

The signaling entity may be excited in some fashion, e.g., using suitable electromagnetic energy, to allow for the identification or determination of such cells, e.g., due to the unique pH-associated color found in those cells. For example, the signaling entity may exhibit fluorescence, phosphorescence, a change in absorption (e.g., at particular wavelengths), or the like. Examples of suitable electromagnetic energy include, but are not limited to, white light, laser light at a predetermined at least one wavelength, visible light at at least one wavelength, fluorescent light, X-ray radiation, microwave radiation, etc. or a combination of any of these and/or other types of electromagnetic energy.

In one set of embodiments, a signaling entity (e.g., one that is pH-sensitive) may be used to distinguish a target cell of interest (e.g., a pluripotent stem cell, etc.) from other surrounding cells that are not of interest (e.g., respectively, normal cells or maternal cells, or even fetal cells associated with prior pregnancy, etc.). Other examples are discussed herein. In some cases, for example, the signaling entity may have a first state in a first type of cell (e.g., the target cell) and a second state in a second type of cell (e.g., a non-target cell), where the first state and the second state are different; for instance, the first state may be fluorescent, while the second may be less fluorescent (or substantially less fluorescent).

As mentioned, various embodiments of the present invention are generally directed to the determination and/or isolation of cells of interest from a population of cells. The volume of fluid containing the cells to be analyzed may be any suitable volume, for example, femtoliters, microliters, milliliters, liters, etc. In some cases, these cells may represent a very small part of the population of cells, as previously discussed. In certain embodiments, the cells may be determined, i.e., a population of cells is studied to identify whether certain cells are present, and/or how many of those cells are present. Thus, the determination may be qualitative and/or quantitative, in various applications. In certain embodiments, the cells of interest may be isolated from the population of cells. For example, these cells may be separated from the population of cells and placed at a first location (e.g., a collection chamber), while the other cells are placed at a second location (e.g., a second collection chamber), or perhaps discarded. In some cases, the isolated cells may be further analyzed, e.g., genetically, morphologically, cytopathologically, phenotypically, etc., e.g., as discussed herein. As a non-limiting example, the genetic analysis may include a search for genetic abnormalities such as chromosome defects.

According to one set of embodiments, the cells of interest may be ones that exhibit a change in intracellular pH or other internal characteristic. For example, tumor cells often exhibit varying pH's, as compared to non-tumor cells. Without wishing to be bound by any theory, it is believed that this may be due to altered metabolic states present within the tumor cells, increased metabolism of the tumor cells relative to non-tumor cells, and/or other factors. For example, tumor cells often have the ability to use anaerobic glycolysis, even if oxygen is plentiful. Such tumor cells may be able to keep their intracellular pH at an alkaline level (e.g., around 7.4), compared to normal cells, for optimal functioning of anaerobic glycolysis. This may occur even if the extracellular pH surrounding the tumor cells is relatively acidic (e.g., around a pH of 6.8), e.g., due to the production of lactate, an end product of anaerobic glycolysis. This may occur, for instance, due to activation or overexpression of $Na^+/H^+$ pumps within the tumor cells. In contrast, normal cells may have slightly acidic intracellular pH's (e.g., around 6.8), with slightly alkaline extracellular pH's (e.g., around 7.4). Thus, since the intracellular pH of tumor cells differs from the intracellular pH of normal cells, a suitable pH-sensitive entity, such as those described herein, may be used to determine or identify the tumor cells. Thus, in one set of embodiments, tumor cells may be determined and/or isolated using suitable pH-sensitive entities, or other signaling entities such as discussed herein.

Certain embodiments of the present invention may be used for diagnostics applications such as for diagnosis of cancer. Such applications may include, for example, screening, differential diagnostics, personalized medicine, monitoring after curative intent therapy, or relapse. Detection of tumor cells according to certain embodiments could be used for counting tumor cells, and/or using their concentration or amount in a volume of blood, e.g., as an indication of the presence of cancer, relapse following therapy, or other applications. In another example, tumor cells isolated as discussed herein may be used in a variety of diagnostic assays or treatments known to those of ordinary skill in the art. For example, the cells may be plated on glass slides, undergo conventional cytopathology stains such as H&E or GIEMZA, undergo immunohistochemistry protocols with tissue specific antibodies to further point to the location of the tumor, or undergo genetic mutation analysis using techniques such as next generation sequencing.

In another example, tumor cells that are determined or isolated as discussed herein can be transferred to tissue culture and allowed to grow. Special tumor cell specific biological behaviors and cell and tissue morphology characteristic of tumor cells growing in tissue culture, including absence of contact inhibition and the occurrence of multilayer tissue formation, may be used in applications such as in vitro screening, differential diagnostics, personalized pharmacological screening, monitoring after curative intent therapy or relapse, etc. In some embodiments, much or all of the pathological tumor characterization generally done on biopsied tumor tissue may be less invasively done by analyzing the properties of tumor cells isolated or determined as discussed herein. For \example, tumor cell populations expanded in culture can be further tested, for instance, for sensitivity to the effects of anticancer drugs to identify individual drugs or combination therapies that are most effective at stopping the growth or killing cells from a subject's personal tumor cell population. This in vitro personalized pharmacological characterization of cell samples of a patient's tumor burden may be used to non-invasively screen for personalized therapies in some embodiments.

Thus, for instance, the tumor cells may be expanded in culture to produce larger amounts or numbers of cells, which may be used in some embodiments for combinatorial screening for tumor cell response to a large number of potential drugs, e.g., for application to a subject, or to identify new cancer treatments, etc. In some cases, rapid expansion of tumor cells in culture may be used to produce sufficient cells to allow larger scale screening to look at drug combinations that are broadened beyond known cancer treatments to also include other drugs that have proven safe, but are of variable or marginal efficacy singly or in combinations. In addition, in certain embodiments, the collection and/or expansion of tumor cells may be used for serial anti-tumor immunizations to the subject that can be used to adapt the subject to new tumor epitope patterns as they emerge in the tumor cell population during disease progression within the subject.

In some embodiments, multiple collections of tumor cells (or other cells as discussed herein) may be performed at intervals during the course of a disease such as cancer, e.g., to reevaluate pharmacological responses as the disease progresses. The efficacy of some drugs may be improved, e.g., in certain subject populations and/or in certain tumor genotype/epigenotype, and when the drug is co-administered with other drugs. Thus, techniques such as those discussed herein may be used in some embodiments for serial or personalized pharmacological study or characterization of the disease during the course of disease, such as cancer.

In one set of embodiments, tumor cells isolated as discussed herein can be used as a component of personalized tumor immunotherapy. For example, in some cases, tumor cells may be used as immunogens to sensitize components of a subject's immune system to recognize and reject tumor cells in the subject. In some embodiments, immunization may be implemented by culturing tumor cells with cellular components taken from a subject's immune system (e.g., dendritic cells, T cells and B cells, etc.), then reintroducing some of the activated immune cells back into the subject. In another embodiment, immunization may be implemented by reintroducing tumor cells from a subject back into a subject after first treating the isolated tumor cells in some fashion, e.g., by rendering the tumor cells to be replication incompetent using techniques known to those of ordinary skill in the art (for example, by irradiation or fixation or drug induced metabolic arrest, etc.). These replication-incompetent tumor cells may be activated in some embodiments, e.g., as immunogens, for example, by engineering or chemically modifying the tumor cells to express or display immune activating molecules (e.g. ligands for costimulatory receptors, ligands for pattern recognition receptors or stimulatory cytokines), by co-administering immune activating molecules in combination with the replication incompetent tumor cells, or the like.

As mentioned, in some embodiments, a cell sorting machine may be used, e.g., including any of those discussed herein. In some embodiments, the cell sorting machine may incorporate more than one detection stage, e.g., to provide negative or positive selection of cell types, to further improve isolation of cells, etc. For example, in some cases, antibodies may be used for detection. The antibodies may be free or attached to a magnetic particle, such as a nanoparticle. In addition, as another non-limiting example, an additional separation step may use antibodies able to recognize certain cell antigens. For example, the antibody may recognize cell antigens such as CD4, CD8, CD45, CD71, anti-eplison globin, or the like. As an example, the cells may be exposed to antibodies for fetal hemoglobin, thus separating fetal red blood cells from the initial isolated cell fraction based on pH. The remaining cells in that fraction may further be isolated using, for instance, CD4 and CD8 antibodies; e.g., further selecting either cells negative for both CD4 and CD8 or positive for both CD4 and CD8 would provide for further isolation of fetal white cells. Negative selection for single positive cells (single positive or for CD4 or for CD8) also can be used in some cases.

It should be understood that in some cases, the devices or methods discussed herein may be fully or partially integrated into one or more devices, including human diagnostic equipment. It should also be understood that some embodiments could allow for measurement of many samples either sequentially or simultaneously, and single experiments discussed herein are for convenience only and are not intended to be limiting.

Thus, for example, certain aspects of the invention are generally directed to devices and methods for determining target cells of interest within a fluid, e.g., using the systems and methods as discussed herein. In some cases, an uncharged molecule is introduced into a fluid containing cells, such as blood or other fluids described herein), and the uncharged molecule is allowed to penetrate into the cells, e.g., through diffusion, osmosis, phagocytosis, or the like. Within at least some of the cells, the uncharged molecule may be converted into a charged form that does not readily exit the cells. The charged form may be determined within the device, e.g., using techniques such as fluorescence, radioactivity or nuclear particle release (e.g., detection of gamma rays, beta particles, and/or alpha particles, etc.), color changes, energy release, electromagnetic radiation release, chemical reactivity, biological reactivity, chemical polarity, solubility changes, or the like.

In one set of embodiments, the device is a device for isolating totipotent, pluripotent or multipotent stem cells, comprising: a fluid comprising target pluripotent stem cells of interest and non-target differentiated cells; a pH-sensitive entity adapted to be internalized within all cells in the fluid, wherein the pH-sensitive entity has a first state within the stem cells of and a second state within the non-target differentiated cells; and, a cell selector unit adapted to identify the first state of the pH-sensitive entity.

In another aspect of the device, the cell selector is realized as a cell cytometer or microscope adapted to able to count cells. In another aspect of the device, the cell cytometer or microscope is adapted to isolate and/or sort cells. In another aspect of the device, the pluripotent stem cells are associated with a human organ. In another aspect of the device, the pluripotent stem cells are associated with a fetal source. In another aspect of the device, the fluid is selected from blood, blood serum, cerebral spinal fluid, urine, cervical fluid, nipple aspirate, saliva, phlegm, pleural or abdominal exudate or transudate.

Figure 6:
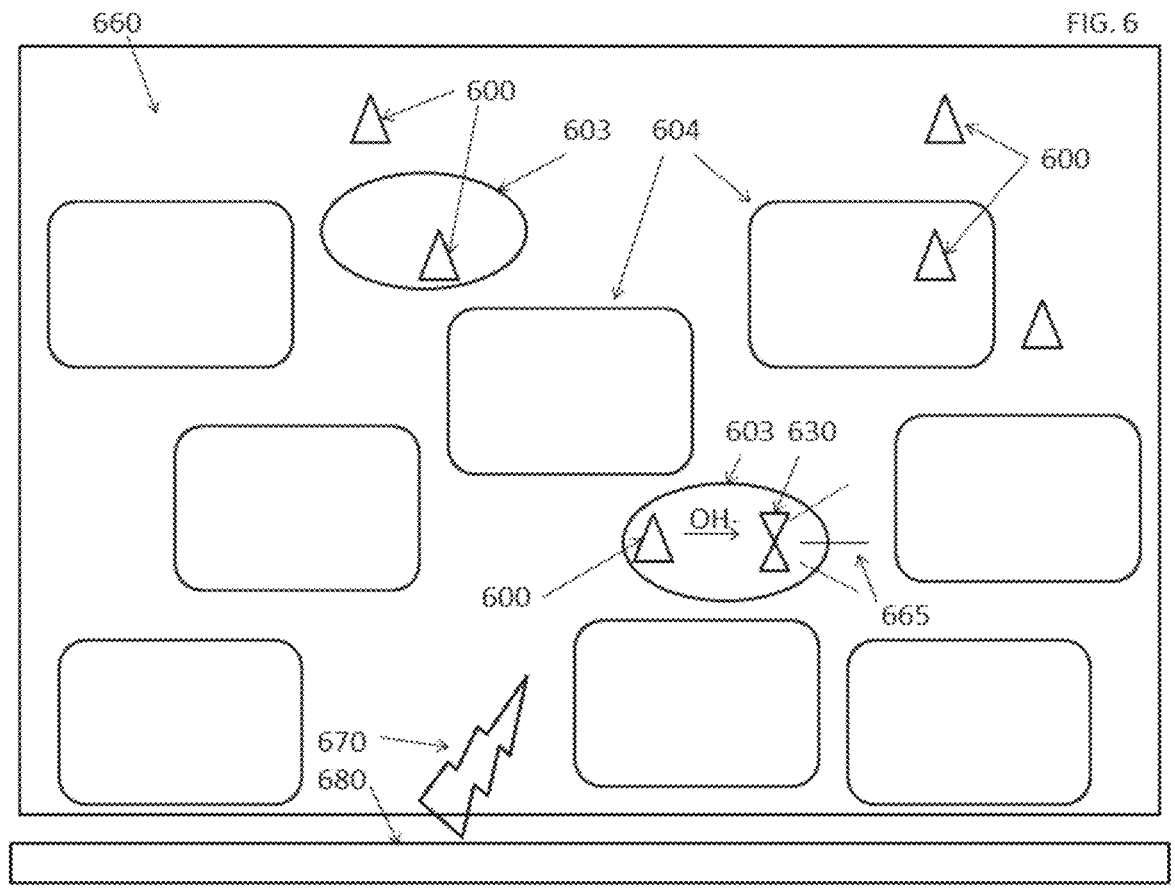
FIG. 6 shows a schematic view of an embodiment according to the instant invention.

Attention is turned to FIG. 6 which shows a schematic view of a non-limiting embodiment of the instant invention. In this figure, an uncharged pH dye 600 is added to a pregnant woman's blood 360 that includes target embryonic or fetal stem cells 603 and non-target differentiated maternal blood cells 604. Uncharged pH dye 600 enters both embryonic or fetal stem cells 603 and non-target differentiated maternal blood cells 604, as shown. In embryotic stem cells 603, uncharged compound 300 is converted, by virtue of the alkaline pH in the cytosol into a charged compound 330 incapable of leaving the stem cells 603. Charged compound 630 is adapted to fluoresce 665 when excited with appropriate electromagnetic radiation 670 from a cell sorter 680. Embryotic stem cells 603 may be identified by charged compound 630 fluorescence 665, and in some cases isolated and stored cryogenically for future medical use by the adult whose fetal cells have been identified and stored.

Without being bound by any theory, the following discussion is offered to provide greater insight into certain embodiments, e.g., where a signaling molecule, or other entity, is introduced into cells. The present invention, in some embodiments thereof, relates to methods and devices for delivering a charged compound into a cytosol or organelle of a cell. In some embodiments, an uncharged molecule or compound is allowed to enter cells in a sample; in cells of interest does the uncharged molecule undergo a chemical or biochemical transformation to at least one charged molecule that cannot leave the cell which it entered. For example, the uncharged molecule or compound may become charged through a change in pH, interaction with an enzyme such as an esterase or a protease, or the like, e.g., as discussed herein. Non-limiting examples of potentially suitable uncharged molecules are well-known. The charged molecule may have desirable properties including, but not limited to, fluorescence or therapeutic action on the cell in which it is located. In a non-target cell, for example, the uncharged molecule may remain in its original state and generally has neither properties for identification or therapeutic action. For instance, in some cases, in the non-target cell, less than about 30%, less than about 25%, less than about 20%, less than about 15%, less than about 10%, or less than about 5% of the uncharged molecule is converted into a charged state.

It is well known that charged molecules generally do not pass through cellular membranes, unless they are brought into a cell, e.g., via a specific transfer mechanism. This barrier to entry may present a challenge to delivering either biologically active treatments or specific probes to cells. On the other hand, uncharged molecules, especially those with extended pi rings, can often pass through hydrophobic membrane barriers.

As described in U.S. patent application Ser. No. 14/103,170, filed Dec. 11, 2013, and U.S. patent application Ser. No. 14/225,512, filed Mar. 26, 2014, each incorporated herein by reference in its entirety, it has been discovered, for example, that circulating tumor cells (CTC's) and circulating fetal cells (CFC's) may have alkaline cytosolic pH values which allow for conversion of uncharged pH dyes to be made charged and fluorescent. Some embodiments of the invention describes phenomena related to trapping charged molecules in a predetermined cell or group of cells based on cell-specific chemical or other activities that are adapted to convert uncharged molecules into charged molecules unable to escape the target cell(s). For example, it is understood that a plurality of signaling molecules may be employed to enter either target and/or non-target cell types. In some embodiments, non-target cells may be targeted with signaling material, while target cells lack a specific activity to transform the uncharged compound into a charged compound that may readily be identified through color, fluorescence or other appropriate techniques. In other embodiments, however, the opposite is true, e.g., target cells may be targeted with signaling material, while non-target cells lack a specific activity to transform the uncharged compound into a charged compound.

Certain embodiments of the instant invention have been show discrimination of target to non-target cells at ratios of at least about 1:10, at least about 1:100, at least about 1:1,000, at least about 1:10,000, at least about 1:100,00, at least about 1:1,000,000, or higher in some cases.

Some embodiments can distinguish alkaline from acidic cells, e.g., where target cells are alkaline internally and non-target cells are acidic or neutral, or vice versa. Additionally and/or alternatively, embodiments can allow for detection of target cells from non-target cells, wherein target cells include acidic intern pH values and non-target cells show neutral or alkaline pH readings in cellular spaces.

While pH-sensitive entities were described above, it should be understood that other uncharged molecules or compounds may also be used in other embodiments as signaling entities, in addition to or instead of the above-described pH-sensitive entities. For example, the charged compound may be detected using, for example, radioactivity, color, fluorescence, energy release, chemical reactivity, biological reactivity, chemical polarity, or solubility, e.g., using an appropriate signaling entity. Non-limiting examples of such compounds are given in Table 1.

In some cases, the unchanged molecule or compound may be generally polar solvent soluble so as to allow its dissolution in a liquid which may be added directly or after water dilution to a fluid containing cells. For example, the polar solvent may be water, DMSO, or other suitable polar solvents. Without wishing to be bound by any theory, it is believed that the lack of charge facilitates movement of uncharged molecule through an outer membrane of a cell and in some embodiments through additional membranes of organelles such as those associated with mitochondria and nuclei.

Once entered a cell, the molecule may be allowed to remain within the cells, e.g., to be converted into a charged form. The uncharged molecule may become charged within the cell, or within a specific region or portion of the cell, e.g., in the cytoplasm, within an organelle such as a mitochondrion, etc. For example, the compound may become charged at a pH of a cytosol of a target cell. The charged state may be positive or negative.

In some embodiments, the compound, when charged, may exhibit anti-cancer, anti-bacterial, or anti-inflammatory behavior. However, in some cases, the compound may have relatively low therapeutic effects when in an uncharged state, although this is not a requirement. The uncharged compound may be generally solvent in water, polar solvents or water-polar solvent mixtures. For example, a protease inhibitor may be in an inactive form when part of an uncharged molecule adapted to pass through cellular membranes; when the uncharged molecule is chemically or biochemically converted to a charged molecule, the charged molecule may be converted into an active protease inhibitor. The protease inhibitor may thus kill the target cell, which may be a cancer cell or the like.

In some cases, the compound may generally diffuse or be actively transported through a cellular membrane when in an unchanged state. The compound may be polar in some embodiments, and/or the compound may include internal charges that cancel to yield a net charge of zero. In some cases, the compound may be zwitterionic or may be fully or partially charged under some conditions.

The time (e.g., "incubation time") may be anywhere between a few minutes to hours or days. For example, time may be given to allow the uncharged molecule to enter as many of the cells in a sample as possible. For example, the time may be half an hour or less, one hour or less, two hours or less, three hours or less, four hours or less, six hours or less, twelve hours or less, or twenty-four hours, or less. More than twenty-four hours is also possible in some cases. The conversion of the uncharged compound into a charged compound (or more than one charged compound in some cases) generally occurs in the target cell. In some cases, this may occur without any manipulation and/or energy addition from an external source.

Conditions such as pH or presence of specific catalytic entities within a target cell may be used to drive the conversion from an unchanged state to a charged state. In some cases, such conditions may not occur in non-target cells, or may occur, but at at very low rates or concentrations so as to make the product insignificant, or at least distinguishable with respect to the target cells.

A non-limiting example of a condition within a target cell that may be different from a non-target cell is pH. Examples of pH differences include any of those provided herein. In some cases, for example, an uncharged molecule may become charged at a basic pH value, e.g., a value higher than about 7.0, higher than about 7.5, higher than about 8.0, etc. In some embodiments, an uncharged molecule may become charged at an acidic pH value, e.g., a value less than about 7.0, less than about 6.5, less than about 6.0, etc.

However, the invention is not limited to only pH or pH changes. In another set of embodiments, an enzyme or a metallic catalyst may be able to convert an uncharged molecule into a charged molecule. For example, the enzyme may be an esterase or a protease. Non-limiting examples of specific molecules that can be altered using enzymes or catalysts (e.g., metal catalysts) can be seen in Table 1.

TABLE 1

| Name/chemical name | Structure | |
| --- | --- | --- |
| Azactidine<br>4-amino-1-((2R,3R,4S,5R)-3,4-dihydroxy-5-(hydroxymethyl)tetrahydrofuran-2-yl)-1,3,5-triazin-2(1H)-one | $C_8H_{12}N_4O_5$ | [structure of azacitidine] |
| Bendamistine (Cl)<br>4-[5-[bis(2-chloroethyl)amino]-1-methyl-benzimidazol-2-yl]butanoic acid hydrochloride | $C_{16}H_{22}Cl_3N_3O_2$ | [structure of bendamustine] |
| Bustafan<br>butane-1,4-diyl dimethanesulfonate | $C_6H_{14}O_6S_2$ | [structure of busulfan] |

TABLE 1-continued

| Name/chemical name | Structure |
| --- | --- |
| Carmustin | $C_5H_9Cl_2N_3O_2$ (1-(2-chloroethyl)-3-(2-chloroethyl)-1-nitrosourea structure) |
| Carboplatin | $C_6H_{12}N_2O_4Pt$ (cyclobutane-1,1-dicarboxylate platinum diammine structure) |
| Chlorambucil<br>4-(4-(bis(2-chloroethyl)amino)phenyl)butanoic acid | $C_{14}H_{19}Cl_2NO_2$ |
| Cyclophosphamide<br>2-[bis(2-chloroethyl)amino]tetrahydro-2H-1,3,2-oxazaphosphorine 2-oxide monohydrate | $C_7H_{15}Cl_2N_2O_2P$ |
| Dacarbazine<br>(E)-5-(3,3-dimethyltriaz-1-en-1-yl)-1H-imidazole-4-carboxamide | $C_6H_{10}N_6O$ |
| Diaziquone<br>diethyl (2,5-di(aziridin-1-yl)-3,6-dioxocyclohexa-1,4-diene-1,4-diyl)dicarbamate | $C_{16}H_{20}N_4O_6$ |

TABLE 1-continued

| Name/chemical name | Structure |
|---|---|
| Ifosfamide<br>3-(2-chloroethyl)-2-((2-chloroethyl)amino)-1,3,2-oxazaphosphinane 2-oxide | $C_7H_{15}Cl_2N_2O_2P$ |
| Melphalan Hydrochloride<br>(S)-2-amino-3-(4-(bis(2-chloroethyl)amino)phenyl)propanoic acid hydrochloride | $C_{13}H_{18}Cl_2N_2O_2$ |
| Methylisoindigotin<br>(E)-1,1'-dimethyl-[3,3'-biindolinylidene]-2,2'-dione | $C_{18}H_{14}N_2O_2$ |
| Procarbazine<br>N-isopropyl-4-[(2-methylhydrazino)methyl]benzamide | $C_{12}H_{19}N_3O$ |
| Streptozocin<br>1-methyl-1-nitroso-3-((3R,4R,5S,6R)-2,4,5-trihydroxy-6-(hydroxymethyl)tetrahydro-2H-pyran-3-yl)urea | $C_8H_{15}N_3O_7Ub.$ |
| Temozolomide<br>3-methyl-4-oxo-3,4-dihydroimidazo[5,1-d][1,2,3,5]tetrazine-8-carboxamide. | $C_6H_6N_6O_2$ |

TABLE 1-continued

| Name/chemical name | Structure |
|---|---|
| Pemetrexed Disodium<br>sodium (S)-2-(4-(2-(2-amino-4-oxo-4,7-dihydro-1H-pyrrolo[2,3-d]pyrimidin-5-yl)ethyl)benzamido)pentanedioate heptahydrate. | $C_{20}H_{33}N_5Na_2O_{13}$ 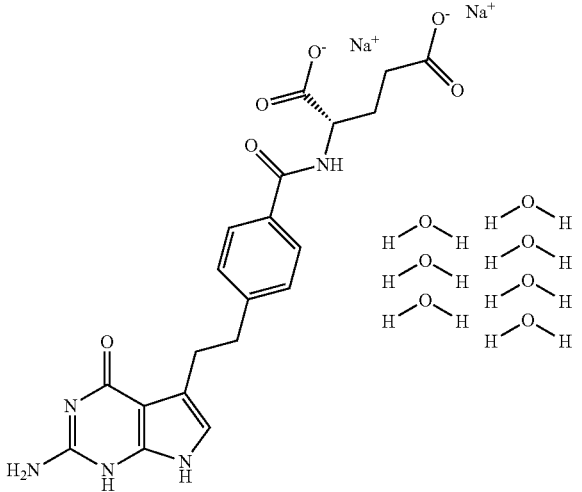 |
| Raltitrexed<br>(S)-2-(5-(methyl((2-methyl-4-oxo-1,4-dihydroquinazolin-6-yl)methyl)amino)thiophene-2-carboxamido)pentanedioic acid | $C_{21}H_{22}N_4O_6S$ 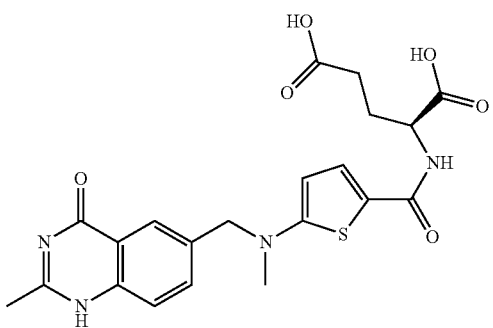 |
| Capecitabine<br>pentyl (1-((2R,3R,4S,5R)-3,4-dihydroxy-5-methyltetrahydrofuran-2-yl)-5-fluoro-2-oxo-1,2-dihydropyrimidin-4-yl) carbamate | $C_{15}H_{22}FN_3O_6$ 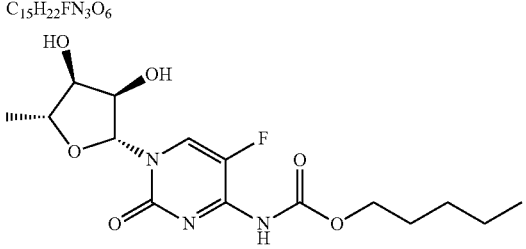 [SMILES: "C15H22FN3O6" ; CCCCCOC(=O)Nc1nc(=O)n([C@@H]2O[C@H](C)[C@@H](O)[C@H]2O)cc1F] |
| Cytarabine<br>4-amino-1-[(2R,3S,4R,5R)-3,4-dihydroxy-5-(hydroxymethyl)oxolan-2-yl]pyrimidin-2-one | $C_9H_{13}N_3O_6$ 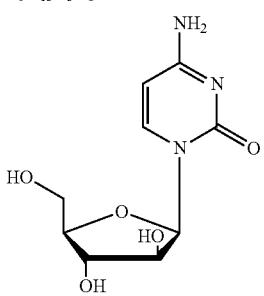 |

TABLE 1-continued

| Name/chemical name | Structure |
|---|---|
| 5-Fluoro Uracil<br>5-fluoro-1H,3H-pyrimidine-2,4-dione | $C_4H_3FN_2O_2$ |
| Fludarabine phosphate<br>((2R,3S,4S,5R)-5-(6-amino-2-fluoro-9H-purin-9-yl)-3,4-dihydroxytetrahydrofuran-2-yl)methyl dihydrogen phosphate | $C_{10}H_{13}FN_5O_7P$ |
| Gemcitabine hydrochloride<br>4-amino-1-((2R,4R,5R)-3,3-difluoro-4-hydroxy-5-(hydroxymethyl)tetrahydrofuran-2-yl)pyrimidin-2(1H)-one hydrochloride | $C_9H_{11}F_2N_3O_4$ |
| Methotrexate<br>(S)-2-(4-(((2,4-diaminopteridin-6-yl)methyl)(methyl)amino)benzamido)pentanedioic acid. | $C_{20}H_{22}N_8O_5$ |
| Pemetrexed disidum<br>sodium (S)-2-(4-(2-(2-amino-4-oxo-4,7-dihydro-1H-pyrrolo[2,3-d]pyrimidin-5-yl)ethyl)benzamido)pentanedioate heptahydrate. | $C_{20}H_{33}N_5Na_2O_{13}$ |

TABLE 1-continued
| Name/chemical name | Structure |
| --- | --- |
| LY294002<br>2-(4-morpholinyl)-8-phenyl-4H-1-benzopyran-4-one | $C_{19}H_{17}NO_3$<br>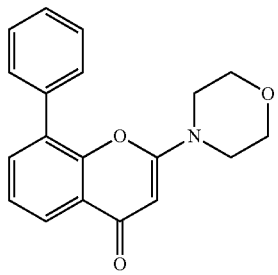 |
| Deguelin<br>(7aS,13aS)-13,13a-Dihydro-9,10-dimethoxy-3,3-dimethyl-3H-bis[1]benzopyrano[3,4-b:6',5'-e]pyran-7(7aH)-one | $C_{23}H_{22}O_6$<br>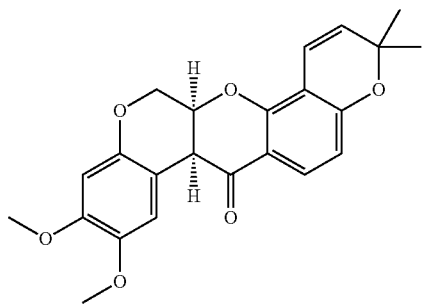 |
| Raltitrexed<br>(S)-2-(5-(methyl((2-methyl-4-oxo-1,4-dihydroquinazolin-6-yl)methyl)amino)thiophene-2-carboxamido)pentanedioic acid | $C_{21}H_{22}N_4O_6S$<br>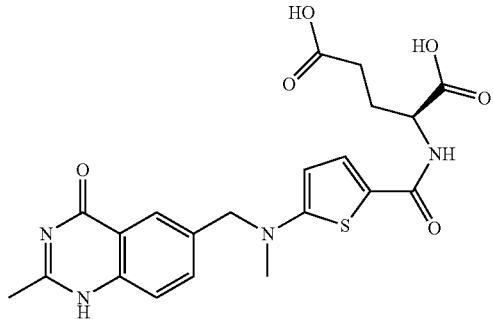 |

TABLE 1-continued

| Name/chemical name | Structure |
| --- | --- |
| Dactinomycin<br>2-amino-N1,N9-bis(6,13-diisopropyl-2,5,9-trimethyl-1,4,7,11,14-pentaoxo-hexadecahydro-1H-pyrrolo[2,1-i][1,4,7,10,13]oxatetraazacyclohexadecin-10-yl)-4,6-dimethyl-3-oxo-3H-phenoxazine-1,9-dicarboxamide | $C_{62}H_{66}N_{12}O_{16}$ |
| Bleomycin<br>3-[[2-[2-[2-[2-[4-[2-[6-Amino-2-[1-(2-amino-2-carbamoyl-ethyl)amino-2-carbamoyl-ethyl]-5-methyl-pyrimidin-4-yl]carbonylamino-3-[3-[4-carbamoyloxy-3,5-dihydroxy-6-(hydroxymethyl)tetrahydropyran-2-yl]oxy-4,5-dihydroxy-6-(hydroxymethyl)tetrahydropyran-2-yl]oxy-3-(3H-imidazol-4-yl)propanoyl]amino-3-hydroxy-2-methyl-pentanoyl]amino-3-hydroxy-butanoyl]aminoethyl]-1,3-thiazol-4-yl]-1,3-thiazol-4-yl]carbonylamino]propyl-dimethyl-sulfonium hydrogen sulfate | $C_{55}H_{54}N_{17}O_{21}S_3$ |
| Daunorubicin hydrochlorid<br>(8S-cis)-8-Acetyl-10-((3-amino-2,3,6-trideoxy-alpha-L-lyxo-hexopyranosyl)oxy)-7,8,9,10-tetrahydro-6,8,11-trihydroxy-1-methoxy-5,12-naphthacenedione hydrochloride | $C_{27}H_{29}NO_{10}$ |

TABLE 1-continued

| Name/chemical name | Structure |
|---|---|
| Doxorubicin (8S,10S)-10-(((2R,4S,5S,6S)-4-amino-5-hydroxy-6-methyltetrahydro-2H-pyran-2-yl)oxy)-6,8,11-trihydroxy-8-(2-hydroxy-acetyl)-1-methoxy-7,8,9,10-tetrahydro-tetracene-5,12-dione hydrochloride | $C_{27}H_{29}NO_{11}$ 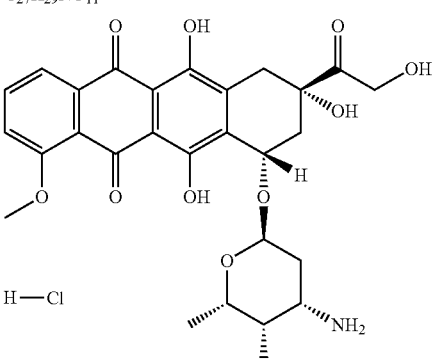 |
| Epirubicin (8S,10S)-10-(((2R,4S,5R,6S)-4-amino-5-hydroxy-6-methyltetrahydro-2H-pyran-2-yl)oxy)-6,8,11-trihydroxy-8-(2-hydroxy-acetyl)-1-methoxy-7,8,9,10-tetrahydro-tetracene-5,12-dione hydrochloride | $C_{27}H_{29}NO_{11}$ 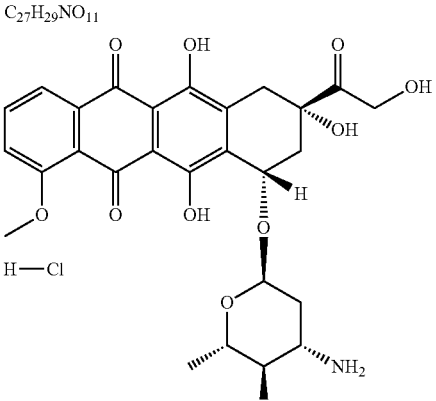 |
| Idarubicin (7S,9S)-9-acetyl-7-(((2R,4S,5S,6S)-4-amino-5-hydroxy-6-methyltetrahydro-2H-pyran-2-yl)oxy)-6,9,11-trihydroxy-7,8,9,10-tetrahydrotetracene-5,12-dione hydrochloride | $C_{26}H_{27}NO_{9}$ 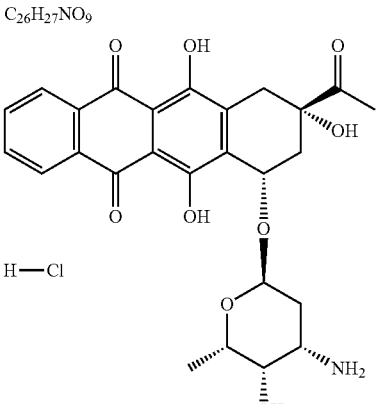 |
| Mitomycin ((1aS,8S,8aR,8bS)-6-amino-8a-methoxy-5-methyl-4,7-dioxo-1,1a,2,4,7,8,8a,8b-octahydroazirino[2',3':3,4]pyrrolo[1,2-a]indol-8-yl)methyl carbamate | $C_{15}H_{18}N_{4}O_{5}$ 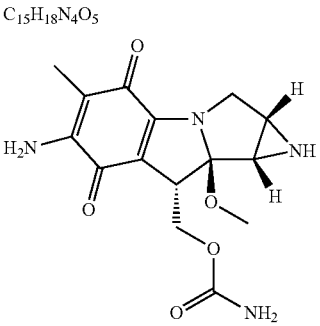 |

TABLE 1-continued

| Name/chemical name | Structure |
| --- | --- |
| Mitoxantrone hydrochlorid 1,4-dihydroxy-5,8-bis((2-((2-hydroxyethyl)amino)ethyl)amino) anthracene-9,10-dione dihydrochloride | $C_{22}H_{28}N_4O_6$ 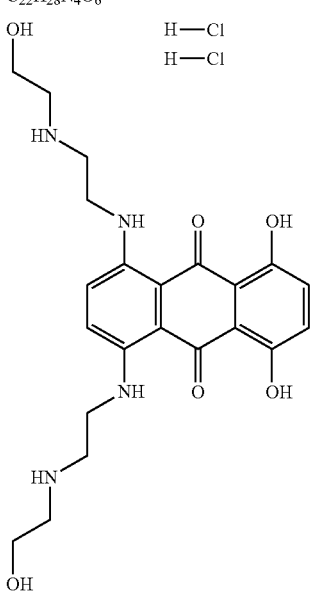 |
| Etoposide (5R,5aR)-9-(((2R,4aR,6R,7R,8R,8aS)-7,8-dihydroxy-2-methylhexahydropyrano[3,2-d][1,3]dioxin-6-yl)oxy)-5-(4-hydroxy-3,5-dimethoxyphenyl)-5,5a,8a,9-tetrahydrofuro[3',4':6,7]naphtho[2,3-d][1,3]dioxol-6(8H)-one | $C_{29}H_{32}O_{13}$ 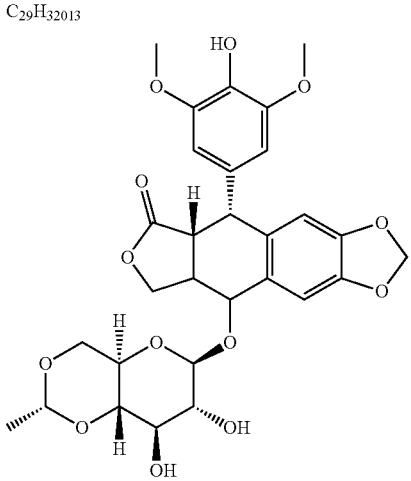 |
| Irinotecan hydrochloride (S)-4,11-diethyl-4-hydroxy-3,14-dioxo-3,4,12,14-tetrahydro-1H-pyrano[3',4':6,7]indolizino[1,2-b]quinolin-9-yl[1,4'-bi-piperidine]-1'-carboxylate hydrochloride trihydrate. | $C_{33}H_{45}ClN_4O_9$ 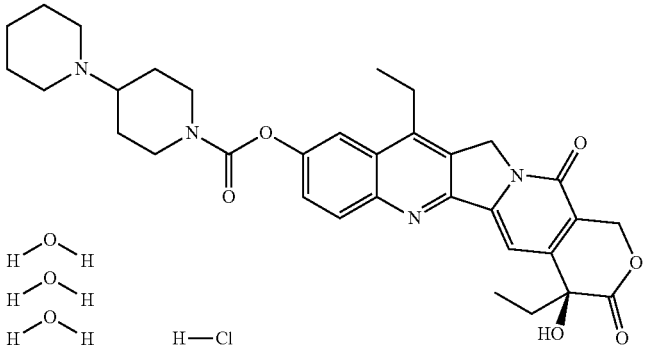 |

TABLE 1-continued

| Name/chemical name | Structure |
|---|---|
| Palcitaxel (2aR,4S,4aS,6R,9S,11S,12S,12aR,12bS)-9-(((2R,3S)-3-benzamido-2-hydroxy-3-phenylpropanoyl)oxy)-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate | $C_{47}H_{51}NO_{14}$ |
| Topotecan (S)-10-((dimethylamino)methyl)-4-ethyl-4,9-dihydroxy-1H-pyrano[3',4':6,7]indolizino[1,2-b]quinoline-3,14(4H,12H)-dione hydrochloride | $C_{23}H_{23}N_3O_5$ |
| Vinblasine (3aR,3a1R,4R,5S,5aR,10bR)-methyl 4-acetoxy-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a1,4,5,5a,6,11,12-octahydro-1H-indolizino[8,1-cd]carbazole-5-carboxylate sulfate | $C_{46}H_{58}N_4O_9$ |
| Vincristine sulfate (3aR,3a1R,4R,5S,5aR,10bR)-methyl 4-acetoxy-3a-ethyl-9-((3S,5S,7S,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-6-formyl-5-hydroxy-8-methoxy-3a,3a1,4,5,5a,6,11,12-octahydro-1H-indolizino[8,1-cd]carbazole-5-carboxylate sulfate. | $C_{46}H_{58}N_4O_{14}S$ |

TABLE 1-continued

| Name/chemical name | Structure |
| --- | --- |
| Vinorelbine tartrate<br>(3aR,3a1R,4R,5S,5aR,10bR)-methyl 4-acetoxy-3a-ethyl-9-((2R,8S)-4-ethyl-8-(methoxycarbonyl)-1,3,6,7,8,9-hexahydro-2,6-methanoazecino[4,3-b]indol-8-yl)-5-hydroxy-8-methoxy-6-methyl-3a,3a1,4,5,5a,6,11,12-octahydro-1H-indolizino[8,1-cd]carbazole-5-carboxylate bis((2R,3R)-2,3-dihydroxysuccinate) | $C_{45}H_{54}N_4O_8$ |
| Carboplatin<br>platinum, diammine[1,1-cyclobutanedicarboxylato(2−)-O,O']—, (SP-4-2) | $C_6H_{12}N_2O_4Pt$ |
| Cisplatin<br>(SP-4-2)-diamminedichloroplatinum;<br>platinum, diaminedichloro-, cis- (8CI). | $Cl_2H_6N_2Pt_2$ |
| Oxaliplatin<br>[(1R,2R)-cyclohexane-1,2-diamine](ethanedioato-O,O')platinum(II) | $C_8H_{14}N_2O_4Pt$ |

TABLE 1-continued
| Name/chemical name | Structure |
|---|---|
| Ametantrone<br>1,4-bis((2-((2-hydroxyethyl)amino)ethyl)amino)anthracene-9,10-dione | $C_{22}H_{28}N_4O_4$ 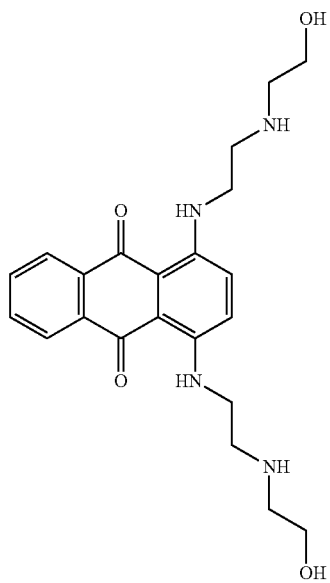 |
| Apaziquone<br>5-(aziridin-1-yl)-3-(hydroxymethyl)-2-[(E)-3-hydroxyprop-1-enyl]-1-methylindole-4,7-dione | $C_{15}H_{16}N_2O_4$ 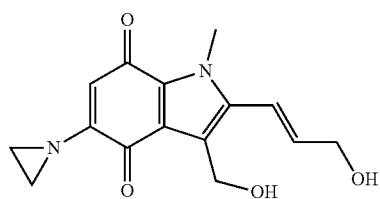 |
| Bromcresol Green | $C_{21}H_{14}Br_4O_5S$ 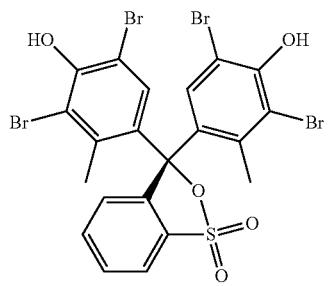 |

TABLE 1-continued

| Name/chemical name | Structure |
| --- | --- |
| Bevacizumab | $C_{14}H_{18}ILiN_2O_3$ 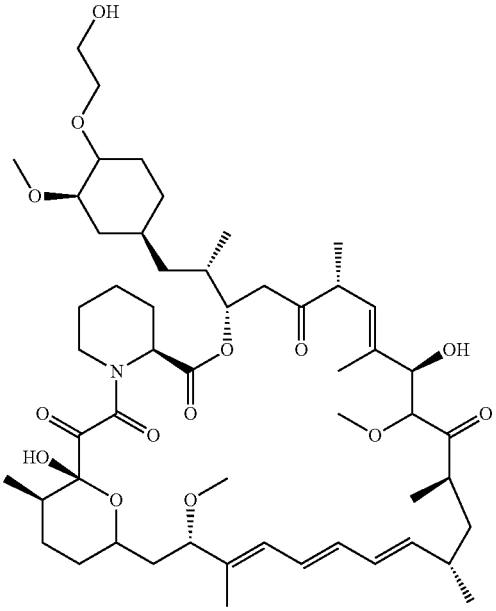 |
| Erlotinib hydrichlorid N-(3-Ethynylphenyl)-6,7-bis(2-methoxy-ethoxy)-4-quinazolinamine Mono-hydrochloride. | $C_{22}H_{23}N_3O_4$ 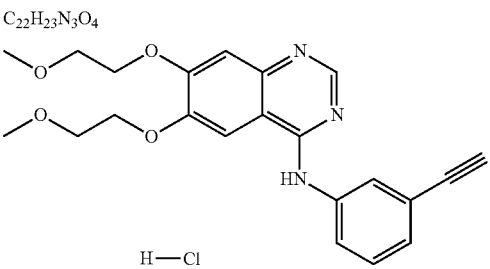 |
| Geftinib N-(3-chloro-4-fluorophenyl)-7-methoxy-6-(3-morpholinopropoxy)quinazolin-4-amine | $C_{22}H_{24}ClFN_4O_3$ 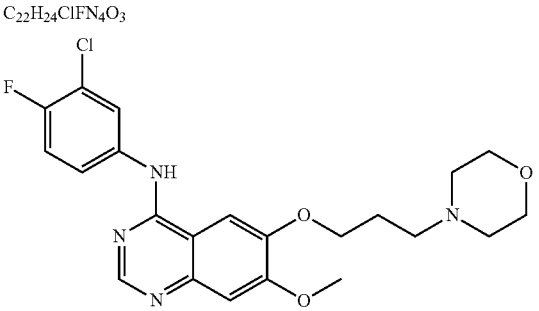 [SMILES: "C22H24ClFN4O3" ; COc1cc2ncnc(Nc3ccc(F)c(Cl)c3)c2cc1OCCCN1CCOCC1] |
| Imatinib mesylate N-(4-methyl-3-((4-(pyridin-3-yl) pyrimidin-2-yl)amino)phenyl)-4-((4-methylpiperazin-1-yl)methyl) benzamide methanesulfonate | $C_{29}H_{31}N_7O$ 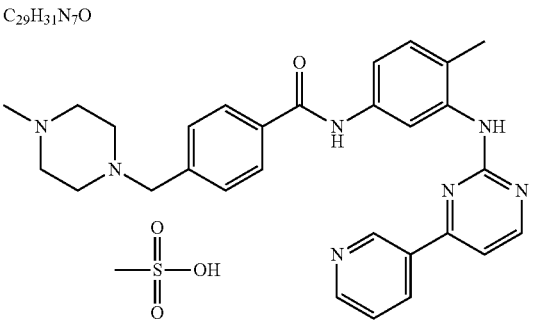 |

TABLE 1-continued

| Name/chemical name | Structure |
|---|---|
| Lapatinib<br>N-(3-chloro-4-((3-fluorobenzyl)oxy)<br>phenyl)-6-(5-(((2-(methylsulfonyl)<br>ethyl)amino)methyl)furan-2-yl)<br>quinazolin-4-amine | $C_{29}H_{26}ClFN_4O_4S$<br>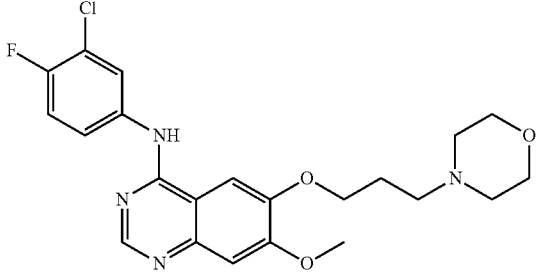 |
| Sunitinib malate<br>(Z)-N-(2-(diethylamino)ethyl)-5-((5-<br>fluoro-2-oxoindolin-3-ylidene)<br>methyl)-2,4-dimethyl-1H-pyrrole-3-<br>carboxamide malate | $C_{22}H_{27}FN_4O_2$<br>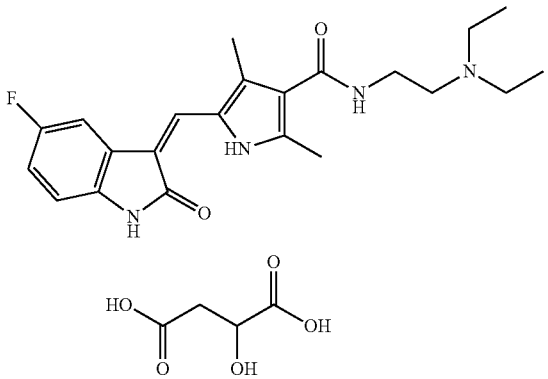 |
| Saracatinib<br>N-(5-Chloro-1,3-benzodioxol-4-yl)-<br>7-[2-(4-methyl-1-piperazinyl)ethoxy]-<br>5-[(tetrahydro-2H-pyran-4-yl)oxy]-4-<br>quinazolinamine | $C_{27}H_{32}ClN_5O_5$<br>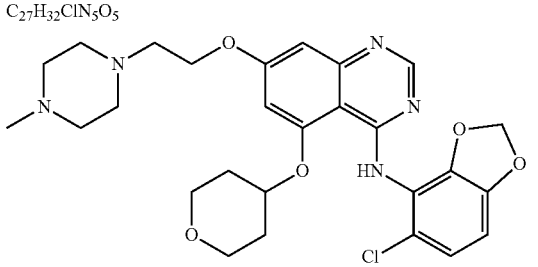 [SMILES: "C27H32ClN5O5" ; CN1CCN(CCOc2cc(OC3CCOCC3)c3c(Nc4c(Cl)ccc5c4OCO5)ncnc3c2)CC1] |
| Sorafenib<br>4-(4-(3-(4-chloro-3-(trifluoromethyl)<br>phenyl)ureido)phenoxy)-N-<br>methylpicolinamide 4-<br>methylbenzenesulfonate. | $C_{21}H_{16}ClF_3N_4O_3$<br>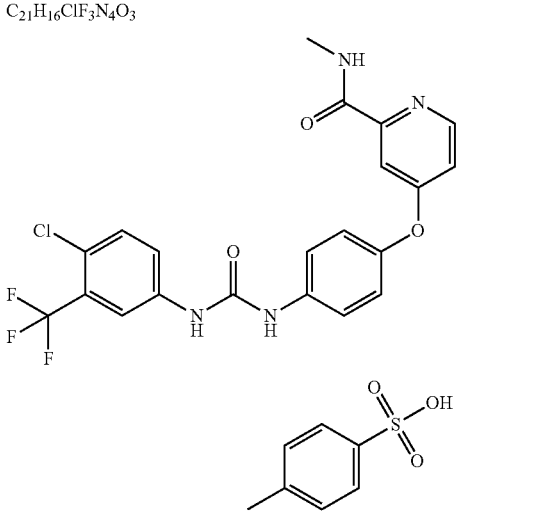 [SMILES: "C21H16ClF3N4O3" ; CNC(=O)c1cc(Oc2ccc(NC(=O)Nc3ccc(Cl)c(C(F)(F)F)c3)cc2)ccn1 ; Cc1ccc(S(=O)(=O)O)cc1] |

TABLE 1-continued

| Name/chemical name | Structure |
| --- | --- |
| Tozasertib (N-[4({4-(4-methylpiperazin-1-yl)-6-[(3-methyl-1H-pyrazol-5-yl)amino]pyrimidin-2-yl}thio)phenyl]cyclopropanecarboxamide) | $C_{23}H_{28}N_8OS$ 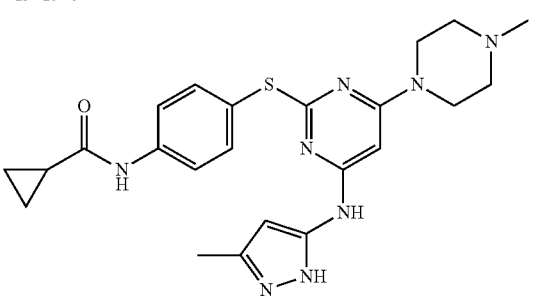 |
| Plerixafor 1,4-bis((1,4,8,11-tetraazacyclo-tetradecan-1-yl)methyl)benzene | $C_{28}H_{54}N_8 \cdot 8HCl$ 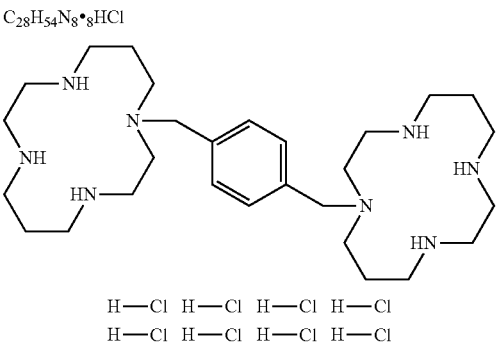 |
| Temsirolimus (1R,2R,4S)-4-{(2R)-2-[(3S,6R,7E,9R,10R,12R,14S,15E,17E,19E,21S,23S,26R,27R,34aS)-9,27-dihydroxy-10,21-dimethoxy-6,8,12,14,20,26-hexamethyl-1,5,11,28,29-pentaoxo-1,4,5,6,9,10,11,12,13,14,21,22,23,24,25,26,27,28,29,31,32,33,34,34a-tetracosahydro-3H-23,27-epoxypyrido[2,1-c][1,4]oxazacyclo-hentriacontin-3-yl]propyl}-2-methoxycyclohexyl 3-hydroxy-2-(hydroxymethyl)-2-methylpropanoate | $C_{56}H_{87}NO_{16}$ 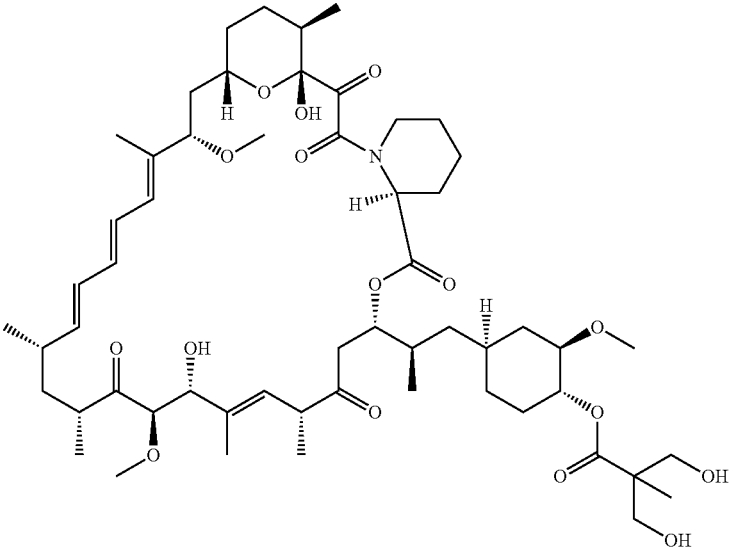 |
| Clodronate (2S,3S,4R,5R)-5-(6-amino-2-chloro-9H-purin-9-yl)-4-fluoro-2-(hydroxy-methyl)tetrahydrofuran-3-ol | $C_{10}H_{11}ClFN_5O_3$ 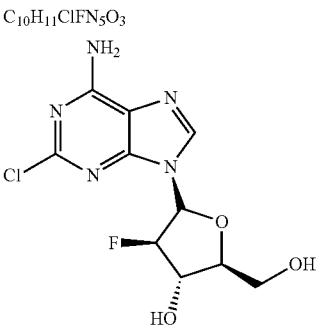 |

TABLE 1-continued

| Name/chemical name | Structure | |
|---|---|---|
| Anastrozole<br>2,2'-(5-(((1H-1,2,4-triazol-1-yl)methyl)-1,3-phenylene)bis(2-methylpropanenitrile) | $C_{17}H_{19}N_5$ | 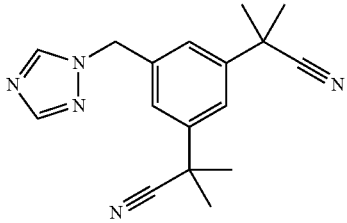 |
| Abiraterone<br>(3S,8R,9S,10R,13S,14S)-10,13-dimethyl-17-(pyridin-3-yl)-2,3,4,7,8,9,10,11,12,13,14,15-dodecahydro-1H-cyclopenta[a]phenanthren-3-ol. | $C_{24}H_{31}NO$ | 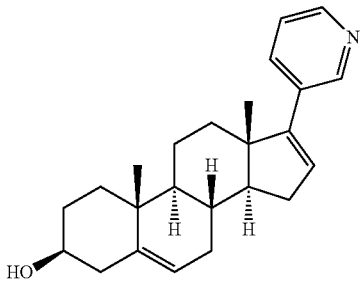 |
| Bexarotene<br>4-(1-(3,5,5,8,8-pentamethyl-5,6,7,8-tetrahydronaphthalen-2-yl)vinyl)benzoic acid | $C_{24}H_{28}O_2$ | 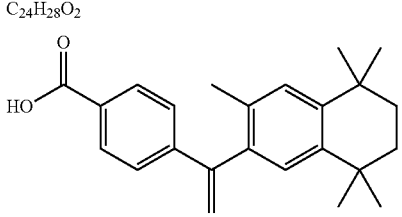 [SMILES: "C24H28O2" ; C=C(c1ccc(C(=O)O)cc1)c1cc2c(cc1C)C(C)(C)CCC2(C)C] |
| Bicalutamide<br>N-(4-cyano-3-(trifluoromethyl)phenyl)-3-((4-fluorophenyl)sulfonyl)-2-hydroxy-2-methylpropanamide | $C_{18}H_{14}F_4N_2O_4S$ | 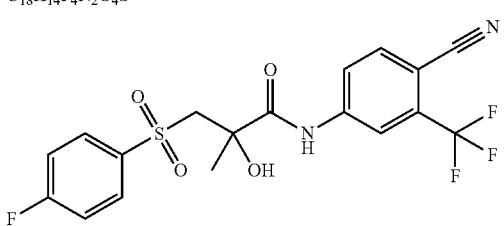 |
| Buserelin<br>1-(3-((1H-imidazol-4-yl)methyl)-6-((1H-indol-3-yl)methyl)-15-(tert-butoxymethyl)-21-(3-guanidinopropyl)-12-(4-hydroxybenzyl)-9-(hydroxymethyl)-18-isobutyl-1,4,7,10,13,16,19-heptaoxo-1-(5-oxopyrrolidin-2-yl)-2,5,8,11,14,17,20-heptaazadocosan-22-oyl)-N-ethylpyrrolidine-2-carboxamide | $C_{60}H_{86}N_{16}O_{13}$ | 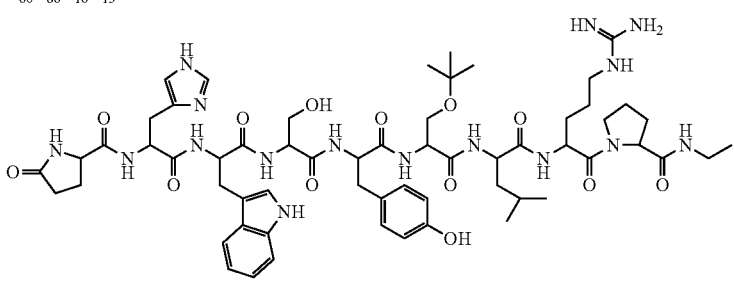 |

TABLE 1-continued

| Name/chemical name | Structure |
|---|---|
| Degarelix acetate<br>(S)-N-(4-((2S,5S,8R,11R,14R)-<br>2-(((R)-1-(((S)-1-(((S)-1-((S)-<br>2-(((R)-1-amino-1-oxopropan-2-<br>yl)carbamoyl)pyrrolidin-1-yl)-6-<br>(isopropylamino)-1-oxohexan-2-<br>yl)amino)-4-methyl-1-<br>oxopentan-2-yl)amino)-1-oxo-<br>3-(4-ureidophenyl)propan-2-yl)<br>carbamoyl)-11-(4-chlorobenzyl)-<br>5-(hydroxymethyl)-14-(naphthalen-<br>2-ylmethyl)-4,7,10,13,16-pentaoxo-<br>8-(pyridin-3-ylmethyl)-3,6,9,12,15-<br>pentaazaheptadecyl)phenyl)-2,6-<br>dioxohexahydropyrimidine-4-<br>carboxamide | $C_{84}H_{107}ClN_{18}O_{18}$ |
| Flutamide<br>N-(4-nitro-3-(trifluoromethyl)<br>phenyl)isobutyramide | $C_{11}H_{11}F_3N_2O_3$ |
| Goserelin acetate<br>N-(21-((1H-indol-3-yl)methyl)-<br>1-amino-12-(tert-butoxymethyl)-<br>6-(2-(2-carbamoylhydrazine-<br>carbonyl)pyrrolidine-1-carbonyl)-<br>15-(4-hydroxybenzyl)-18-<br>(hydroxymethyl)-25-(1H-imidazol-<br>4-yl)-1-imino-9-isobutyl-8,11,14,<br>17,20,23-hexaoxo-2,7,10,13,16,19,<br>22-heptaazapentacosan-24-yl)-5-<br>oxopyrrolidine-2-carboxamide<br>acetate | $C_{59}H_{84}N_{18}O_{14}$ |
| Deguelin<br>(7aS,13aS)-13,13a-Dihydro-9,10-<br>dimethoxy-3,3-dimethyl-3H-bis[1]<br>benzopyrano[3,4-b:6',5'-e]pyran-<br>7(7aH)-one | $C_{23}H_{22}O_6$ |
| Palomid 529<br>8-(1-hydroxyethyl)-2-methoxy-3-<br>((4-methoxybenzyl)oxy)-6H-<br>benzo[c]chromen-6-one | $C_{24}H_{22}O_6$ |

TABLE 1-continued

| Name/chemical name | Structure |
|---|---|
| Trametinib<br>N-[3-[3-Cyclopropyl-5-[(2-fluoro-4-iodophenyl)amino]-3,4,6,7-tetrahydro-6,8-dimethyl-2,4,7-trioxopyrido[4,3-d]pyrimidin-1(2H)-yl]phenyl]acetamide | $C_{26}H_{23}FIN_5O_4$ |
| Ceritinib (LDK378)<br>5-chloro-N2-(2-isopropoxy-5-methyl-4-(piperidin-4-yl)phenyl)-N4-(2-(isopropylsulfonyl)phenyl)pyrimidine-2,4-diamine | $C_{28}H_{36}ClN_5O_3S$ |
| Lanreotide acetate<br>(4S,7S,10S,13R,16S,19S)-13-((1H-indol-3-yl)methyl)-19-((R)-2-amino-3-(naphthalen-2-yl)propanamido)-N-((2S,3R)-1-amino-3-hydroxy-1-oxobutan-2-yl)-10-(4-aminobutyl)-16-(4-hydroxybenzyl)-7-isopropyl-6,9,12,15,18-pentaoxo-1,2-dithia-5,8,11,14,17-pentaazacycloicosane-4-carboxamide acetate | $C_{54}H_{69}N_{11}O_{10}S_2$ |
| Lenalidomide<br>3-(4-amino-1-oxoisoindolin-2-yl)piperidine-2,6-dione | $C_{13}H_{13}N_3O_3$ |

TABLE 1-continued

| Name/chemical name | Structure |
|---|---|
| Letrozole<br>4-[(4-cyanophenyl)-(1,2,4-triazol-1-yl)methyl]benzonitrile | $C_{17}H_{11}N_5$ |
| Megestrol acetate<br>(8R,9S,10R,13S,14S,17R)-17-acetyl-6,10,13-trimethyl-3-oxo-2,3,8,9,10,11,12,13,14,15,16,17-dodecahydro-1H-cyclopenta[a]phenanthren-17-yl acetate | $C_{24}H_{32}O_4$ |
| Mesna<br>sodium 2-mercaptoethanesulfonate | $C_2H_5NaO_3S_2$ |
| Octreotide<br>(4R,7S,10S,13R,16S,19R)-13-((1H-indol-3-yl)methyl)-19-((R)-2-amino-3-phenylpropanamido)-10-(4-aminobutyl)-16-benzyl-N-((2R,3R)-1,3-dihydroxybutan-2-yl)-7-(1-hydroxyethyl)-6,9,12,15,18-pentaoxo-1,2-dithia-5,8,11,14,17-pentaazacycloicosane-4-carboxamide acetate. | $C_{49}H_{66}N_{10}O_{10}S_2$ |

TABLE 1-continued

| Name/chemical name | Structure |
| --- | --- |
| Stilboestrol<br>(4R,7S,10S,13R,16S,19R)-13-<br>((1H-indol-3-yl)methyl)-19-((R)-<br>2-amino-3-phenylpropanamido)-<br>10-(4-aminobutyl)-16-benzyl-N-<br>((2R,3R)-1,3-dihydroxybutan-2-<br>yl)-7-(1-hydroxyethyl)-6,9,12,15,<br>18-pentaoxo-1,2-dithia-5,8,11,14,<br>17-pentaazacycloicosane-4-<br>carboxamide acetate. | $C_{49}H_{66}N_{10}O_{10}S_2$ |
| Tamoxifen citrate<br>(Z)-2-(4-(1,2-diphenylbut-1-en-1-<br>yl)phenoxy)-N,N-dimethylethanamine<br>2-hydroxypropane-1,2,3-tricarboxylate | $C_{26}H_{29}NO$ |
| Methotrexate<br>(S)-2-(4-(((2,4-diaminopteridin-6-<br>yl)methyl)(methyl)amino)benzamido)<br>pentanedioic acid. | $C_{20}H_{22}N_8O_5$ |

TABLE 1-continued

| Name/chemical name | Structure |
| --- | --- |
| Leucovorin Calcium<br>2-(4-(((S)-2-amino-5-formyl-4-oxo-1,4,5,6,7,8-hexahydropteridin-6-yl)(methyl)amino)benzamido)pentanedioic acid | $C_{20}H_{21}CaN_7O_7$ |
| Nolatrexed<br>2-Amino-6-methyl-5-(4-pyridyl-sulfanyl)quinazolin-4(3H)-one dihydrochloride | $C_{14}H_{12}N_4OS$ |
| Raltitrexed<br>(S)-2-(5-(methyl((2-methyl-4-oxo-1,4-dihydroquinazolin-6-yl)methyl)amino)thiophene-2-carboxamido)pentanedioic acid | $C_{21}H_{22}N_4O_6S$ |
| Anastrozole<br>2,2'-(5-((1H-1,2,4-triazol-1-yl)methyl)-1,3-phenylene)bis(2-methylpropanenitrile) | $C_{17}H_{19}N_5$ |
| Exemestane<br>(8R,9S,10R,13S,14S)-10,13-dimethyl-6-methylene-7,8,9,10,11,12,13,14,15,16-decahydro-3H-cyclopenta[a]phenanthrene-3,17(6H)-dione. | $C_{20}H_{24}O_2$ |

TABLE 1-continued

| Name/chemical name | Structure |
|---|---|
| Letrozole<br>4-[(4-cyanophenyl)-(1,2,4-triazol-1-yl)methyl]benzonitrile | $C_{17}H_{11}N_5$ 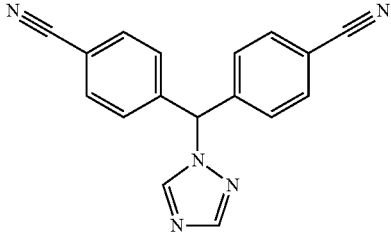 |
| KU-55933<br>2-morpholino-6-(thianthren-1-yl)-4H-pyran-4-one | $C_{21}H_{17}NO_3S_2$ 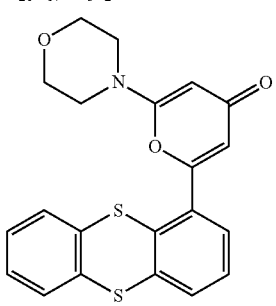 |
| Alisertib<br>4-((9-chloro-7-(2-fluoro-6-methoxyphenyl)-5H-benzo[c]pyrimido[4,5-e]azepin-2-yl)amino)-2-methoxybenzoic acid | $C_{27}H_{20}ClFN_4O_4$ 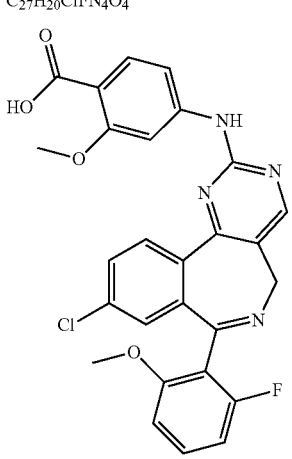 |
| Barasertib<br>(AZD1152)<br>2-(ethyl(3-(4-(5-(2-(3-fluorophenylamino)-2-oxoethyl)-1H-pyrazol-3-ylamino)quinazolin-7-yloxy)propyl)amino)ethyl dihydrogen phosphate. | $C_{26}H_{31}FN_7O_6P$ 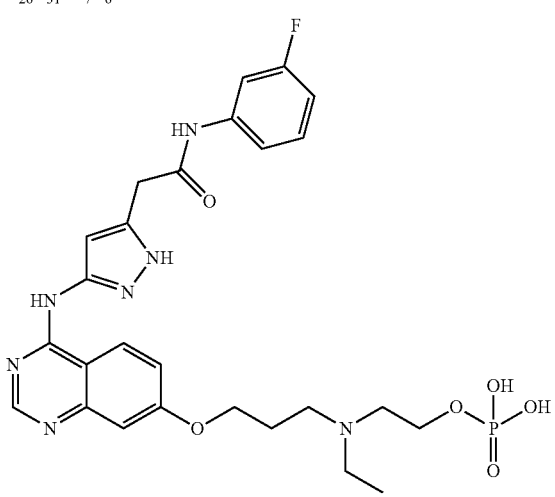 |

TABLE 1-continued

| Name/chemical name | Structure |
|---|---|
| CYC116<br>4-methyl-5-(2-(4-morpholinophenyl-amino)pyrimidin-4-yl)thiazol-2-amine | $C_{18}H_{20}N_6OS$ |
| INH-13<br>N-(5-((7-(2-hydroxy-3-(piperidin-1-yl)propoxy)-6-methoxyquinazolin-4-yl)amino)pyrimidin-2-yl) benzamide | $C_{28}H_{31}N_7O_4$ |
| Hesperadin<br>(Z)-N-(2-oxo-3-(phenyl((4-(piperidin-1-ylmethyl)phenyl)amino)methylene) indolin-5-yl)ethanesulfonamide | $C_{29}H_{32}N_4O_3S$ |
| OM-137<br>(E)-2-amino-N'-(4-hydroxy-3-methoxybenzylidene)-4-methylthiazole-5-carbohydrazide | $C_{13}H_{14}N_4O_3S$ |

TABLE 1-continued

| Name/chemical name | Structure |
|---|---|
| SNS-314<br>N-(3-Chlorophenyl)-N'-[5-[2-(thieno[3,2-d]pyrimidin-4-ylamino)ethyl]-2-thiazolyl]urea | $C_{18}H_{15}ClN_6OS_2$ |
| Obatoclax<br>(Z)-2-(2-((3,5-dimethyl-1H-pyrrol-2-yl)methylene)-3-methoxy-2H-pyrrol-5-yl)-1H-indole methanesulfonate | $C_{20}H_{19}N_3O$ |
| AT-101<br>1,1',6,6',7,7'-hexahydroxy-5,5'-diisopropyl-3,3'-dimethyl-[2,2'-binaphthalene]-8,8'-dicarbaldehyde | $C_{30}H_{30}O_8$ |
| Aclarubicin Hydrochloride<br>(1R,2R,4S)-methyl 4-(((2R,5S,6S)-4-(dimethylamino)-5-(((2S,4S,5S,6S)-4-hydroxy-6-methyl-5-(((2R,6S)-6-methyl-5-oxotetrahydro-2H-pyran-2-yl)oxy)tetrahydro-2H-pyran-2-yl)oxy)-6-methyltetrahydro-2H-pyran-2-yl)oxy)-2-ethyl-2,5,7-trihydroxy-6,11-dioxo-1,2,3,4,6,11-hexahydrotetracene-1-carboxylate hydrochloride | $C_{42}H_{53}NO_1$ |

TABLE 1-continued

| Name/chemical name | Structure |
| --- | --- |
| Amrubicin<br>(7S,9S)-9-acetyl-9-amino-7-<br>(((2S,4S,5R)-4,5-dihydroxy-<br>tetrahydro-2H-pyran-2-yl)oxy)-<br>6,11-dihydroxy-7,8,9,10-tetra-<br>hydrotetracene-5,12-dione<br>hydrochloride | $C_{25}H_{25}NO_9$ 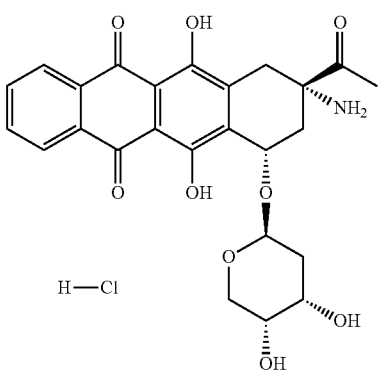 |
| Annamycin<br>(7S,9S)-7-(((2R,3R,4R,5R,6S)-<br>4,5-dihydroxy-3-iodo-6-methyl-<br>tetrahydro-2H-pyran-2-yl)oxy)-<br>6,9,11-trihydroxy-9-(2-hydroxy-<br>acetyl)-7,8,9,10-tetrahydrotetra-<br>cene-5,12-dione | $C_{26}H_{25}IO_{11}$ 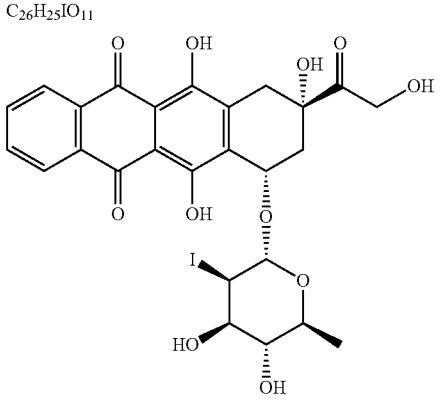 |
| Actinomycin D (Dactinomycin)<br>2-amino-N1,N9-bis(6,13-diiso-<br>propyl-2,5,9-trimethyl-1,4,7,11,<br>14-pentaoxohexadecahydro-1H-<br>pyrrolo[2,1-i][1,4,7,10,13]oxatetra-<br>azacyclohexadecin-10-yl)-4,6-<br>dimethyl-3-oxo-3H-phenoxazine-<br>1,9-dicarboxamide | $C_{62}H_{86}N_{12}O_{16}$ 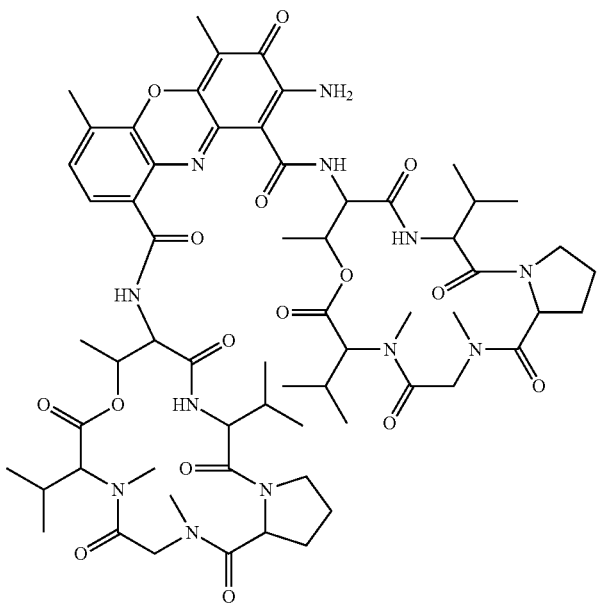 |

TABLE 1-continued

| Name/chemical name | Structure |
| --- | --- |
| Aldoxorubicin (INNO-206) (E)-N'-(1-((2S,4S)-4-(((2R,4S,5S, 6S)-4-amino-5-hydroxy-6-methyl-tetrahydro-2H-pyran-2-yl)oxy)-2,5,12-trihydroxy-7-methoxy-6,11-dioxo-1,2,3,4,6,11-hexahydrotetracen-2-yl)-2-hydroxy-ethylidene)-6-(2,5-dioxo-2,5-dihydro-1H-pyrrol-1-yl)hexane-hydrazide hydrochloride | $C_{37}H_{42}N_4O_{13} \cdot HCl$ |
| GPX100 (8R,10S)-10-(((2S,4S,5R,6S)-4-amino-5-hydroxy-6-methyltetrahydro-2H-pyran-2-yl)oxy)-6,8,11-trihydroxy-8-(2-hydroxyethyl)-1-methoxy-7,8,9,10-tetrahydrotetracene-5,12-dione | $C_{27}H_{31}NO_{10}$ |
| Idarubicin hydrochloride (7S,9S)-9-acetyl-7-(((2R,4S,5S, 6S)-4-amino-5-hydroxy-6-methyl-tetrahydro-2H-pyran-2-yl)oxy)-6,9,11-trihydroxy-7,8,9,10-tetrahydrotetracene-5,12-dione hydrochloride | $C_{26}H_{27}NO_9$ |
| Ellipticine 5,11-dimethyl-6H-pyrido[4,3-b]carbazole | $C_{17}H_{14}N_2$ |

TABLE 1-continued

| Name/chemical name | Structure |
|---|---|
| Quarfloxin<br>5-fluoro-N-(2-((S)-1-methyl-pyrrolidin-2-yl)ethyl)-3-oxo-6-((R)-3-(pyrazin-2-yl)pyrrolidin-1-yl)-3H-benzo[b]pyrido[3,2,1-kl]phenoxazine-2-carboxamide. | $C_{35}H_{33}FN_6O_3$ |
| EPZ004777<br>1-(3-(((((2R,3S,4R,5R)-5-(4-amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea | $C_{28}H_{41}N_7O_4$ |
| Afatinib<br>(S,E)-N-(4-(3-chloro-4-fluoro-phenylamino)-7-((tetrahydrofuran-3-yl)methyl)quinazolin-6-yl)-4-(dimethylamino)but-2-enamide. | $C_{25}H_{27}ClFN_5O_2$ |
| Erlotinib hydrochloride<br>N-(3-Ethynylphenyl)-6,7-bis(2-methoxyethoxy)-4-quinazolin-amine Monohydrochloride. | $C_{22}H_{24}ClN_3O_4$ |

TABLE 1-continued

| Name/chemical name | Structure |
|---|---|
| Dacomitinib<br>(E)-N-(4-((3-chloro-4-fluoro-phenyl)amino)-7-methoxy-quinazolin-6-yl)-4-(piperidin-1-yl)but-2-enamide | $C_{24}H_{25}ClFN_5O_2$ |
| TAK-285<br>N-(2-(4-((3-chloro-4-(3-(trifluoromethyl)phenoxy)phenyl)amino)-5H-pyrrolo[3,2-d]pyrimidin-5-yl)ethyl)-3-hydroxy-3-methylbutanamid | $C_{26}H_{25}ClF_3N_5O_3$ |
| Vandetanib<br>N-(4-bromo-2-fluorophenyl)-6-methoxy-7-[(1-methylpiperidin-4-yl)methoxy]quinazolin-4-amine | $C_{22}H_{24}BrFN_4O_2$ |
| Defactinib (VS-6063)<br>N-methyl-4-((4-(((3-(N-methyl-methylsulfonamido)pyrazin-2-yl)methyl)amino)-5-(trifluoro-methyl)pyrimidin-2-yl)amino)benzamide | $C_{20}H_{21}F_3N_8O_3S$ |

TABLE 1-continued

| Name/chemical name | Structure |
|---|---|
| 3-deazaneplanocin A (1S,2R,5R)-5-(4-amino-1H-imidazo[4,5-c]pyridin-1-yl)-3-(hydroxymethyl)cyclopent-3-ene-1,2-diol hydrochloride | $C_{12}H_{14}N_4O_3$ 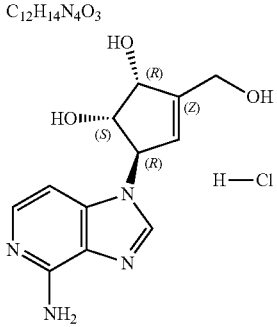 |
| EPZ-005687 1-cyclopentyl-N-((4,6-dimethyl-2-oxo-1,2-dihydropyridin-3-yl)methyl)-6-(4-(morpholinomethyl)phenyl)-1H-indazole-4-carboxamide. | $C_{32}H_{37}N_5O_3$ 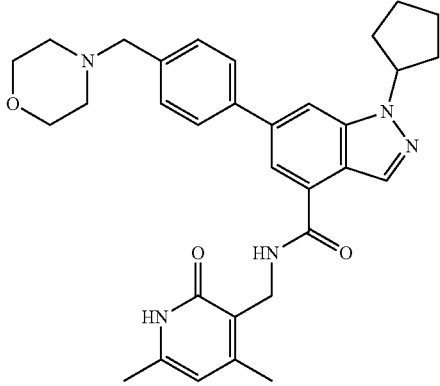 |
| GSK126 (S)-1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide | $C_{31}H_{38}N_6O_2$ 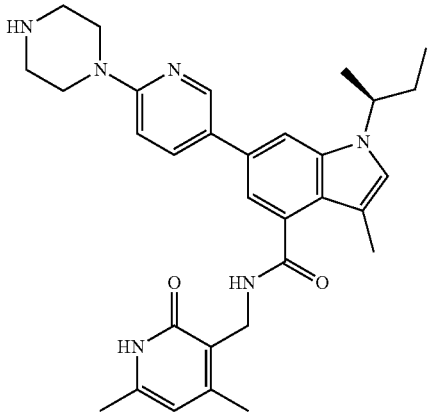 |

TABLE 1-continued

| Name/chemical name | Structure |
|---|---|
| UNC-1999<br>1-isopropyl-6-(6-(4-isopropyl-piperazin-1-yl)pyridin-3-yl)-N-((6-methyl-2-oxo-4-propyl-1,2-dihydropyridin-3-yl)methyl)-1H-indazole-4-carboxamide | $C_{33}H_{43}N_7O_2$<br>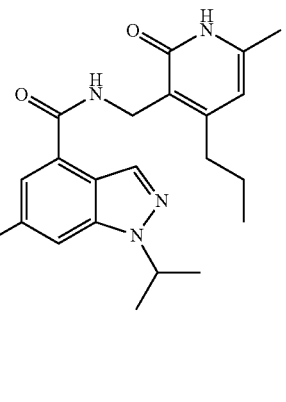 |
| Avagacestat (BMS-708163)<br>(R)-2-(4-chloro-N-(2-fluoro-4-(1,2,4-oxadiazol-3-yl)benzyl)phenylsulfonamido)-5,5,5-trifluoropentanamide | $C_{20}H_{17}ClF_4N_4O_4S$<br>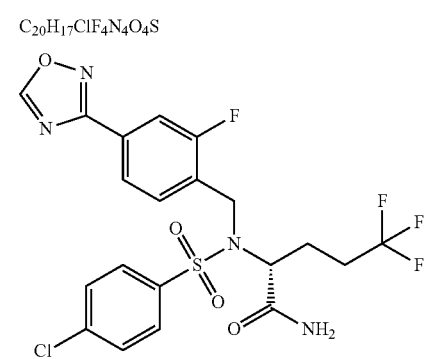 [SMILES: "C20H17ClF4N4O4S" ; NC(=O)[C@@H](CCC(F)(F)F)N(Cc1ccc(-c2ncon2)cc1F)S(=O)(=O)c1ccc(Cl)cc1] |
| BMS-299897<br>(R)-4-(2-(1-(4-chloro-N-(2,5-difluorophenyl)phenyl-sulfonamido)ethyl)-5-fluorophenyl)butanoic acid | $C_{24}H_{21}ClF_3NO_4S$<br>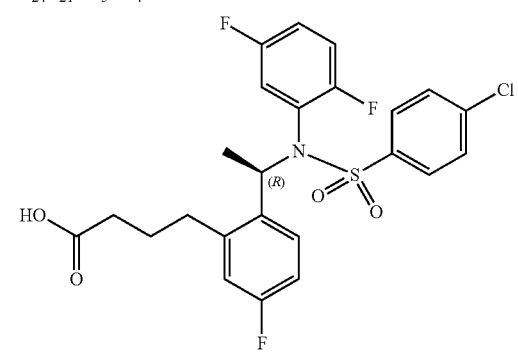 |
| ELND007<br>(R)-4-cyclopropyl-8-fluoro-5-((6-(trifluoromethyl)pyridin-3-yl)sulfonyl)-4,5-dihydro-2H-pyrazolo[4,3-c]quinoline | $C_{19}H_{14}F_4N_4O_2S$<br>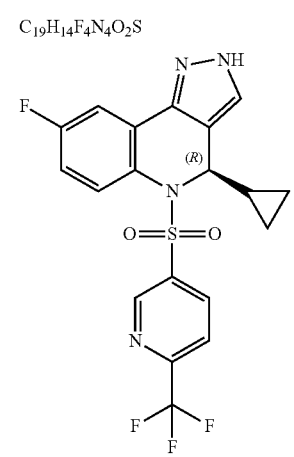 |

TABLE 1-continued

| Name/chemical name | Structure |
| --- | --- |
| L685458<br>tert-butyl ((2S,3R,5R)-6-(((S)-1-(((S)-1-amino-1-oxo-3-phenyl-propan-2-yl)amino)-4-methyl-1-oxopentan-2-yl)amino)-5-benzyl-3-hydroxy-6-oxo-1-phenylhexan-2-yl)carbamat | $C_{39}H_{52}N_4O_6$ |
| PF-03084014<br>(S)-2-(((S)-6,8-difluoro-1,2,3,4-tetrahydronaphthalen-2-yl)amino)-N-(1-(2-methyl-1-(neopentyl-amino)propan-2-yl)-1H-imidazol-4-yl)pentanamide | $C_{27}H_{41}F_2N_5O$ |
| RO4929097<br>(S)-2,2-dimethyl-N1-(6-oxo-6,7-dihydro-5H-dibenzo[b,d]azepin-7-yl)-N3-(2,2,3,3,3-pentafluoropropyl)malonamide | $C_{22}H_{20}F_5N_3O_3$ |
| Semagacestat<br>(S)-2-hydroxy-3-methyl-N-((S)-1-(((S)-3-methyl-2-oxo-2,3,4,5-tetrahydro-1H-benzo[d]azepin-1-yl)amino)-1-oxopropan-2-yl)butanamide | $C_{19}H_{27}N_3O_4$ |

TABLE 1-continued

| Name/chemical name | Structure |
| --- | --- |
| Aroplatin<br>cyclohexane-1,2-diamine; 7,7-dimethyloctanoate; platinum(+2) | $C_{26}H_{50}N_2O_4Pt$ |
| Miriplatin<br>(1R,2R)-cyclohexane-1,2-diamine; platinum(2+); tetradecanoate; hydrate | $C_{34}H_{70}N_2O_5Pt$ |
| Iproplatin<br>cis,trans,cis-Dichlorodi-hydroxobis(isopropylamine) platinum | $C_6H_{20}Cl_2N_2O_2Pt$ |
| Vinorelbine tartrate<br>(3aR,3a1R,4R,5S,5aR,10bR)-methyl 4-acetoxy-3a-ethyl-9-((2R,8S)-4-ethyl-8-(methoxy-carbonyl)-1,3,6,7,8,9-hexahydro-2,6-methanoazecino[4,3-b]indol-8-yl)-5-hydroxy-8-methoxy-6-methyl-3a,3a1,4,5,5a,6,11,12-octahydro-1H-indolizino[8,1-cd]carbazole-5-carboxylate bis((2R,3R)-2,3-dihydroxysuccinate) | $C_{53}H_{66}N_4O_{20}$ |

TABLE 1-continued

| Name/chemical name | Structure |
|---|---|
| Vindesine (3S,5S,7S,9S)-methyl 9-((3aR,3a1R,4R,5S,5aR,10bR)-5-carbamoyl-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1]azacyclo-undecino[5,4-b]indole-9-carboxylate | $C_{43}H_{55}N_5O_7$ 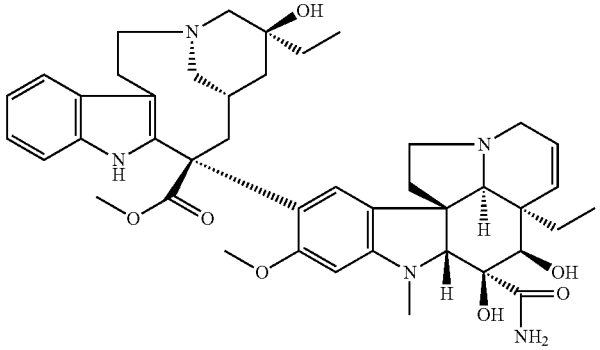 |
| Vinflunine (3aR,3a1R,4R,5S,5aR,10bR)-methyl 4-acetoxy-9-((2S,4S,6S,8S)-4-(1,1-difluoroethyl)-8-(methoxycarbonyl)-1,3,4,5,6,7,8,9-octahydro-2,6-methanoazecino[4,3-b]indol-8-yl)-3a-ethyl-5-hydroxy-8-methoxy-6-methyl-3a,3a1,4,5,5a,6,11,12-octahydro-1H-indolizino[8,1-cd]carbazole-5-carboxylate | $C_{45}H_{54}F_2N_4O_8$ 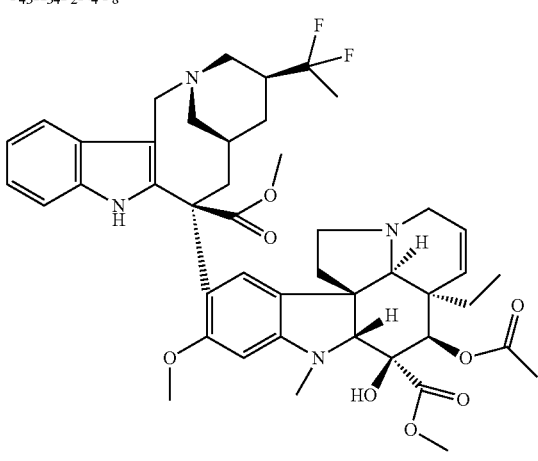 |

Another set of embodiments is generally directed to a device for irreversibly confining a charged compound in an internal region of at least one target cell, including: a fluid containing first target cells and second non-target cells, wherein the first target cells include cytosols having a basic pH property and wherein the second non-target cells include cytosols having a neutral or acidic pH property; and, an uncharged compound adapted to freely pass into the cytosols of the first target cells and the second non-target cells, wherein the uncharged compound is adapted to be converted at a basic pH into at least one charged compound adapted to remain in the cytosols of the first target cells.

In one aspect, the first target cells are selected from circulating tumor cells, circulating fetal cells, or stem cells, or other cells as described herein. In another aspect, the stem cells are realized as fetal stem cells, cord blood stem cells, embryonic stem cells, adult stem cells, tissue-specific stem cells, and induced pluripotent stem cells. In another aspect of the device, the at least one charged compound is adapted to have a detectable quality. In another aspect of the device, the detectable quality is selected from fluorescence, radio-activity or nuclear particle release (e.g., detection of gamma rays, beta particles, and/or alpha particles, etc.), color changes, energy release, electromagnetic radiation release, chemical reactivity, biological reactivity, chemical polarity, solubility changes, etc.

In some cases, the cells may be determined and/or sorted within the device, e.g., as previously discussed. For example, the cells may be determined and/or sorted using a cell cytometer, a fluorescence microscope, a flow cytometer, a cell sorting machine, or the like.

In another aspect, the target cells may be present in a subject, e.g., in vivo. For instance, in one set of embodiments, the target cells are cancer cells. By administering, to a subject, compounds such as those discussed herein, cancer cells and non-cancerous cells may be distinguished in some fashion, e.g., using, for example, radioactivity, color, fluorescence, energy release, chemical reactivity, biological reactivity, chemical polarity, or solubility, e.g., using an appropriate signaling entity. In some cases, systems and methods such as those described herein may be used to determine target cells of interest, and then the target cells of interest (or the non-target cells) may be removed based on the determination. The subject may be, e.g., human or non-human.

In some cases, for example, the target cells may be located in a margin of a tumor, e.g., a location or space where healthy and cancer cells meet. In some embodiments, after administration of compound such as those discussed herein, the target cells and the non-target cells are subjected to PET-CT. In certain embodiments, there is a step of immunostaining with organ-specific antibodies for investigation of localization of a tumor.

Thus, certain embodiments are generally directed towards tumors or the like. The instant embodiment may be used in vivo for determining and/or treating tumors, e.g., by finding a boundary between cancerous and healthy cells. In situ CT or the like may allow, for example, for detection of target cancer cells to allow a doctor to remove all problematic cells and not leave cancer cells in an area generally considered to be clean of cancer cells.

Each of the following is incorporated herein by reference in its entirety: U.S. patent application Ser. No. 14/225,512, filed Mar. 26, 2014, entitled "Devices and Methods for Determining and/or Isolating Cells Such as Circulating Cancer or Fetal Cells"; U.S. patent application Ser. No. 14/103,170, filed Dec. 11, 2013, entitled "Devices and Methods for Determining and/or Isolating Cells Such as Circulating Cancer or Fetal Cells"; U.S. patent application Ser. No. 14/312,875, filed Jun. 24, 2014, entitled "Devices and Methods for Determining and/or Isolating Cells Such as Circulating Cancer or Fetal Cells"; and U.S. Pat. Apl. Ser. No. 62/058,884, filed Oct. 2, 2014, entitled "Devices and Methods for Retaining Charged Molecules."

The following examples are intended to illustrate certain embodiments of the present invention, but do not exemplify the full scope of the invention.

Example 1

In this example, it was demonstrated that human cancer cells in peripheral blood could be identified and isolated, exploiting their preferential maintenance of a more basic pH level than their surrounding media or other blood borne cells. In this example, a pH-sensitive fluorescent dye was added to carcinoma cells and normal blood cells, and the fluorescent signal corresponding to the dye internalized in cells with more basic pH was used for detection, counting, and potential separation in a flow cytometer or sorter machine. In the present example, a fluorescence-activated cell sorting (FACS) system was used. The sorted cells were presented in a well-preserved state, which allowed following cytopathological and genetic analyses.

HT29 cells (human colon carcinoma) were obtained from ATCC, and 2 ml of whole normal human blood was collected from a healthy volunteer. Blood was processed within 2 hours of collection and examined by a BD FACSARIA II SORP sorter machine following incubation with a fluorescent dye (BCECF AM), and also in certain experiments, also without such an incubation step. Blood was processed with RBC lysis and also without RBC lysis steps in different experiments. Finally, blood was mixed with colon carcinoma cells (HT29) and incubated with BCECF AM in some experiments as described herein.

1 mg of BCECF AM (Invitrogen) was dissolved in 1 ml of DMSO and 10 aliquots were prepared. One aliquot was dissolved in 10 ml of Hank's balanced salt solution in order to make a working solution (0.016 mM). The working solution of BCECF AM was added to the samples (2 ml of BCECF AM to 2 ml of sample), and incubated in room temperature for one hour. Lysis of the RBCs then was performed, after staining by fluorescent dye (BCECF AM) by adding to the sample 1 ml of RBC lysis buffer (BioLegend) dissolved in 10 ml of distillate water and incubated for 10 minutes in room temperature. PBS was then added up to 50 ml total volume, followed by centrifugation (2000 rpm for 10 min) and removal of the supernatant. 2 ml of each sample was introduced for analysis by a BD FACSARIA II SORP machine and the data was analyzed using the BD FACSARIA II SORP system software. HT29 cells were further sorted and isolated in a tube containing 70% ethanol.

Figure 7A:
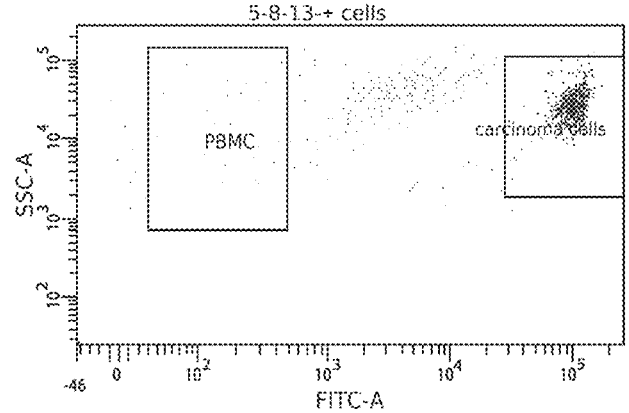
FIGS. 7A-7H show experiments using HT29 cells, in accordance with certain embodiments of the invention.
Figure 7B:
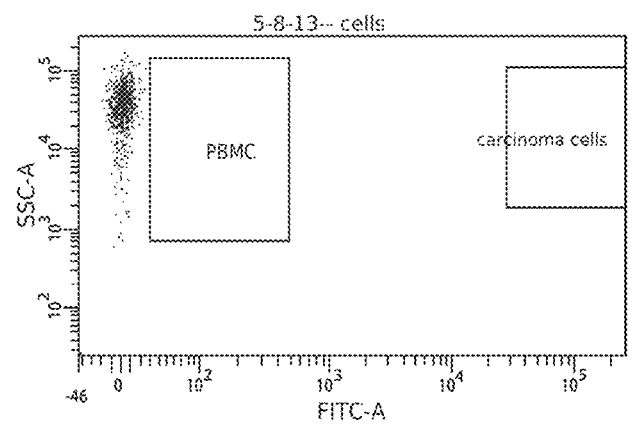
Figure 7C:
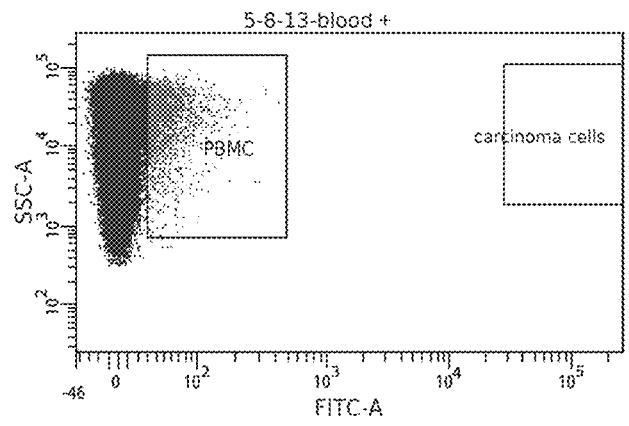
Figure 7D:
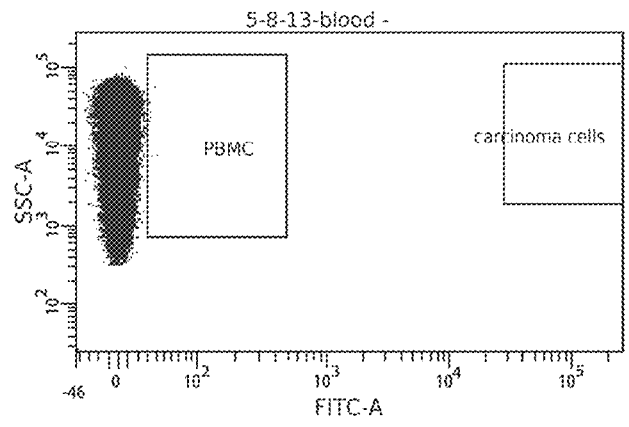
Figure 7E:
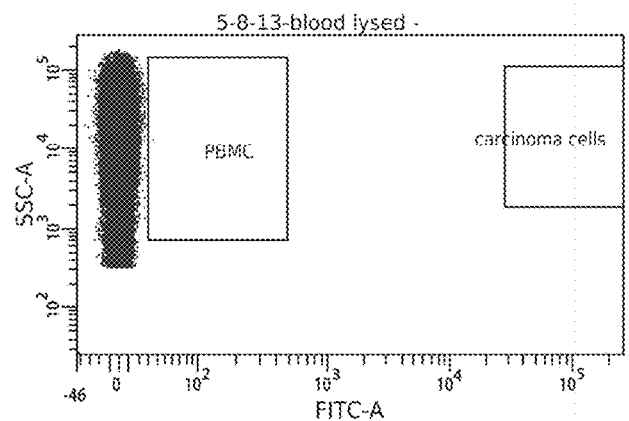
Figure 7F:
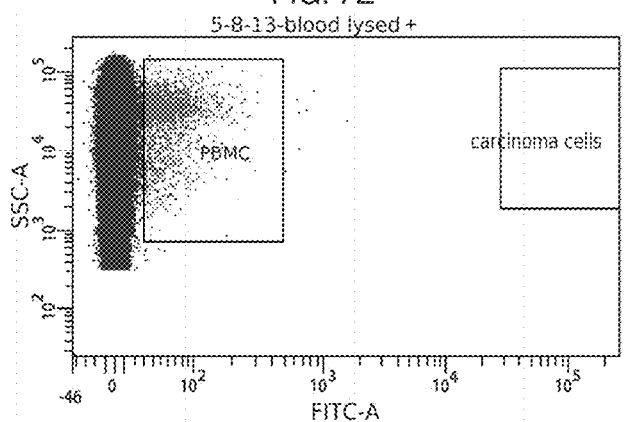
Figure 7G:
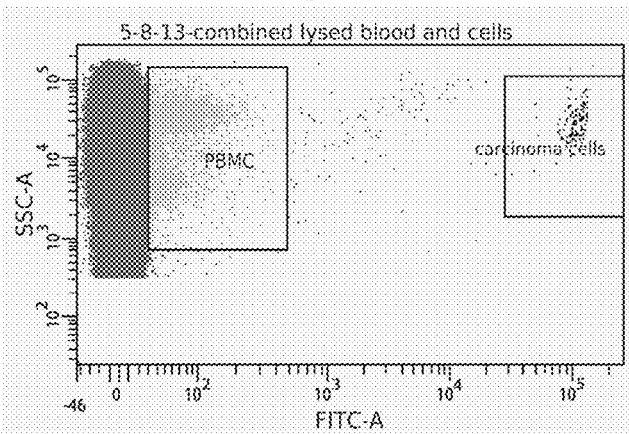
Figure 7H:
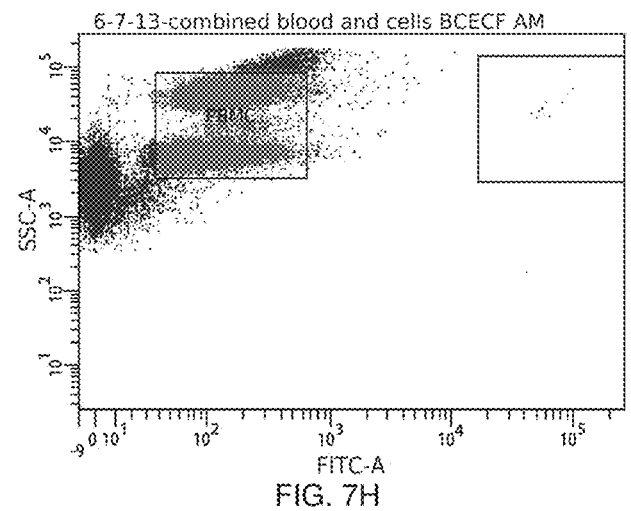

FIG. 7A shows HT29 cells alone, incubated with BCECF AM (0.016 M) for one hour at room temperature, showing strong fluorescence of HT29 cells. In this and the following figures showing data obtained from the FACS software, the abscissa (FITC-A) always refers to the strength of the fluorescent signal obtained from the cell, and the ordinate (SSC-A) is an area parameter useful for rejection of doublet cells. Both axes are logarithmic. FIG. 7B shows HT29 cells alone, without adding of BCECF AM, showing weak fluorescence of HT29 cells. FIG. 7C shows blood without lysis and incubated with BCECF AM (0.016 mM) for one hour at room temperature, showing a weak fluorescent signal. FIG. 7D shows blood without lysis and without adding of BCECF AM, showing almost no fluorescence. FIG. 7E shows blood with RBC lysis and without adding of BCECF AM, showing almost no fluorescence. FIG. 7F shows blood alone, with RBC lysis and incubation with BCECF AM (0.016 mM) for one hour at room temperature, showing a weak fluorescent signal. FIG. 7G shows a mixture of blood with RBC lysis and HT29 cells incubated with BCECF AM (0.016 mM) for one hour at room temperature. HT29 cells show much stronger fluorescent signal then blood cells, and could then be detected and sorted in the FACS sorter machine. FIG. 7H demonstrates reproducibility by repeating the procedures of this example with a separate, independent sample.

This example demonstrates: (1) isolated carcinoma cells showed strong fluorescent signal when incubated with a basic pH-sensitive fluorescent dye (FIG. 7A); (2) isolated carcinoma cells did not show strong fluorescent signal naturally without being incubated with same dye (FIG. 7B); (3) normal circulating blood cells did not show strong fluorescent signal when incubated with the same dye (FIG. 7C); (4) normal circulating blood cells did not show strong fluorescent signal without being incubated with same dye (FIG. 7D); (5) normal circulating blood in which red blood cells (RBC) were lysed did not show strong fluorescent signal without being incubated with same dye (FIG. 7E; (6) normal circulating blood in which RBC were lysed did not show strong fluorescent signal after being incubated with same dye (FIG. 7F); (7) a mixture of normal circulating blood with lysed RBC with isolated carcinoma cells could be separated in a FACS sorter after incubation with a basic pH-sensitive fluorescent dye (FIG. 7G); and (8) repeatability of these experiments produced similar results (FIG. 7H).

Example 2

In this example, it was demonstrated that embryonic cells in peripheral blood could be identified and isolated, exploiting their preferential maintenance of a more basic pH level than their surrounding media or other blood borne cells. In this example, a pH-sensitive fluorescent dye was added to embryonic cells and normal blood cells, and the fluorescent signal corresponding to the dye internalized in cells with more basic pH was used for detection, counting, and potential separation in a flow cytometer or sorter machine. In the present example, a fluorescence-activated cell sorting (FACS) system was used. The sorted cells were presented in a well-preserved state, which allowed following cytopathological and genetic analyses.

Embryonic mouse hypothalamic cells were obtained from Cellutions Biosystems, Inc., and 2 ml of whole blood was collected from a healthy human volunteer. The blood was mixed with embryonic cells. Blood was processed within 2 hours of collection and examined by a BD FACSARIA II SORP machine following incubation of a fluorescent dye: BCECF AM, and also in certain experiments, without such incubation step.

1 mg of BCECF AM (Invitrogen) was dissolved in 1 ml of DMSO and 10 aliquots were prepared. One aliquot was then dissolved in 10 ml of Hank's balanced salt solution in order to make a working solution with concentration of 0.016 mM. The working solution was added of BCECF AM to the samples (2 ml of BCECF AM to 2 ml of sample), and incubated at room temperature for one hour. Lysis of the RBCs then was performed, after staining by fluorescent dye (BCECF AM), by adding to the sample 1 ml of RBC lysis buffer (BioLegend) dissolved in 10 ml of distillate water and incubated for 10 minutes at room temperature. PBS was then added to result in up to 50 ml of total volume, followed by centrifugation (2000 rpm for 10 min) and removal of the supernatant.

2 ml of each sample was then introduced for analysis by a BD FACSARIA II SORP machine and the data analyzed by the BD FACSARIA II SORP system software. Embryonic cells were further sorted and isolated in a tube containing 70% ethanol. Isolated embryonic cells were placed on an optical microscope slide and viewed at 40× (FIG. 8C). For comparison, white blood cells were also viewed at 40× (FIG. 8D).

Figure 8A:
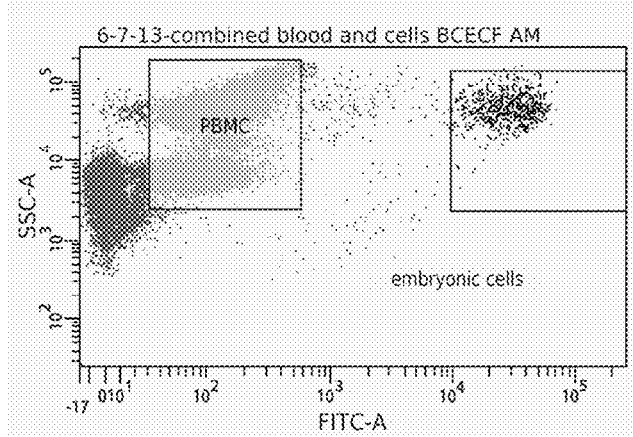
FIGS. 8A-8D show experiments using lysed blood mixed with embryonic cells, according to some embodiments of the invention.
Figure 8B:
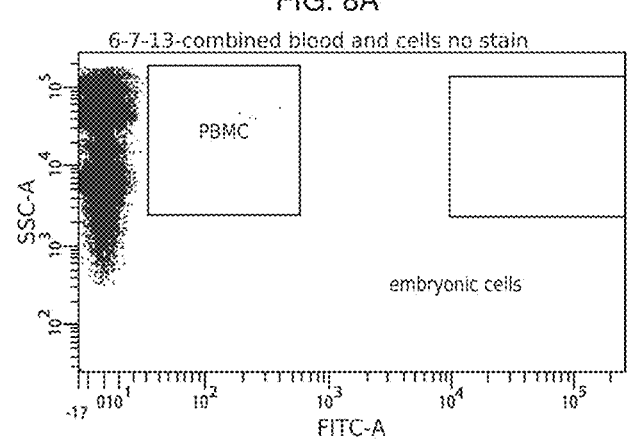
Figure 8C:
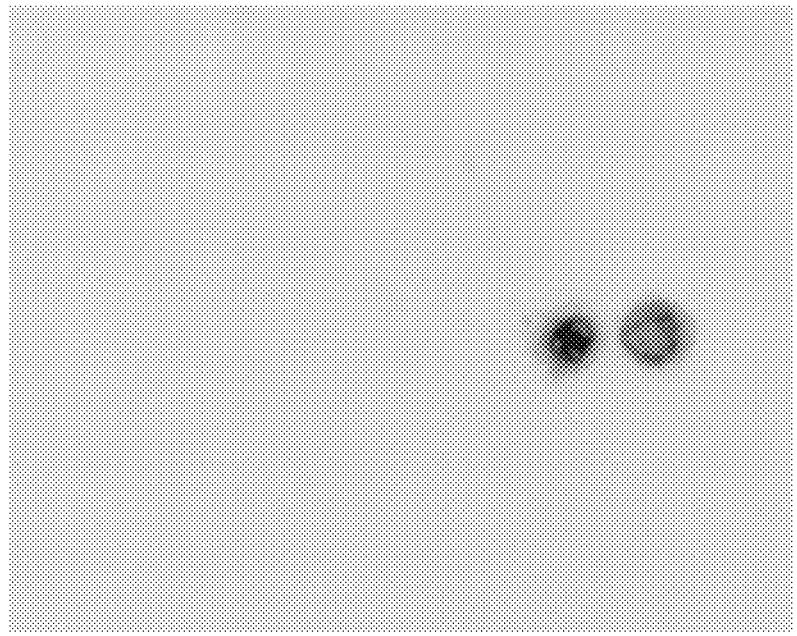
Figure 8D:
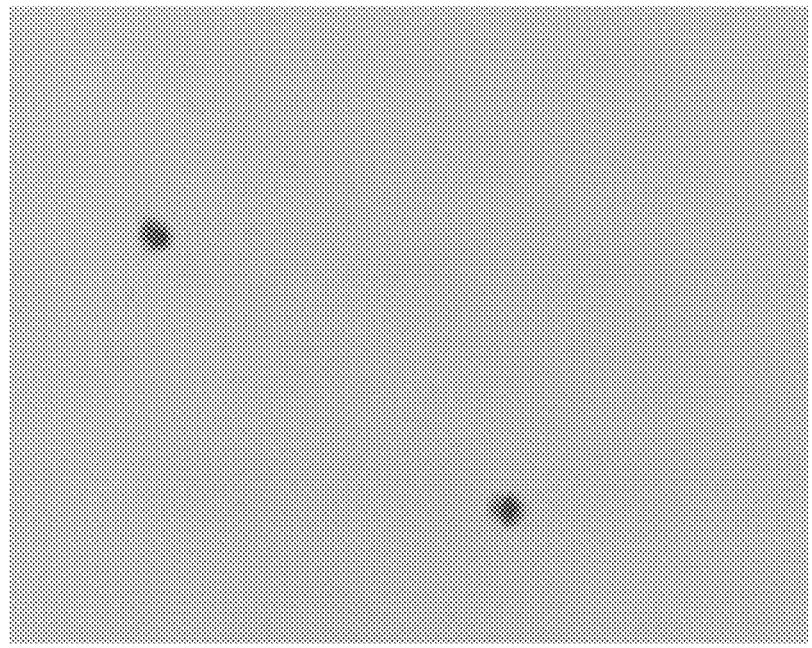

FIG. 8A shows lysed blood mixed with embryonic cells incubated with BCECF AM (0.016 mM) for one hour at room temperature, demonstrating that embryonic cells have much stronger fluorescence than other blood cells, which could be exploited for detection, counting, and/or sorting. FIG. 8B shows lysed blood mixed with embryonic cells without adding of BCECF AM, showing almost no fluorescence. FIG. 8C shows embryonic cells isolated using techniques of the present invention viewed at 40× magnification. FIG. 8D shows white blood cells viewed at 40× magnification for comparison purposes.

This example demonstrated: (1) a mixture of normal circulating blood with lysed RBC with embryonic cells could be separated in a FACS sorter after incubation with a basic pH-sensitive fluorescent dye (FIG. 8A); and (2) a mixture of normal circulating blood in which RBC were lysed with embryonic cells did not show strong fluorescent signal without being incubated with same dye (FIG. 8B).

Example 3

In this example, it was demonstrated that circulating cancer cells in peripheral blood obtained from a cancer patient could be identified and isolated, exploiting their preferential maintenance of a more basic pH level than their surrounding media or other blood borne cells. In this example, a pH-sensitive fluorescent dye was added to a sample of a cancer patient blood, and the fluorescent signal corresponding to the dye internalized in cells with more basic pH was used for detection, counting, and potential separation in a flow cytometer or sorter machine. In the present example, a fluorescence-activated cell sorting (FACS) system was used. The sorted cells are presented in a well-preserved state, enabling subsequent cytopathological and genetic analyses.

2 ml of whole blood was collected from a cancer patient with prior diagnosis of stage 4 Hodgkin lymphoma, following consent using an informed consent declaration. 2 ml of whole normal human blood was also collected from a healthy volunteer. Blood was processed within 2 hours of collection and examined by a BD FACSARIA II SORP machine following incubation of a fluorescent dye (BCECF AM).

1 mg of BCECF AM (Invitrogen) was dissolved in 1 ml of DMSO and 10 aliquots were prepared. One aliquot was dissolved in 10 ml of Hank's balanced salt solution in order to make a working solution (0.016 mM). The working solution of BCECF AM was added to the samples (2 ml of BCECF AM to 2 ml of sample) and incubated at room temperature for one hour. Lysis of the RBCs then was performed following staining by fluorescent dye (BCECF AM) by adding to the sample 1 ml of RBC lysis buffer (BioLegend) dissolved in 10 ml of distillate water and incubated for 10 minutes at room temperature. PBS was then added to result in up to 50 ml total volume, followed by centrifugation (2000 rpm for 10 min) and removal of the supernatant.

2 ml of each sample was introduced for analysis by a BD FACSARIA II SORP machine and the data analyzed by the system BD FACSARIA II SORP software. Hodgkin lymphoma cells were further sorted, stained by H&E stain (hematoxylin and eosin stain), and isolated on the microscope glass slide and viewed at 40× (FIG. 9C).

Figure 9A:
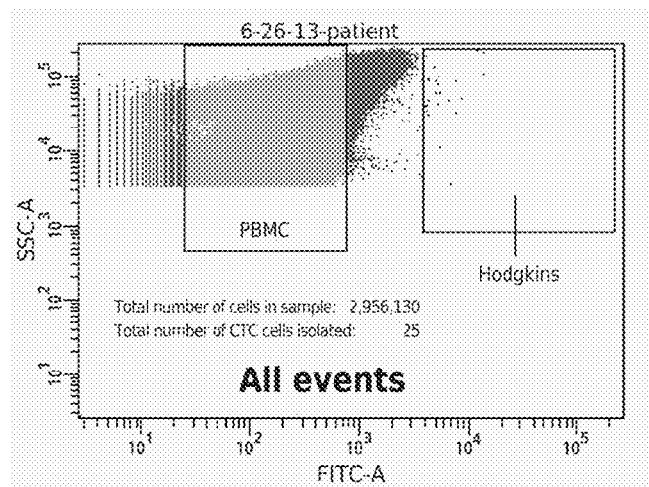
FIGS. 9A-9C show circulating cancer cells isolated in accordance with certain embodiments of the invention.
Figure 9B:
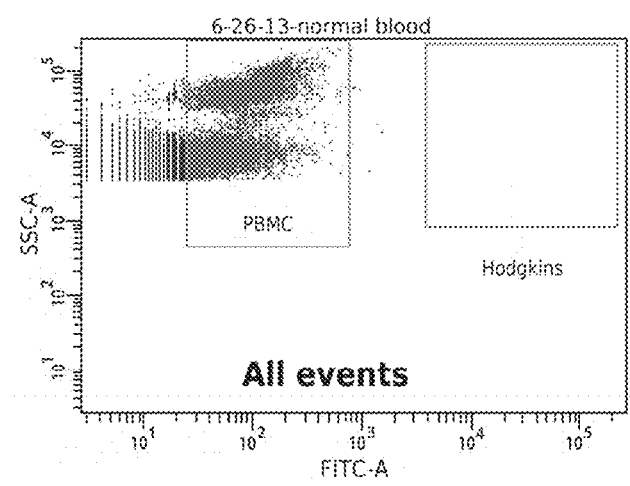
Figure 9C:
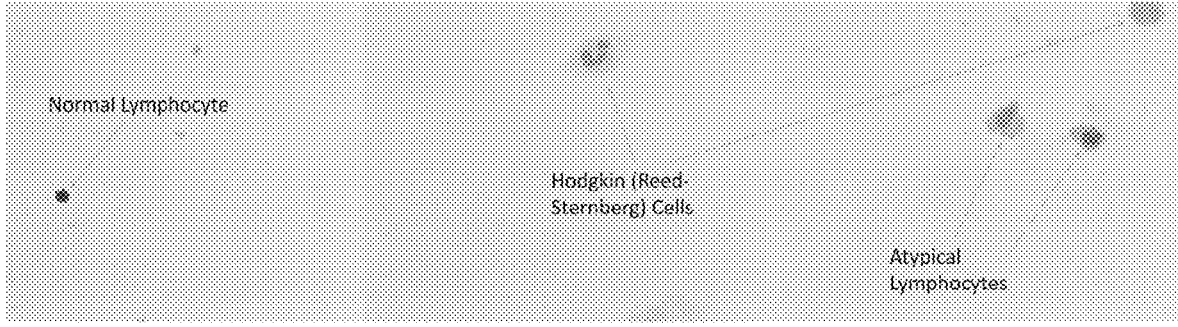

FIG. 9A shows blood from the cancer patient with RBC lysis and staining by BCECF AM (0.016 mM) for one hour at room temperature, demonstrating that cancer cells have a stronger level of fluorescence, allowing their detection, identification, counting, and sorting for later analyses. FIG. 9B shows blood from the healthy volunteer with RBC lysis and staining by BCECF AM (0.016 mM) for one hour at room temperature. FIG. 9C shows circulating cancer cells that were isolated, and normal lymphocytes, viewed at 40× magnification.

This example demonstrated: (1) circulating cancer cells in a blood sample from a cancer patient with lysed red blood cells, could be separated in a FACS sorter after incubation with a basic pH-sensitive fluorescent dye (FIG. 9A); and (2) a blood sample from healthy volunteer with lysed RBC after incubation with the same basic pH-sensitive fluorescent dye showed almost no cells with high fluorescence level, indicating lack of circulating cancer cells (FIG. 9B).

Example 4

This example demonstrated that human cancer cells in peripheral blood may be identified and isolated, exploiting their preferential maintenance of a more basic pH level than their surrounding media or other blood borne cells. In this example, the generality was further illustrated by the use of a different (5(6)-carboxyfluorescein) pH-sensitive fluorescent dye, which was added to carcinoma cells and normal blood cells. The fluorescent signal corresponding to the dye internalized in cells with more basic pH was then used for detection, counting, and potential separation in a flow cytometer or sorter machine. In the present example, a fluorescence-activated cell sorting (FACS) system was used. The sorted cells were presented in a well-preserved state, which allowed following cytopathological and genetic analyses.

HT29 cells (human colon carcinoma) were obtained from ATCC and 2 ml of whole normal human blood was collected from healthy volunteer. Blood was processed within 2 hours of collection, mixed with carcinoma cells and examined by a BD FACSARIA II SORP machine following incubation of a fluorescent dye: 5(6)-carboxyfluorescein. Blood was processed with RBC lysis. 1 g of 5(6)-carboxyfluorescein (Sigma Aldrich) was dissolved in 100 ml of distillate water, a saturated solution in water was produced, and 10 aliquots were prepared.

Lysis of the RBCs then was performed, after staining by fluorescent dye (5(6)-carboxyfluorescein) by adding to the sample 1 ml of RBC lysis buffer (BioLegend) dissolved in 10 ml of distillate water and incubated for 10 minutes at room temperature. PBS was then added up to 50 ml total volume, followed by centrifugation (2000 rpm for 10 min) and removal of the supernatant.

2 ml of each sample was introduced for analysis by a BD FACSARIA II SORP machine and the data analyzed by the system software. HT29 cells were further sorted and isolated on the glass slide for microscopy. The slide was stained according to standard H&E protocol.

Figure 10A:
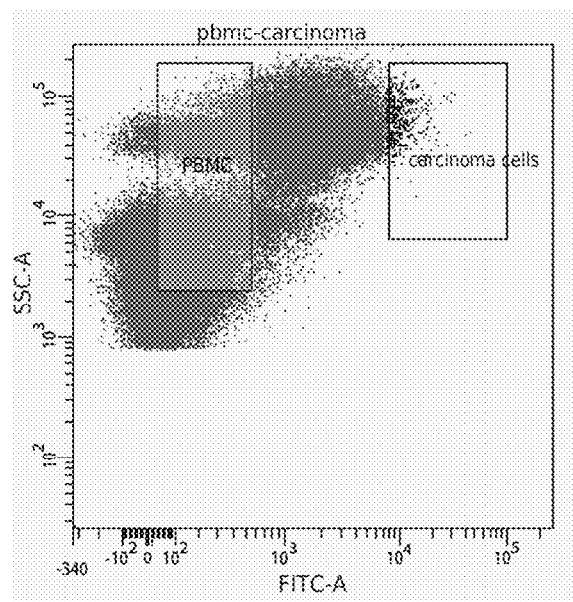
FIGS. 10A-10C show a mixture of blood with RBC lysis and HT29 cells, in accordance with some embodiments of the invention.
Figure 10B:
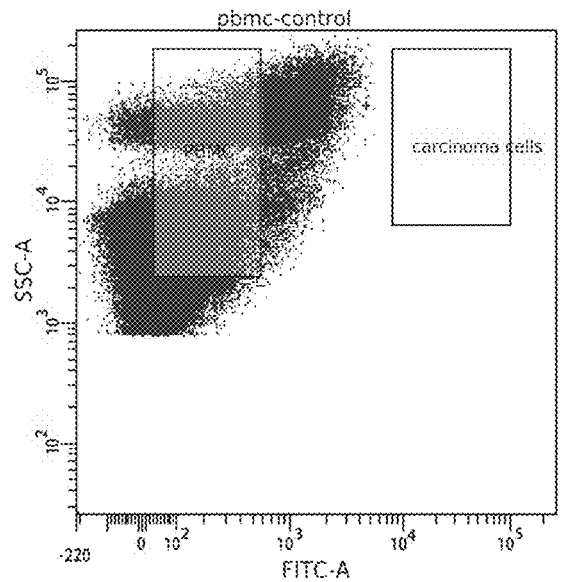
Figure 10C:
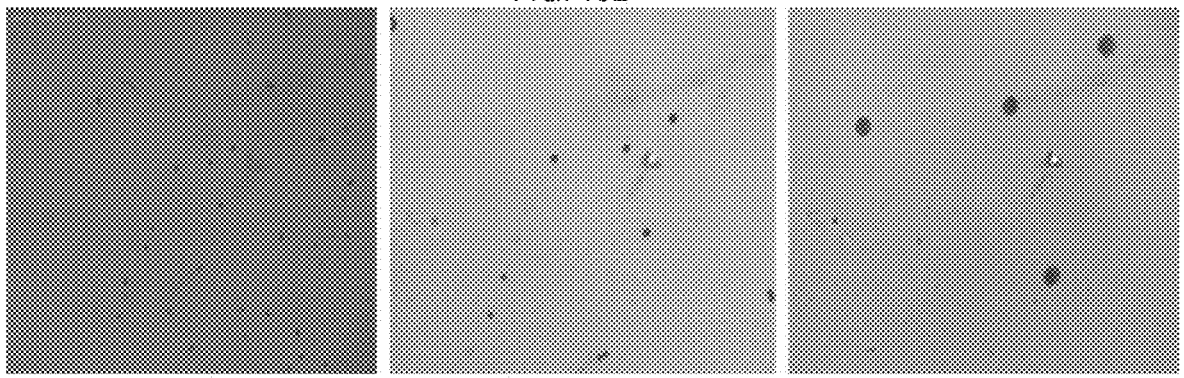

FIG. 10A shows a mixture of blood with RBC lysis and HT29 cells incubated with 5(6)-carboxyfluorescein for 30 minutes at room temperature. HT29 cells showed a much stronger fluorescence signal then blood cells, and could be detected and sorted in the FACS sorter machine. FIG. 10B shows blood alone, with RBC lysis without HT29 cells incubated with 5(6)-carboxyfluorescein for 30 minutes at room temperature. This example does not have a high fluorescence cell population, corresponding to carcinoma cells, present in previous figure. FIG. 10C shows circulating cancer cells that were isolated, and viewed at different magnifications (same region).

This example demonstrated: (1) a mixture of normal circulating blood with lysed RBC with isolated carcinoma cells could be separated in a FACS sorter after incubation with a basic pH-sensitive fluorescent dye (FIG. 10A); and (2) a normal circulating blood with lysed RBC without carcinoma cells shows no positive (high fluorescents) cells population corresponding to carcinoma cells, after incubation with the same dye (FIG. 10B). This example further demonstrated that the methods of the instant invention were not limited to any specific composition of the fluorescent dye or any other reporter molecule, and that any molecule that could provide pH-specific signal may be utilized.

Example 5

This example demonstrated that human cancer cells in peripheral blood could be identified and isolated, exploiting their preferential maintenance of a more basic pH level than their surrounding media or other blood borne cells. This example also demonstrated that treatment of the sample of cells, before staining by a pH-sensitive fluorescent dye, using a low pH buffer could modify the outcome of the test, and depending on the specific application and properties of the cells, could be used to further improve the selectivity of the present invention. In this example, pH-sensitive fluorescent dye was added to carcinoma cells and normal blood cells, after pretreatment with low pH buffer and without such pretreatment and the fluorescent signal corresponding to the dye internalized in cells with more basic pH is used for detection, counting, and potential separation in a flow cytometer or sorter machine. In the present example, a fluorescence-activated cell sorting (FACS) system was used.

HT29 cells (human colon carcinoma) were obtained from ATCC and 2 ml of whole normal human blood was collected from healthy volunteer. Blood was processed within 2 hours of collection, mixed with carcinoma cells and examined by a BD FACSARIA II SORP machine following incubation of a fluorescent dye (BCECF AM). Blood was processed with RBC lysis.

Treatment of one of the samples by low pH buffer was done by adding of 20 ml of Acetate buffer solution pH 4.6 (Sigma-Aldrich) diluted 1:20 in distillate water for 10 minutes at room temperature. PBS was then added up to 50 ml total volume, followed by centrifugation (2000 rpm for 10 min) and removal of the supernatant.

1 mg of BCECF AM (Invitrogen) was dissolved in 1 ml of DMSO and 10 aliquots were prepared. One aliquot was dissolved in 10 ml of Hank's balanced salt solution in order to make a working solution (0.016 mM). The working solution of BCECF AM was added to samples (2 ml of BCECF AM to 2 ml of sample) and incubated at room temperature for 30 minutes.

Lysis of the RBCs then was performed, after staining by fluorescent dye BCECF AM by adding to the sample 1 ml of RBC lysis buffer (BioLegend) dissolved in 10 ml of distillate water and incubated for 10 minutes at room temperature. PBS then was added up to 50 ml total volume, followed by centrifugation (5000 rpm for 10 min) and removal of the supernatant. 2 ml of each sample was introduced for analysis by a BD FACSARIA II SORP machine and the data analyzed by the system software.

Figure 11A:
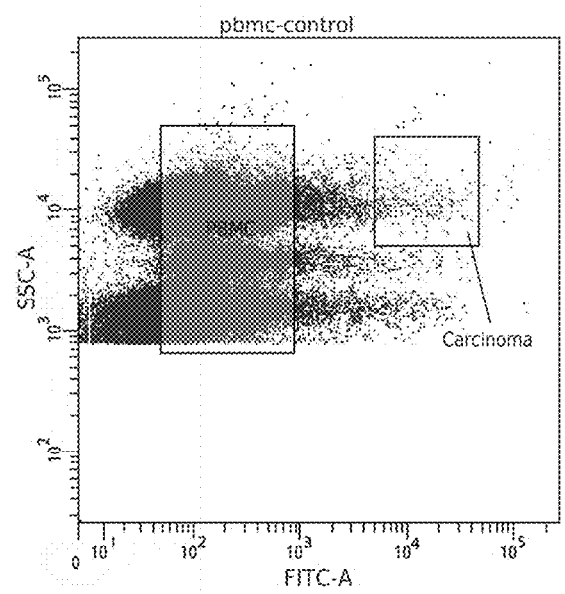
FIGS. 11A-11B show a mixture of blood with RBC lysis and HT29 cells incubated with BCECF AM, according to certain embodiments of the invention.
Figure 11B:
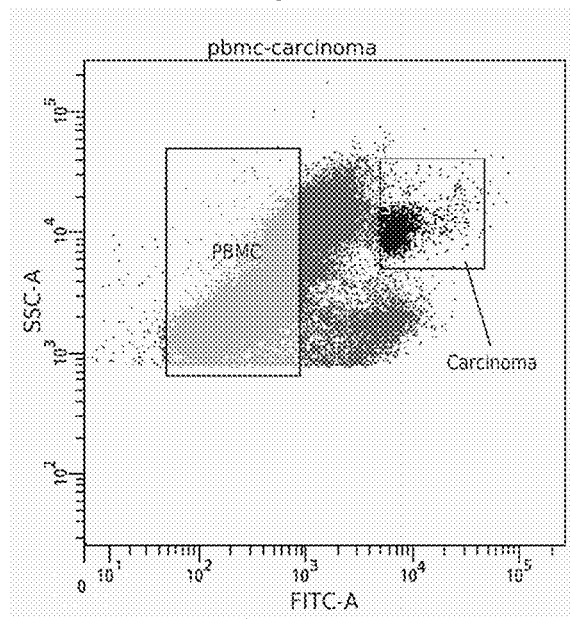

FIG. 11A shows a mixture of blood with RBC lysis and HT29 cells incubated with BCECF AM for 30 minutes at room temperature. HT29 cells showed stronger fluorescent signal than blood cells, and could then be detected and sorted by the FACS sorter machine. FIG. 11B shows a mixture of blood with RBC lysis and HT29 cells treated by low pH buffer and incubated with BCECF AM for 30 minutes at room temperature. HT29 cells showed much more solid and homogeneous population in comparing with the sample without low pH buffer treatment. At the same time, normal blood cells population showed a shift to right, corresponding to more alkaline intracellular pH in comparing with the sample without low pH buffer treatment.

This example demonstrated: (1) a mixture of normal circulating blood with lysed RBC without treatment by low pH buffer with isolated carcinoma cells could be separated in a FACS sorter after incubation with a basic pH-sensitive fluorescent dye (FIG. 11A); and (2) a normal circulating blood with lysed RBC with isolated carcinoma cells treated by low pH buffer showed changes in fluorescence cells population corresponding to carcinoma cells and normal blood cells, after incubation with the same dye (FIG. 11B).

Example 6

This example demonstrated that fetal/embryonic cells in peripheral mother blood could be identified and isolated, exploiting their preferential maintenance of a more basic pH level than their surrounding media or other blood borne cells. In this example, a pH-sensitive fluorescent dye was added to peripheral blood of pregnant women, and the fluorescent signal corresponding to the dye internalized in cells was significantly higher for cells with more basic pH. This signal was then used for detection, counting, and potential separation in a flow cytometer or sorter machine. In the present example, a fluorescence-activated cell sorting (FACS) system was used. Verification that the fraction of cells separated did contain fetal cells was performed using PCR techniques for presence of a Y chromosome (PrimerDesign, h-Y-DNA PCR). Since it was expected that about 50% of the samples should contain the Y chromosome (for a sample size of sufficient statistical significance), and none of the maternal cells should have that chromosome, its subsequent identification in the isolated cell fraction in the FACS machine may be used to demonstrate the isolation of fetal cells in maternal blood.

3 ml of whole blood was collected from six pregnant women, with pregnancy status confirmed by HCG testing and additionally age of gestation by ultrasound, following consent by an Institutional Review Board approved study at a clinical site (Planned Parenthood of Southern New England, New Haven, Conn.). The de-identified samples were arbitrarily marked 001, 002, 003, 004, 005, and 006. Blood was processed within 6 hours of collection and examined by a BD FACSARIA II SORP cell sorting machine, following incubation with a fluorescent dye (BCECF AM). Another 4 samples, 3 ml each, were collected from pregnant women with pregnancy confirmed by HCG testing and ultrasound as described before, following consent by an Institutional Review Board approved study at a clinical site (Planned Parenthood of Southern New England, New Haven, Conn.). The samples were arbitrarily marked 007, 008, 009, and 010. Blood was kept at 4° C. overnight and then processed using the same protocol as the first set of samples.

1 mg of BCECF AM (Invitrogen) was dissolved in 1 ml of DMSO and 10 aliquots were prepared. 3 aliquots were dissolved in 10 ml of Hank's balanced salt solution in order to make a working solution (0.016 mM). The working solution of BCECF AM was added to samples (3 ml of BCECF AM to 3 ml of sample) and incubated at room temperature for 40 minutes. Lysis of the RBCs then was performed, after staining by fluorescent dye (BCECF AM), by adding to the sample 20 ml of RBC lysis buffer (BioLegend) to each sample (2 ml of buffer was dissolved in 20 ml of distillate water and incubated with a blood sample for 10 minutes at room temperature). PBS was then added to result in a total volume of 50 ml, followed by centrifugation (2000 rpm for 10 min) and removal of the supernatant.

2 ml of each sample was introduced for analysis by a cell sorter (BD FACSARIA II SORP) and the data analyzed by the system software. Fetal/embryonic cells were further sorted and isolated in a tube containing 1 ml of PBS. The sorted samples were underwent PCR analysis for the human Y chromosome. Samples 003, 004, and 007 were found positive by qualitative PCR for human Y chromosome.

This example demonstrated: (1) six blood samples from pregnant women in early pregnancy with lysed mother RBC were collected, and that fetal/embryonic cells could be separated in a FACS sorter after incubation with a basic pH-sensitive fluorescent dye; (2) four blood samples from pregnant women in early pregnancy with lysed mother RBC were collected, kept at 4° C. before processing as a part of stability study, and that fetal/embryonic cells could be separated in a FACS sorter after incubation with a basic pH-sensitive fluorescent dye.

Example 7

This example demonstrated that fetal/embryonic cells in peripheral mother blood could be identified and isolated, exploiting their preferential maintenance of a more basic pH level than their surrounding media or other blood borne cells. In this example, a pH-sensitive fluorescent dye was added to peripheral blood of pregnant women, and the fluorescent signal corresponding to the dye internalized in cells was significantly higher for cells with more basic pH. This signal was then used for detection, counting, and separation in a flow cytometer or sorter machine. In the present example a fluorescence-activated cell sorting (FACS) system was used. Verification that the fraction of cells separated using the method of the present invention did contain fetal cells was performed using the real-time PCR technique Quantifiler® Duo DNA Quantification Kit (Applied Biosystems®) for quantitative and qualitative assessment of total human and human male DNA in a sample.

Since it was expected that about 50% of the samples should contain the male (fetus) DNA (when the number of samples is large enough to become statistically significant), and since all samples should have human DNA, its subsequent identification and quantification in the isolated cell fraction in the FACS machine may be used to demonstrate the utility of the present invention for isolation of fetal cells in maternal blood, and may further be used to calculate the purification factor afforded by the present invention.

3.5 ml of whole blood was collected from three pregnant women, with pregnancy status confirmed by HCG testing and additionally age of gestation by ultrasound, following consent by an Institutional Review Board approved study at a clinical site (Planned Parenthood of Southern New England, New Haven, Conn.). The de-identified samples were arbitrarily marked 019, 020, and 022. Blood was processed within 36 hours of collection and examined by a BD FACSARIA II SORP cell sorting machine, following incubation with a fluorescent dye (BCECF AM). The samples were kept at 4° C. after collection and before processing.

1 mg of BCECF AM (Invitrogen) was dissolved in 1 ml of DMSO and 10 aliquots were prepared. 2 aliquots were dissolved in 10 ml of Hank's balanced salt solution in order to make a working solution (0.016 mM). The working solution of BCECF AM was added to samples (3.5 ml of BCECF AM to 3.5 ml of sample) and incubated at room temperature for 40 minutes. Lysis of the RBCs then was performed, after staining by fluorescent dye (BCECF AM), by adding to the sample 20 ml of RBC lysis buffer (BioLegend) to each sample (2 ml of buffer was dissolved in 20 ml of distillate water and incubated with a blood sample for 10 minutes at room temperature). PBS was then added to result in a total volume of 50 ml, followed by centrifugation (2000 rpm for 10 min) and removal of the supernatant.

2 ml of each sample was introduced for analysis by a cell sorter (BD FACSARIA II SORP) and the data analyzed by the system software. The fetal/embryonic cells were further sorted and isolated in a tube containing 0.1 ml of PBS. The sorted samples subsequently were processed with a real time PCR protocol.

Samples 019 and 022 showed a positive signal for male DNA, while sample 022 was negative. Quantitative analysis of data showed that the ration between fetal and maternal DNA was between 1:400 to 1:700. Quantitative analysis of data also showed, taking in account the total number of sorted cells per sample (50,000), that about 100 fetal cells were recovered from 3.5 ml of maternal blood.

Figure 12A:
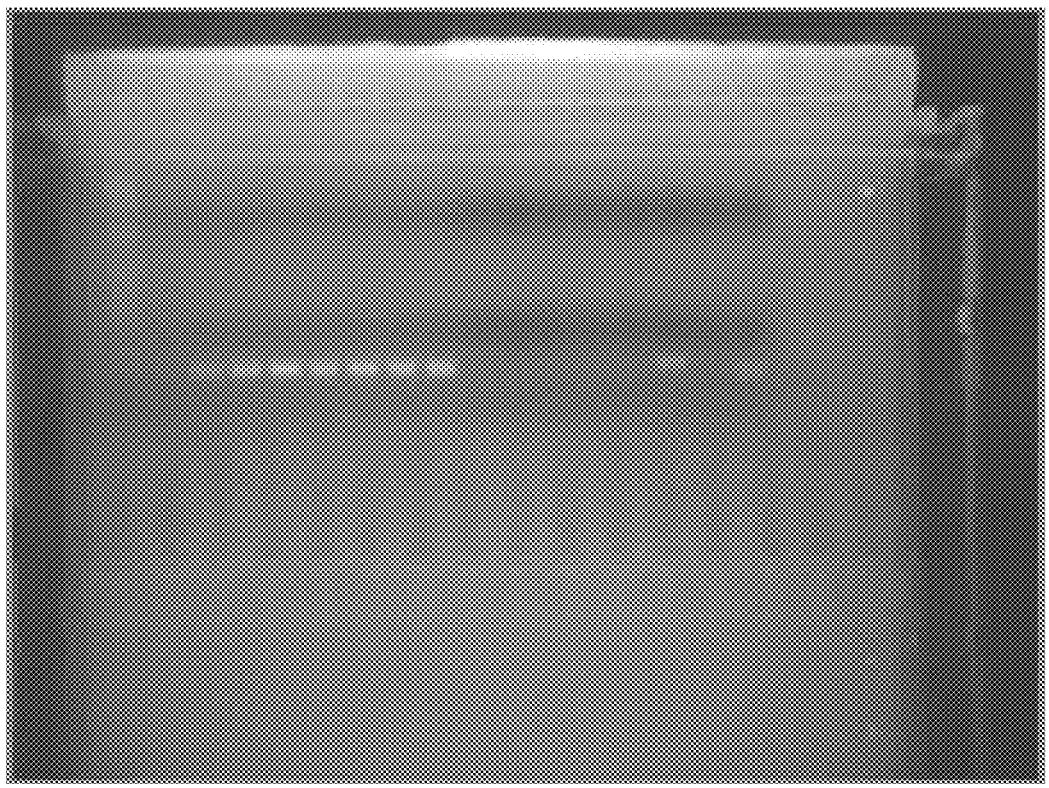
FIGS. 12A-12C illustrate the presence of DNA, in accordance with certain embodiments of the invention.
Figure 12B:
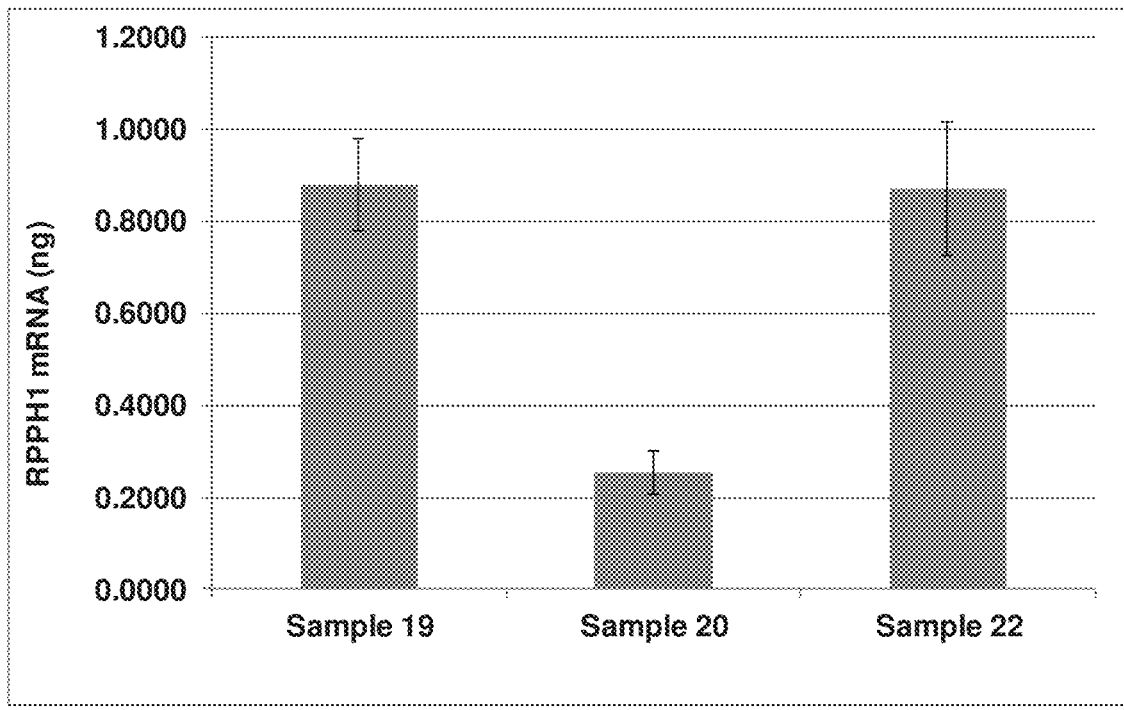
Figure 12C:
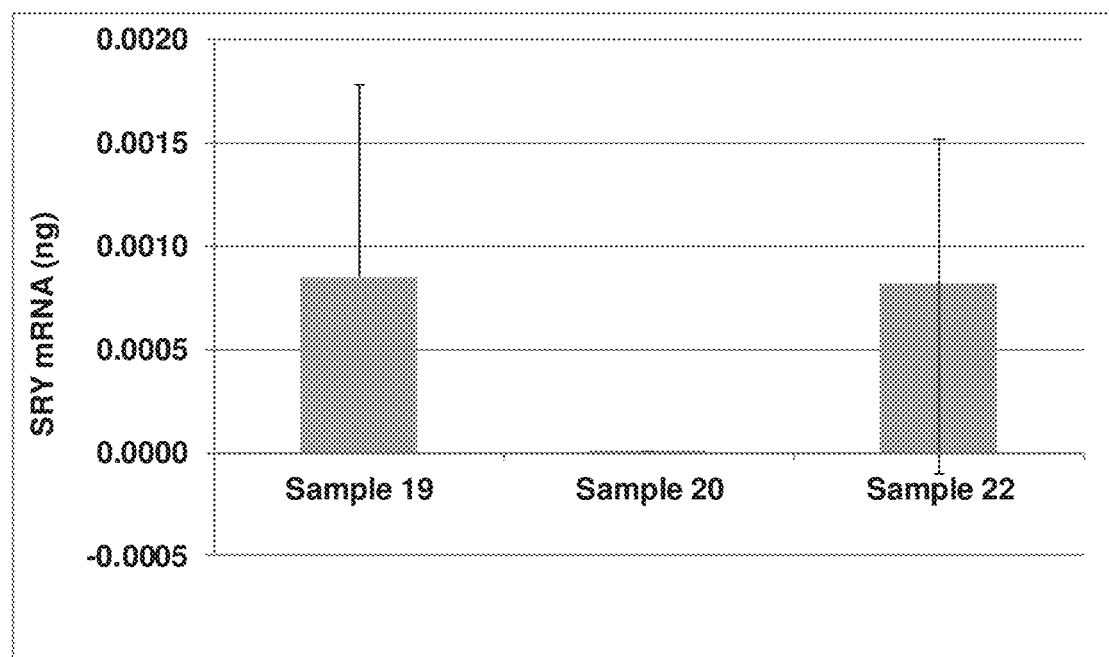

Three blood samples from pregnant women in early pregnancy with lysed mother RBC were collected. The gestation age of the samples was 6 weeks and 4 days for sample 019, 7 weeks and 1 day for sample 020, and 5 weeks and 5 days for sample 022. Fetal/embryonic cells could be separated in a FACS sorter after incubation with a basic pH-sensitive fluorescent dye. A picture of the electrophoresis gel showing presence of male DNA in samples 019 and 022 is shown in FIG. 12A. A graph showing a quantity of human DNA in the samples 019, 020, and 022 is shown in FIG. 12B. A graph showing a quantity of male DNA in the samples 019, 020, and 022 is shown in FIG. 12C.

Example 8

In this example, it was demonstrated that fetal/embryonic cells in peripheral mother blood can be identified and isolated, exploiting their preferential maintenance of a more basic pH level than their surrounding media or other blood borne cells. In this example, a pH sensitive fluorescent dye was added to peripheral blood of pregnant women, and the fluorescent signal corresponding to the dye internalized in cells was significantly higher for cells with more basic pH.

This signal was then used for detection, counting, and separation in a flow cytometer or sorter machine, in the present example, using a Fluorescence-Activated Cell Sorting (FACS) system. This example further demonstrated that the natural pH difference between fetal and maternal cells may be sufficiently large to enable a high degree of purification (ratio of fetal to maternal cells in the isolated cell fraction), especially when extra care is taken to avoid other pH modifying agents that may penetrate all cells in the sample. As an example, certain RBC cell lysing agents may contain compounds that can increase intercellular pH and thus reduce the overall difference between fetal and maternal cells. In this example, it is shown that avoiding lysing agents increased the overall purity of the isolated cell fraction. Verification that the fraction of cells that were separated contained fetal cells was performed using real time PCR techniques: Quantifiler® Duo DNA Quantification Kit (Applied Biosystems®) for quantitative and qualitative assessment of total human and human male DNA in a sample.

Since it is expected that about 50% of the samples should contain the male (fetus) DNA (i.e., when the number of samples is large enough to become statistically significant), and since all samples should have human DNA, its subsequent identification and quantification in the isolated cell fraction in the FACS machine may be used to demonstrate the utility of the present invention for isolation of fetal cells in maternal blood, and may further be used to calculate the purification factor.

This example demonstrated three blood samples from pregnant women in early pregnancy without lysis of mother RBC. The gestation age of the samples was 7 weeks and 3 days for sample 034 (arbitrary labeled), 5 weeks and 0 day for sample 035, and 9 weeks and 6 days for sample 036. Fetal/embryonic cells could be separated in a FACS sorter after incubation with a basic pH sensitive fluorescent dye (FIG. 13 for sample 035 which was positive also for Y chromosome).

3.5 ml of whole blood was collected from three pregnant women, with pregnancy status confirmed by HCG testing and additionally age of gestation by ultrasound, following consent by an Institutional Review Board approved study at a clinical site (Planned Parenthood of Southern New England, New Haven, Conn.). The de-identified samples were marked 034, 035, 036. Blood was processed within 36 hours of collection and examined by a BD FACSARIA II SORP cell sorting machine, following incubation with a fluorescent dye (BCECF AM). The samples were kept at 4° C. after collection and before processing.

1 mg of BCECF AM (Invitrogen) was dissolved in 1 ml of DMSO and 10 aliquots were prepared. 2 aliquots were dissolved in 10 ml of Hank's Balanced Salt Solution in order to make working concentration (0.016 mM). A working solution of BCECF AM was added to samples (3.5 ml of BCECF AM to 3.5 ml of sample) and incubated in room temperature for 40 minutes. Lysis of RBC was not performed. As mentioned earlier, one component in the RBC lysis buffer (BioLegend) is ammonium chloride, which nonspecifically increases intracellular pH in cells of different origin, including adult neutrophils, possibly causing non-specific background increase for the assay and thus reducing difference in pH inherent in the untreated sample. PBS was then added to result in a total volume of 50 ml, followed by centrifugation (2000 rpm for 10 min) and removal of the supernatant. 2 ml of each sample was introduced for analysis by a cell sorter (BD FACSARIA II SORP) and data analyzed by the system software. Fetal/embryonic cells were further sorted and isolated in a tube containing 0.2 ml of PBS. The sorted samples underwent real time PCR protocol.

Samples 035 showed positive signal for male DNA, samples 034 and 036 were negative, and the total number of sorted for PCR cells in sample 035 was 50 cells.

Example 9

In this example, it was demonstrated that fetal/embryonic cells in peripheral mother blood can be identified and isolated, exploiting their preferential maintenance of a more basic pH level than their surrounding media or other blood borne cells. In this example, intracellular pH sensitive fluorescent dye was added to peripheral blood of pregnant women, and the fluorescent signal corresponding to the dye internalized in cells was found to be significantly higher for cells with more basic pH. This signal was then used for detection, counting, and separation in a flow cytometer or sorter machine; in the present example, this was a Fluorescence-Activated Cell Sorting (FACS) system. Verification that the fraction of separated cells did contain fetal cells was performed using DNA FISH (AneuVysion Multicolor DNA probe Kit, Abbott) for Y and X chromosomes. Specifically, while X chromosomes are found in both the maternal and fetal cells, it was expected that Y chromosomes would be found in about one-half of the total number of samples detected, since it could not have been originated from maternal origin.

The gestation age of the samples was 6 weeks and 3 days for sample 033, 5 weeks and 0 day for sample 035 (arbitrary labeled). 3.5 ml of whole blood was collected from three pregnant women, with pregnancy status confirmed by HCG testing and additionally age of gestation evaluation by ultrasound, following consent by an Institutional Review Board approved study at a clinical site (Planned Parenthood of Southern New England, New Haven, Conn.). The de-identified samples were marked 033, 035. Blood was processed within 36 hours of collection and examined by a BD FACSARIA II SORP cell sorting machine, following incubation with a fluorescent dye (BCECF AM). The samples were kept at 4° C. after collection and before processing.

1 mg of BCECF AM (Invitrogen) was dissolved in 1 ml of DMSO and 10 aliquots were prepared. 2 aliquots were dissolved in 10 ml of Hank's Balanced Salt Solution in order to make working concentration (0.016 mM). A working solution of BCECF AM was added to samples (3 ml of BCECF AM to 3.5 ml of sample) and incubated in room temperature for 40 minutes. Lysis of the RBCs was then performed for sample 033. After staining by fluorescent dye (BCECF AM) by adding to the sample 20 ml of RBC lysis buffer (BioLegend), 2 ml of buffer was dissolved in 20 ml of distillate water and incubated with a blood sample for 10 minutes in room temperature. PBS was then added up to 50 ml total volume, followed by centrifugation (1600 rpm for 10 min) and removal of the supernatant. Lysis of RBC was not performed for sample 035. After staining by fluorescent dye (BCECF AM) PBS was added up to 50 ml total volume, followed by centrifugation (1600 rpm for 10 min) and removal of the supernatant.

2 ml of each sample was introduced for analysis by a cell sorter (BD FACSARIA II SORP) and the data analyzed by the system software. Fetal/embryonic cells were further sorted and isolated on poly-L-lysine microscopic glass slides, and after air drying for 15 minutes, the slides were fixed in 4% paraformaldehyde for 20 minutes. The slides were the washed in PBS three times, 5 minutes for each of the washing step. The slides underwent DNA FISH staining (AneuVysion Multicolor DNA probe Kit, Abbott) for Y and X chromosomes. On the slide 033, 11 cells were present for analysis after FISH staining, and 7 cells were shown to be positive for Y chromosome (63.6% purity level). On the slide 035, 7 cells were present for FISH analysis and 5 cells were positive for Y chromosome (71.4% purity).

Figure 14A:
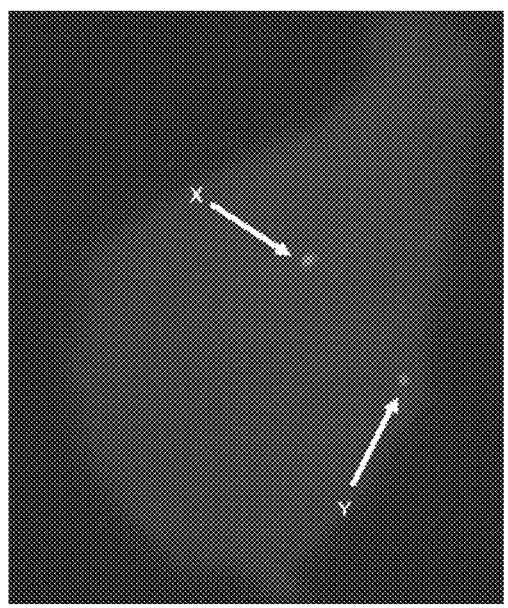
FIG. 14A-14B illustrate the presence of Y chromosome in fetal cells, in accordance with certain embodiments of the invention.
Figure 14B:
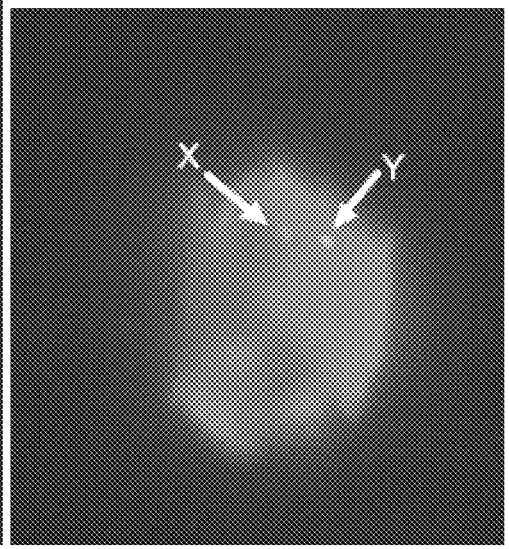

This example demonstrates that Y chromosome positive cells by DNA FISH (presumably from a male fetus) could be separated by a FACS sorter after incubation with an intracellular pH sensitive fluorescent dye with high purity from blood samples of pregnant women in early pregnancy with and without lysis of maternal RBC (FIGS. 14A and 14B).

Example 10

In this example, it was demonstrated that human cancer cells in peripheral blood could be identified and isolated exploiting their preferential maintenance of a more basic pH and cell granularity or internal complexity level than their surrounding media or other blood borne cells. In this example, intracellular pH sensitive fluorescent dye was added to carcinoma cells and normal blood cells, and the fluorescent signal corresponding to the dye internalized in cells with more basic intracellular pH is used for detection, counting, and potential separation in a flow cytometer or sorter machine; in the present examples, using a Fluorescence-Activated Cell Sorting (FACS) system. The sorted cells were presented in a well-preserved state, which allowed following cytopathological and genetic analyses.

CRL-2422 cells (human prostate adenocarcinoma) were obtained from ATCC and 2 ml of whole blood was collected from non-pregnant women without any history of cancer following consent by an Institutional Review Board approved study at a clinical site (Planned Parenthood of Southern New England, New Haven, Conn.). The de-identified sample was marked 4a001 (arbitrary labeled). Blood was processed within 36 hours of collection. The sample was kept at 4° C. after collection and before processing. 2 ml of blood was mixed with approximately 10,000 of prostate carcinoma cells (CRL-2422) and incubated with BCECF AM.

1 mg of BCECF AM (Invitrogen) was dissolved in 1 ml of DMSO and 10 aliquots were prepared. One aliquot was dissolved in 10 ml of Hank's Balanced Salt Solution in order to prepare working concentration (0.016 mM). The working solution of BCECF AM was then added to samples (2 ml of BCECF AM to 2 ml of sample) and incubated in room temperature for 40 minutes. Lysis of RBC was performed after staining by fluorescent dye (BCECF AM) by addition of 15 ml of distillate water to the sample for 30 seconds. PBS was then added up to 50 ml total volume, followed by centrifugation (1500 rpm for 10 min) and removal of the supernatant. The sample was introduced for analysis by BD FACSARIA II SORP machine and the data analyzed by the system software. CRL-2422 cells were further sorted and isolated on a glass slide.

Figure 15A:
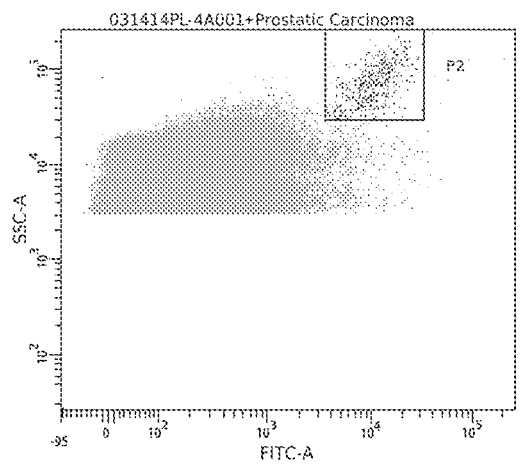
Figure 15B:
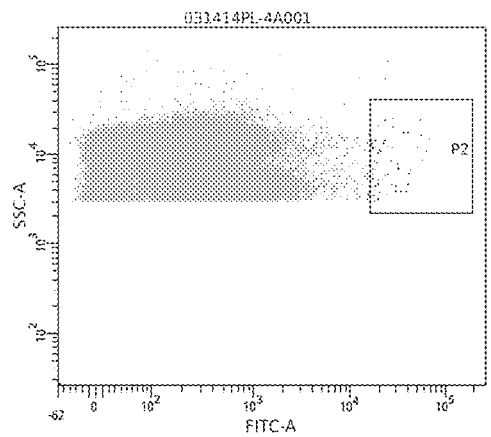

This example demonstrates that carcinoma cells were distinguished by strong fluorescent signal and higher cell granularity/internal complexity when incubated with a intracellular pH sensitive fluorescent dye than normal blood cells in the mixed sample (FIG. 15A), while normal circulating blood cells were not distinguished by strong fluorescent signal and high cells granularity/internal complexity after being incubated with same dye (FIG. 15B). In addition, cells sorted from population of strong fluorescent signal and high cell granularity/internal complexity from a sample of mixed normal blood and carcinoma cells and stained by H&E stain exhibited characteristic morphology corresponding to carcinoma cells (FIG. 15C).

FIGS. 15A-15B illustrate the presence of strong fluorescent signal and higher cell granularity/internal complexity for carcinoma cells when incubated with an intracellular pH sensitive fluorescent dye, than for normal blood cells in a mixed sample.

FIG. 15C illustrate cells with morphological features corresponding to carcinoma cells, which were selected from a population of cells with strong fluorescent signal and high cell granularity/internal complexity in a general mixture of normal blood and carcinoma cells stained by H&E.

Example 11

In this example, it was demonstrated that fetal/embryonic cells that were identified originate from the fetus and not from fetal cells that might persistent from prior pregnancies. In this example, fetal/embryonic cells were determined from the maternal blood of women who were confirmed as not pregnant at the time of collection of blood sample, but with history of pregnancy with a male fetus. In this example, intracellular pH sensitive fluorescent dye was added to peripheral blood of non-pregnant women with a history of previous male pregnancy, and the fluorescent signal corresponding to the dye internalized in cells is some of the cells was higher reflecting more basic intracellular pH. This signal was then used for attempt for detection, counting, and separation of cells using a Fluorescence-Activated Cell Sorting (FACS) system from the blood of non-pregnant women with previous male pregnancy. Verification that the fraction of cells separated did not contain fetal cells was performed using real time PCR for Y chromosome.

3.5 ml of whole blood was collected from six non-pregnant women with history of at least one prior male pregnancy (and at least 6 months before sample collection), with current non-pregnancy status confirmed by HCG testing, following consent by an Institutional Review Board approved study at a clinical site (Planned Parenthood of Southern New England, New Haven, Conn.). Blood was processed within 36 hours of collection and examined by a BD FACSARIA II SORP cell sorting machine, following incubation with a fluorescent dye (BCECF AM). The samples were kept in 4° C. after collection and before processing.

1 mg of BCECF AM (Invitrogen) was dissolved in 1 ml of DMSO and 10 aliquots were prepared. 2 aliquots were dissolved in 10 ml of Hank's Balanced Salt Solution in order to make working concentration (0.016 mM). A working solution of BCECF AM was added to the samples (3 ml of BCECF AM to 3.5 ml of sample) and incubated at room temperature for 40 min. Lysis of RBC then was performed, after staining by fluorescent dye (BCECF AM) by adding to the sample 15 ml of distillate water for 30 seconds. PBS was then added up to 50 ml total volume, followed by centrifugation (1500 rpm for 10 min) and removal of the supernatant. The sample was introduced for analysis by BD FACSARIA II SORP machine and the data analyzed by the system software. 100,000 events were recorded, with the sorting gate for subsequent collection set to include only most high fluorescence cells (30-50 cells per 100,000 events). 400 cells were sorted in the tubes with PBS for real time PCR.

Figure 16B:
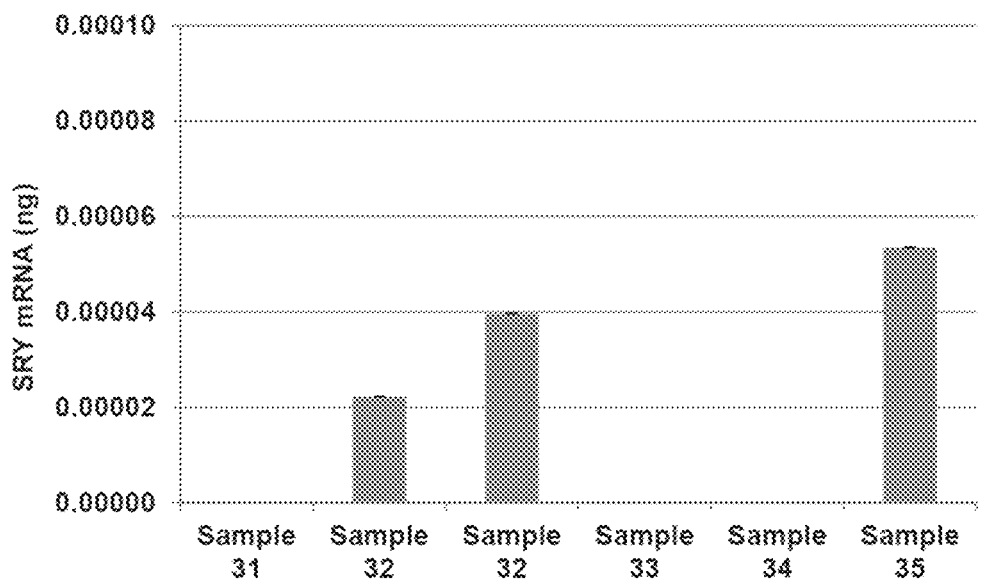
Figure 16C:
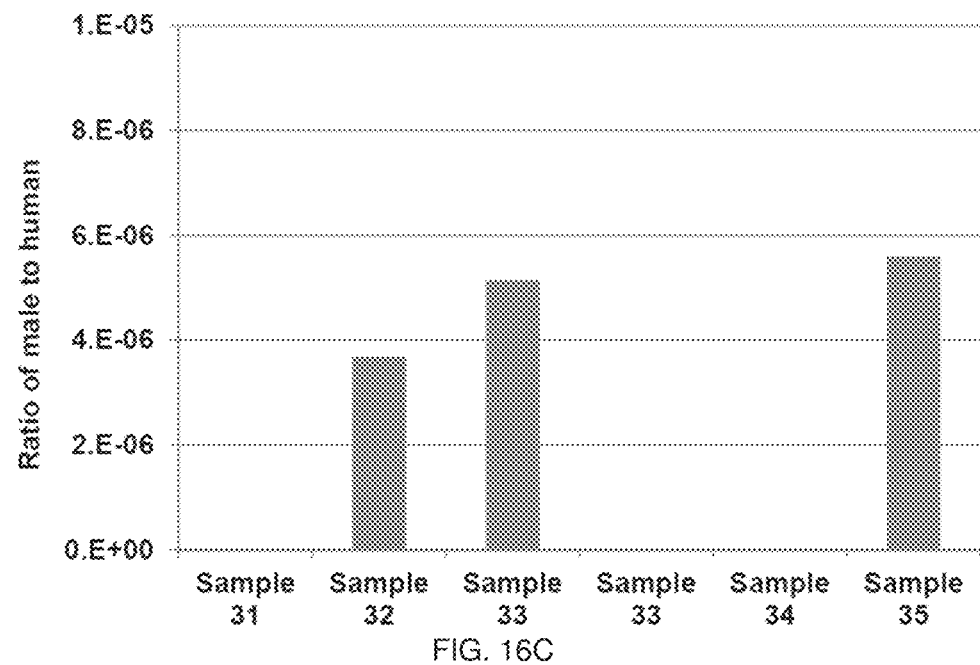

This example specifically demonstrates human mRNA (ng) for the six tested samples (FIG. 16A), with male mRNA (ng) for six tested samples being below an acceptable minimum level of detection of mRNA in the PCR experiments (FIG. 16B). FIG. 16C shows the ratio of male to human mRNA.

FIG. 16A illustrates an amount of human mRNA in cells isolated from blood obtained from non-pregnant women with a prior male pregnancy. FIG. 16B illustrates an amount of male mRNA in cells isolated from blood obtained from non-pregnant women with a prior male pregnancy. FIG. 16C illustrates the ratio of male to total mRNA in cells isolated from blood obtained from non-pregnant women with a prior male pregnancy.

Example 12

This example shows that fetal/embryonic pluripotent stem cells could be identified and isolated from maternal peripheral blood by exploiting the preferential maintenance of a more basic pH level by these stem cells than is exhibited by their surrounding media or other blood-borne cells. These cells could then be cultured in vitro to expand cell number and study their properties, including the ability to form teratomas after xenotransplantation into an immunocompromized host. This ability of CFCs isolated by the methods of the present invention to form teratomas shows that these CFCs share a basic property defining pluripotent stem cells, and indicates that these CFCs are pluripotent stem cells in their behavior.

In this example, an intracellular pH sensitive fluorescent dye was added to peripheral blood of pregnant women. The fluorescent signal corresponding to the dye internalized in cells was significantly higher for cells with more basic pH, though it appears that the dye entered all cells equally. The dye signal was used for detection, counting, and separation in a flow cytometer or a cell sorter machine, in the present example, using a Fluorescence-Activated Cell Sorting (FACS) system.

This example demonstrated embryonic body formation in tissue culture plate from the isolated cells. 2 ml of whole blood was collected from each of 5 pregnant women, with pregnancy status confirmed by HCG testing and additionally age of gestation by ultrasound. The de-identified samples were marked 146, 147, 148, 149 and 150. The gestational ages of the patients were between 5 weeks and 7 weeks. The blood was processed within 36 hours of collection and examined by a BD FACSARIA II SORP cell sorting machine, following incubation with a fluorescent dye (BCECF AM). The samples were kept in 4° C. after collection and before processing.

1 mg of BCECF AM (Invitrogen) was dissolved in 1 ml of DMSO and 10 aliquots were prepared. 2 aliquots were dissolved in 10 ml of Hank's Balanced Salt Solution in order to make a working solution (0.016 mM). The working solution of BCECF AM was added to samples (2 ml of BCECF AM to 2 ml of sample) and incubated in room temperature for 40 minutes in the dark.

Lysis of RBCs then was performed for all samples by adding to the sample 16 ml of distilled water for 30 seconds at room temperature. Then, PBS was added up to 50 ml total volume, followed by centrifugation (800 rpm for 10 min) and removal of the supernatant.

2 ml of each sample was introduced for analysis and sort by a cell sorter (BD FACSARIA II SORP) and data analyzed by the system software. Pluripotent embryonic or fetal stem cells were further sorted and isolated to the 6 well Matrigel plate for Embryonic or fetal stem cell Culture (Corning). Each well contained 3 ml of TeSR-E9 medium (Stemcell Technologies) at room temperature. The plates were placed in a $CO_2$ incubator (37° C., 5% $CO_2$). The medium was replaced every 24 hours. After 5 days of culture, the medium was discharged and plate was stained by an H&E protocol. The colonies were examined under a bright light microscope (Olympus BX51) and pictures were taken by using an Olympus DP73 digital camera for microscopy.

Figure 17:
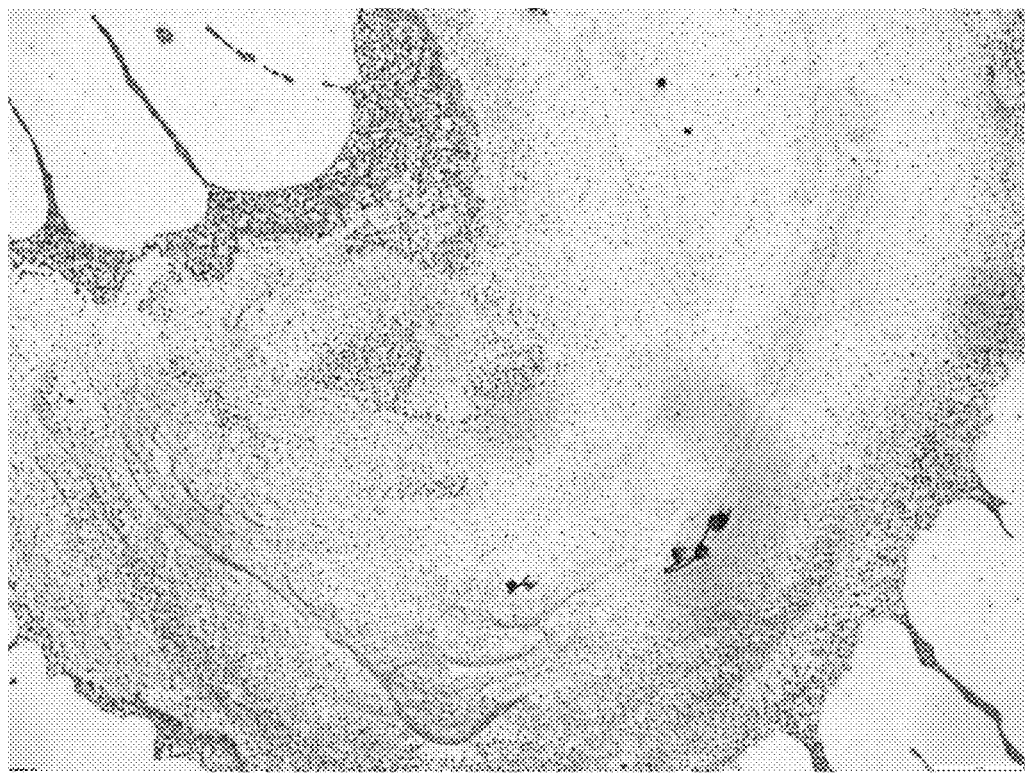
FIG. 17 shows results from an example based on an embodiment of the instant invention.
Figure 18:
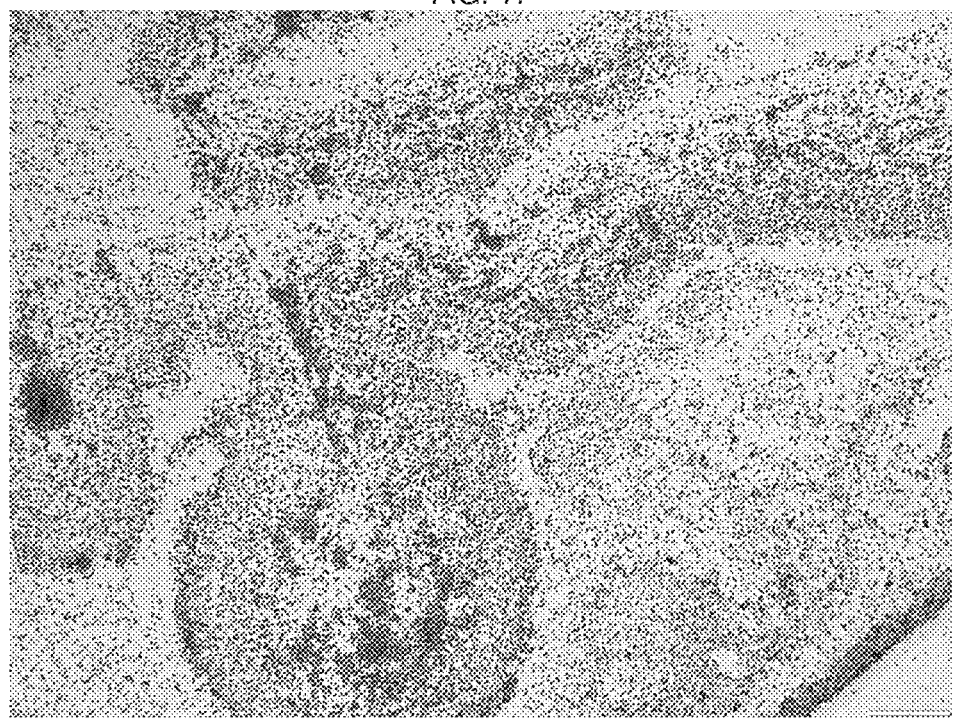
FIG. 18 shows results from an additional example based on an embodiment of the instant invention.

FIG. 17 shows an embryoid body H&E, morphologically displaying all three germ layers. FIG. 18 shows an embryoid body H&E morphologically showing neuroectoderm.

Example 13

This example demonstrates the distinct genetic identity of 10-cell pools of circulating fetal cell (CFC) and maternal cell (MC) samples purified from blood obtained from pregnant women. This demonstration of distinct but related CFC and MC genotypes shows that these CFC were not of maternal origin, and further demonstrates a pattern of genetic inheritance that is consistent with the hypothesis that the CFCs were of fetal origin and were amenable to complex genetic analysis.

The overall genotyping and identity process used in this particular example was as follows. Collect blood from pregnant females. Separate multiple 10-cell pools of CFC and MC from the maternal blood samples by exploiting fluorescent detection of the relatively alkaline intracellular pH of the CFC to enable rapid identification and separation of CFC from maternal blood. Amplify the genomic DNA amount using whole genome amplification (WGA) to prepare sufficient DNA for genotyping and other analyses Specifically PCR amplify 86 genomic fragments containing high frequency single nucleotide polymorphisms (40-50% minor allele frequency), and prepare indexed libraries of these fragments for Illumina sequencing on the MiSeq platform. Sequence the indexed libraries. Analyze the resulting sequence reads covering these 86 SNPs to determine the relative % of reference and alternate alleles at each site. Compare genotypes at all sites between the genetically related MC and CFC samples to determine whether the CFC show genotype inheritance patterns consistent with a fetal origin for the CFC, and inconsistent with a maternal origin for these cells.

Blood collection and purification of fetal and maternal cells. 2 ml of whole blood was collected from each of several pregnant women, with pregnancy status confirmed by HCG testing and gestational age established by ultrasound examination. The collection of samples was after consent. The gestational age of the pregnancy in these subjects was between 5 and 15 weeks. The blood was processed within 36 hours of collection and the blood was examined and sorted using a BD FACSARIA II SORP cell sorting machine following incubation with a fluorescent dye (BCECF AM) and lysis of red blood cells according to a method of the present invention. The samples were kept in 4° C. after collection and before processing.

For the staining of cells, 1 mg of BCECF AM (Invitrogen) was dissolved in 1 ml of DMSO and 10 aliquots were prepared. 2 aliquots were dissolved in 10 ml of Hank's Balanced Salt Solution in order to make a working solution (0.016 mM). The working solution of BCECF AM was added to blood samples (2 ml of BCECF AM to 2 ml of sample) and incubated in room temperature for 40 minutes in the dark.

Lysis of RBCs then was performed after staining by fluorescent dye (BCECF AM) by adding to the samples 16 ml of distilled water for 30 seconds at room temperature. After this short incubation, PBS was added to make 50 ml total volume, followed by centrifugation (800 rpm for 10 min) to collect the pelleted unlysed cells and to remove the lysed cells and supernatant.

The stained sample was then introduced for analysis and sorting by a cell sorter (BD FACSARIA II SORP), and cytometry data analyzed by the system software. 200,000 events were recorded by BD FACSARIA II SORP without sorting. Then the sorting gate was set for 5 most highly fluorescent cells out of 200,000 recorded events for the CFC sorting. The cells were sorted as a multiple 10 cell pools of CFC in the wells of a 96 well PRC plate. Then the sorting gate was set to the cell population with low fluorescent signal (i.e., maternal cells) and the cells were sorted as a multiple 10 cell pools in the wells of a 96 well PRC plate. After collection, the cell pools were stored frozen at −20° C. for further processing. Genotyping of fetal and of maternal cells isolated from maternal circulation was then performed.

Whole Genome Amplification (WGA). Libraries of whole genome amplified (WGA) genomic DNA were prepared from stored cell pools using PicoPLEX DNA-seq. kits as described by the manufacturer (Rubicon Genomics). While PicoPlex was used here, other WGA methods could also be used. The PicoPlex technology was able to reproducibly amplify a specific fraction of the human genome that was well distributed across the genome, starting from very low amounts of template genomic DNA (down to less than a single cell). The PicoPLEX DNA-seq. kit used in this example also contained library preparation reagents and protocols to add the adapters and index sequences needed to allow multiplexed next generation sequencing on sequencers such as the Illumina HiSeq and MiSeq sequencers.

WGA was accomplished by first thawing the frozen cell pools and immediately mixing with the PicoPlex lysis and protease reagents as directed by the manufacturer. This crude cell lysate was then subjected to PicoPlex pre-amplification and PCR amplification steps in the same tube used for cell lysis using primer and polymerase mixes and temperature cycling as described by the manufacturer. The WGA DNA preparations that resulted were then purified using QIAAmp DNA purification kits (Qiagen), and the purified DNA stored frozen at −20° C. for further processing for genotyping.

86-SNP Genotyping Assay. The genotyping assay applied to these WGA DNA samples was designed as a rapid but unambiguous test of the identity of the cells in the original 10-cell pool. This assay measures the genotype at 86 genetically unlinked and highly polymorphic sites in the genome. Cells from a single individual will be identical in genotype at all of these 86 sites, while cells from progeny of that individual (fetal cells from a pregnant mother, for example) are expected to differ from the maternal genotype at approximately half of these sites. Genotypes of unrelated individuals also differ at about half the sites, but the observed differences can include homozygous reference allele to homozygous alternate allele switches that are forbidden by the normal patterns of genetic inheritance, and therefore identify individuals containing such "forbidden" transitions as not related by direct descent.

86-SNP genotyping of maternal cell (MC) and CFC 10-cell pools starts by taking a fraction of the WGA DNA prepared from these pools and subjecting this DNA to further PCR rounds targeted at amplifying 86 distinct genomic 180-274 bp regions, each including one of 86 different common, genetically-unlinked SNPs that had been previously selected and characterized as a forensic tool (see Pakstis A J, et al. "SNPs for a Universal Individual Identification Panel," Human Genetics 127:315-24, 2010). This set of 86 SNPs was selected to have a MAF (minor allele frequency) of >40%, to not show significant linkage disequilibrium between members of the 86-SNP set, and to have relatively constant MAF representation across many different ethnic groups from a wide geographic and ethnic distribution, making this a useful set of assays for genetic identification throughout the human population.

Amplification of 86 genomic loci containing these SNPs used primer pairs supplied by manufacturer was performed. Amplicon libraries for each WGA reaction were diluted and further amplified with a primers configured to add index tags and Illumina sequencing adapters. All 86 amplicons were successfully amplified by both the 86-SNP and indexing amplifications, and the libraries that resulted were pooled, clustered on Illumina flow cells and sequenced on the MiSeq platform using paired-end 150 base pair chemistry. After sequencing, PCR primer sequences and poor quality bases were trimmed from the reads, and the resulting trimmed sequences mapped to the hg19 reference human genome. Read depth for all four alleles at each of the 86 SNP positions, for each of the MC and CFC samples were tabulated, and then the fraction of reference and alternate alleles calculated from these values.

Sequencing generated approximately 3 million paired-end reads per sample, and there were less than 10% failed amplicons per sample. Assays were discarded from the overall genotype analysis for all of the particular SNP assays showing such shallow read depth that the base call from a single read would alter the zygosity call at the SNP.

Genotype Analysis of 86-SNP Assay Data on MC/CFC Sample Pairs. The genotype of the purified cell pools showed that CFC genotype differed from the maternal genotype in every pregnancy analyzed (data from two pregnancies are shown in this example, but other pregnancies have been analyzed and all confirm the pattern of robustly distinct genetic identities for the CFC and MC cell populations). The genotypes determined at the 86 SNP sites assayed in each of the CFC and MC pools are shown in FIGS. 19-22.

In this example, the genotypes of MC and CFC cell samples isolated from the blood of two different pregnant patients were analyzed (10-cell pool samples MC1 and CFC1, and MC4 and CFC4, from patients 1 and 2, respectively). The genotype comparisons for the cells isolated from these two pregnancies are plotted in FIGS. 19-22. All SNP data in each of FIGS. 19-22 is ordered according to the ascending fraction of the reference allele for each SNP in the first MC sample (black triangles in the graphs). The other sample in each comparison is then ordered according to the SNP ordering of the first sample.

Figure 19:
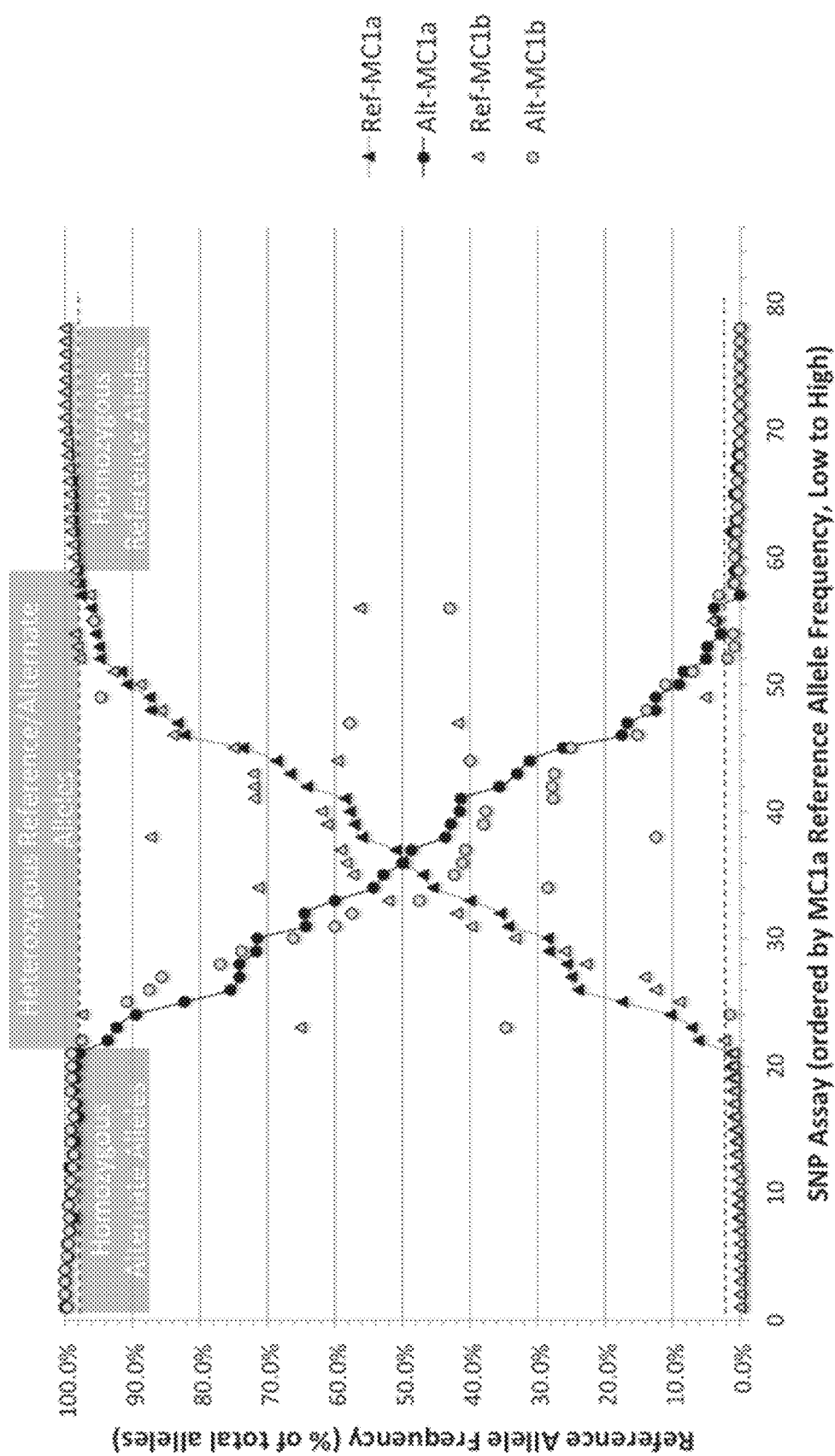
FIGS. 19-22 show genotyping results from an example involving fetal and maternal cells isolated in an embodiment of the instant invention.

The data in FIG. 19 shows replicate genotyping of a single individual. This replicate genotyping shows reproducible homozygous and heterozygous genotype calls clustered in subsets of the SNP assays, with the grouping of SNP subsets differing for each individual. In this first comparison of replicate genotypes, the set of amplicons containing the homozygous alternate and homozygous reference alleles showed reproducible allele ratios, with consistent allele ratios of 99-100% for the defining allele (reference or alternate). The graph in FIG. 19 also shows that the reproducible pattern of genotype identity expected across a set of SNPs if the genomes being compared were essentially identical.

Figure 13:
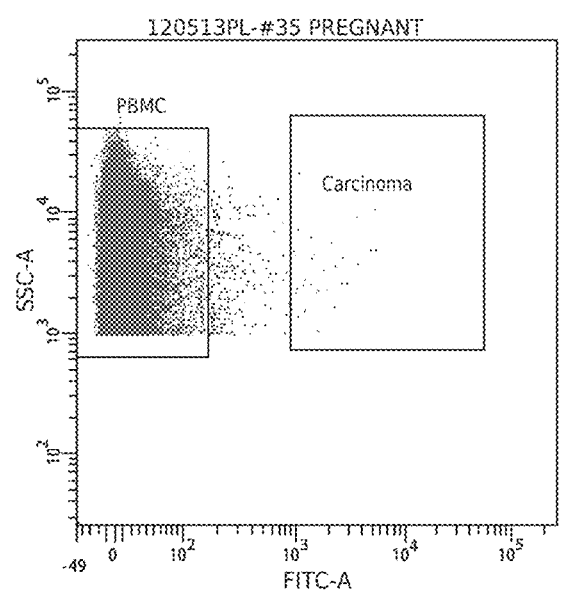
FIG. 13 illustrates purification using non-lysed blood, in accordance with certain embodiments of the invention.

The replicate experiment in FIG. 13 also illustrates another feature of genotypes generated from very low numbers of genomes: while variability in the allele ratio measured for homozygous SNPs is quite low, the ratio measured for heterozygous SNPs may be variable between replicates.

Figure 20:
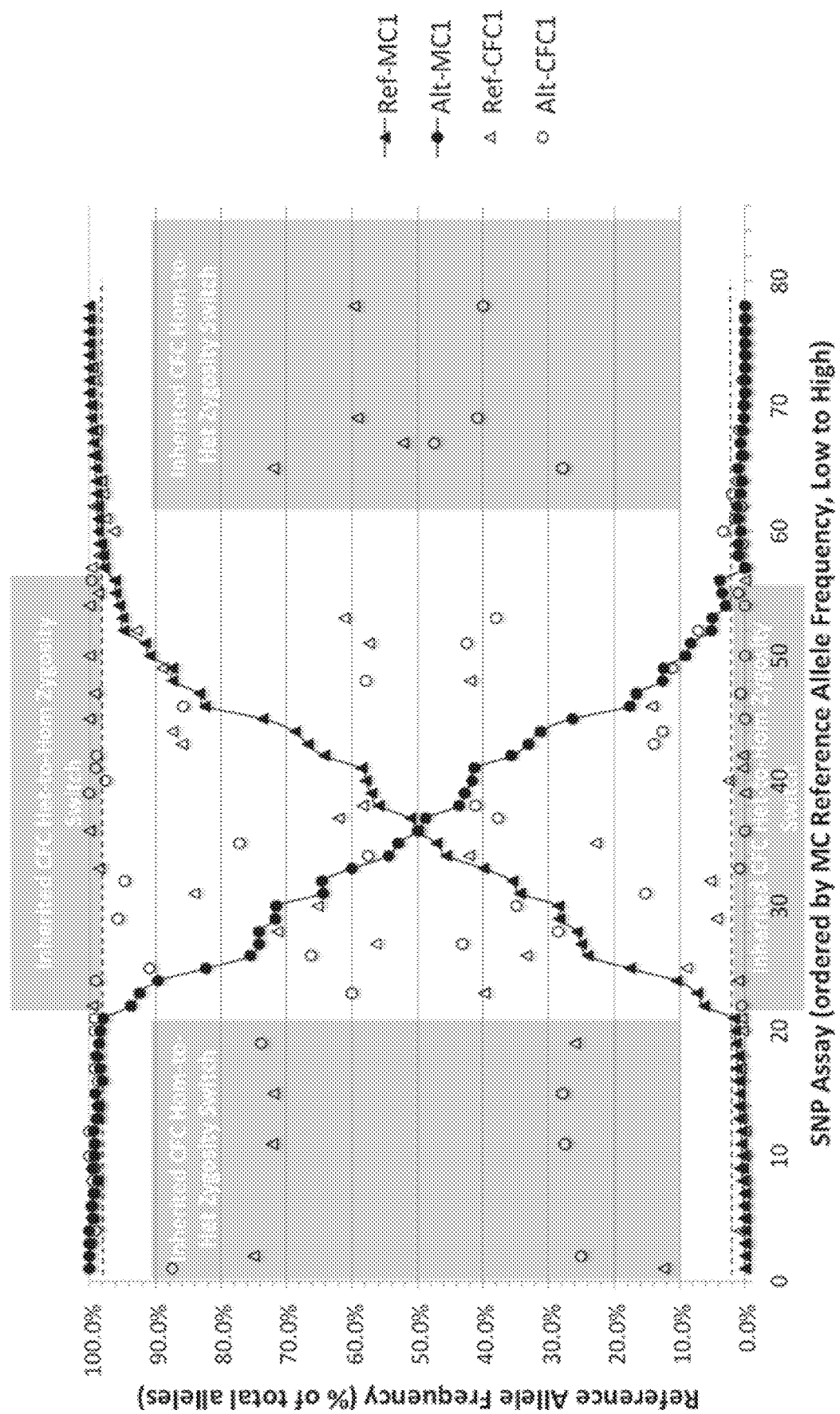
Figure 21:
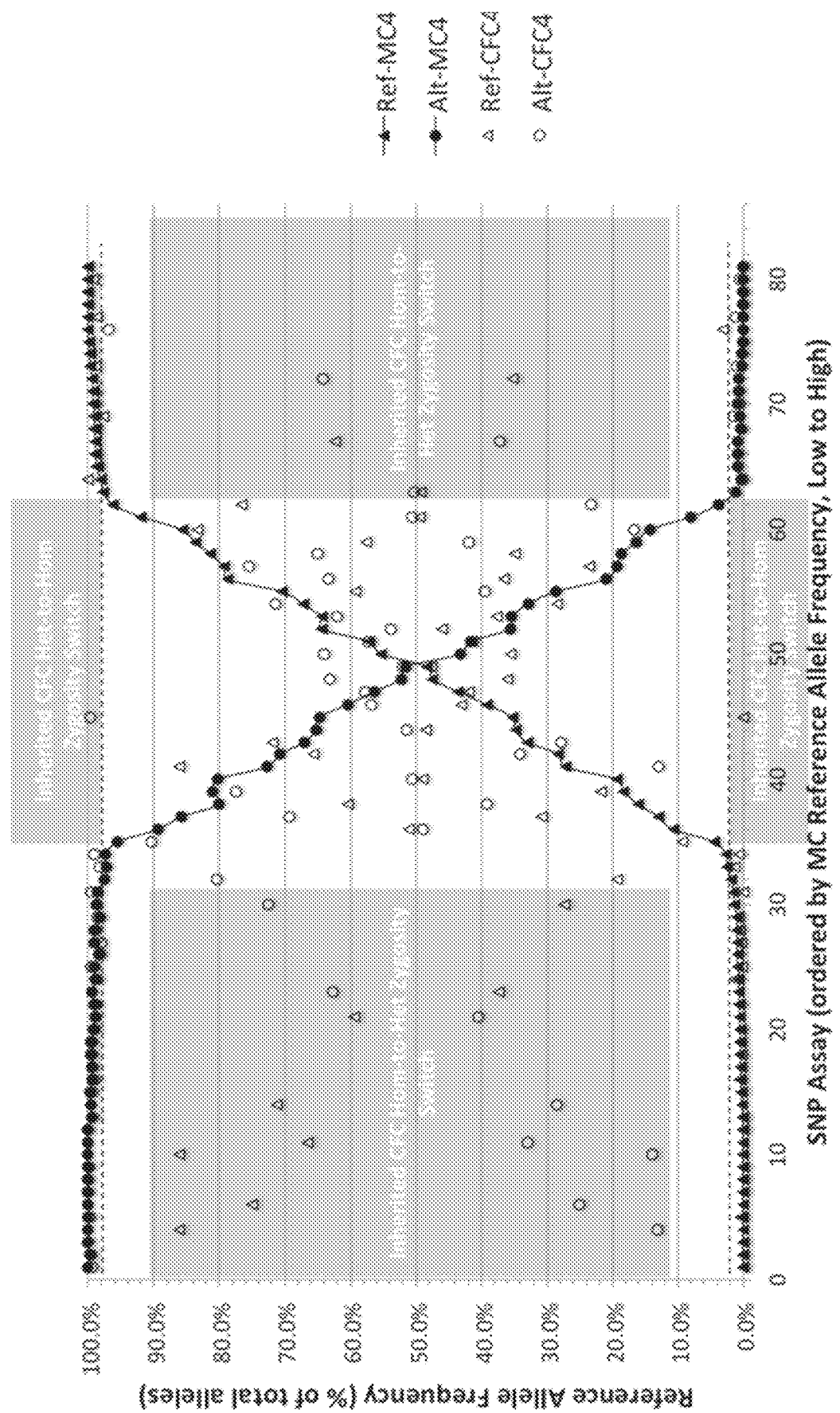

The data in FIGS. 20 and 21 show genotyping of two separate MC and CFC pairs of samples (MC1 & CFC1, and MC4 & CFC4), with each pair derived from blood sample from a different pregnancy. Both data sets showed similar magnitudes of difference between CFC and MC genotype, with zygosity differences at least 31% of the alleles assayed in the CFC1/MC1 pair analyzed in FIG. 20 and zygosity differences detected at least 17% of the alleles in the CFC4/MC4 pair analyzed in FIG. 21.

Figure 22:
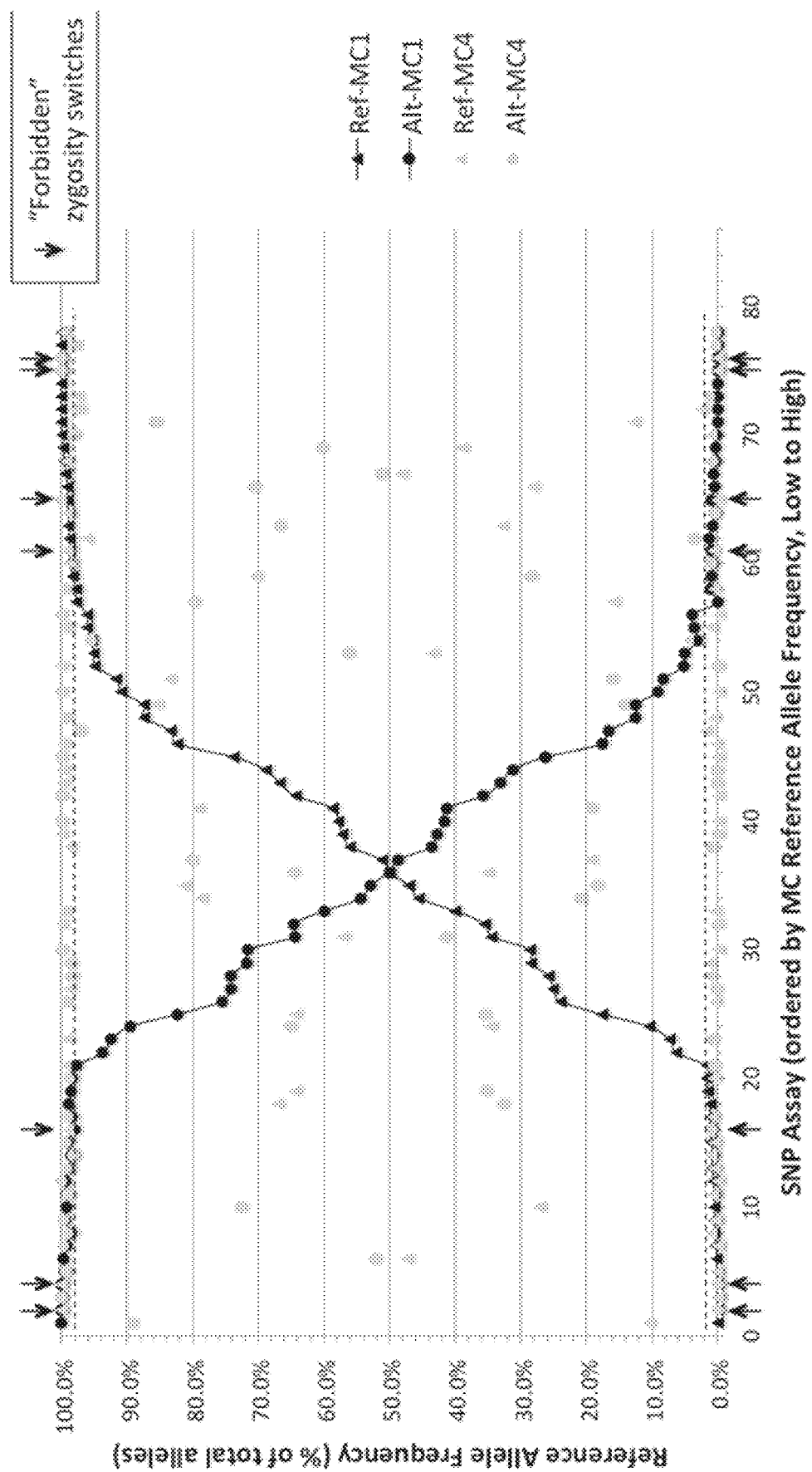

The data in FIG. 22 show the enhanced types of genotype difference that can be observed when comparing genotypes of unrelated individuals. In this comparison, genotypes of two genetically unrelated MC samples derived from two different pregnancies were analyzed. Unlike the case of the related CFC and MC genotypes obtained from cells isolated from a common pregnancy (FIGS. 20 and 21), the unrelated MC pools in FIG. 22 had no constraints on the allele ratios detected at any SNP locus. In particular, homozygous Reference/Reference genotypes can appear as homozygous Alternate/Alternate allele combinations in an unrelated individual, a transition (Ref/Ref to Alt/Alt) that would be "forbidden" by the normal process of genetic inheritance by descent (i.e., in which half of the mother's alleles and half of the father's alleles are combined to form the zygote). It is notable that 7 of these "forbidden" transitions (9% of the SNPs genotyped) were observed when comparing the unrelated individuals in FIG. 22 (a comparison of unrelated genomes where such transitions are allowed), while none of these "forbidden" transitions was observed in any of the CFC/MC comparisons we have done, including the fetal cell data shown in FIGS. 20 & 21. This lack of forbidden transitions is consistent with the fetal origin of CFC, cells derived from the maternal circulation, but genetically distinct from the mother.

Thus, as expected, the CFC pools isolated from maternal blood showed a genotype that was distinct from the MC, confirming that CFC was not maternal in origin. Additionally, transitions in allele composition that were "forbidden" by the process of normal Mendelian inheritance were not observed in any of the CFC/MC comparisons done to date, consistent with a fetal origin for CFC.

Example 14

Figure 23:
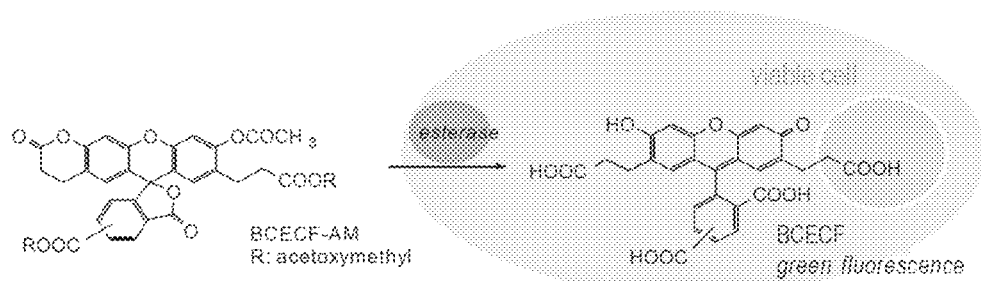
FIG. 23 shows a schematic view of a mechanism of action associated with an embodiment of the instant invention.

Certain embodiments of the present invention are generally directed to the identification of cancer tissue. In the present example, intracellular pH sensitive fluorescent dye is added to early human embryonic cells and normal adult human blood cells, and the fluorescent signal corresponding to the dye internalized in cells cytoplasm with more basic pH was used for detection of early embryonic/target cells. FIG. 23 shows a schematic view of an uncharged dye molecule adapted to enter a cell and be converted by a cell-specific esterase into a form that is identifiable and unable to leave the cell. This example shows that it is possible to use embryonic cells as a model of target cells based on the fact that in early stages of embryonic development cells of embryo exhibited predominance of glycolysis, as a major way of metabolizing glucose, something akin to cancer cell behavior. The predominance of glycolysis as energy source may generally be accompanied by alkalization of intracellular pH (pHi). For fetal development, glycolysis dependence is a transitional stage which gives way to oxidative phosphorylation predominance in later stage organogenesis. And for cancer tissue reliance on glycolysis is a hallmark of biological behavior, apparently irrespective of malignant phenotype.

In an area of performed surgery, normal cells and tissues may be exposed to an influence of acidic extracellular tumor environment that may lead to a relative predominance of apoptotic processes in the normal tissue located near to malignant tumor as well as further acidification of pHi of normal cells and tissues in the surgical margins. This fact makes fluorescent signal very low in normal cells located in the margin between tumor and healthy tissue. At the same time, pHi of malignant cells and tissue remains high and as such, an uncharged molecule having no fluorescence may be made charged in such cells, wherein the charged moiety has a known fluorescence behavior. Treating the margin region with appropriate electromagnetic radiation causes the cancer cells alone to "light up" due to their unique pH profile and associated charged fluorophore.

In this example, 3.5 ml of whole blood was collected from pregnant women, with pregnancy status confirmed by HCG testing, and additionally age of gestation was calculates by ultrasound, following consent by an Institutional Review Board approved study at a clinical site (Planned Parenthood of Southern New England, New Haven, Conn.). Blood was processed within 36 hours of collection and examined by a BD FACSARIA II SORP cell sorting machine, following incubation with a fluorescent dye (BCECF AM). The blood sample was kept in +4° C. after collection and before processing.

1 mg of BCECF AM (Invitrogen) was dissolved in 1 ml of DMSO and 10 aliquots were prepared. 1 aliquot was dissolved in 10 ml of Hank's Balanced Salt Solution in order to make working concentration (0.016 mM). A working solution of BCECF AM was added to sample (2 ml of BCECF AM to 2 ml of the sample) and incubated in room temperature for 45 minutes in the dark.

Lysis of RBC then was performed after staining by fluorescent dye (BCECF AM) by adding to the sample 16 ml of distillate water for 30 seconds in RT. Then PBS was added up to 50 ml total volume, followed by centrifugation (800 rpm for 10 min) and removal of the supernatant.

2 ml of sample was introduced for analysis by a cell sorter (BD FACSARIA II SORP) and data analyzed by the system software. Fetal/embryonic cells (with high green fluorescence) were further sorted and isolated on the Poly-L-Lysine microscopic glass slide and after air drying for 15 minutes slides were fixed in 4% Paraformaldehyde for 10 minutes. Then the slides were washed in PBS three times, 3 minutes each washing step. Maternal cells (with low green fluorescence) were sorted on a different Poly-L-Lysine slide and underwent same processing. Then both slides were stained by standard DAPI protocol.

Figures 24A, 24B:
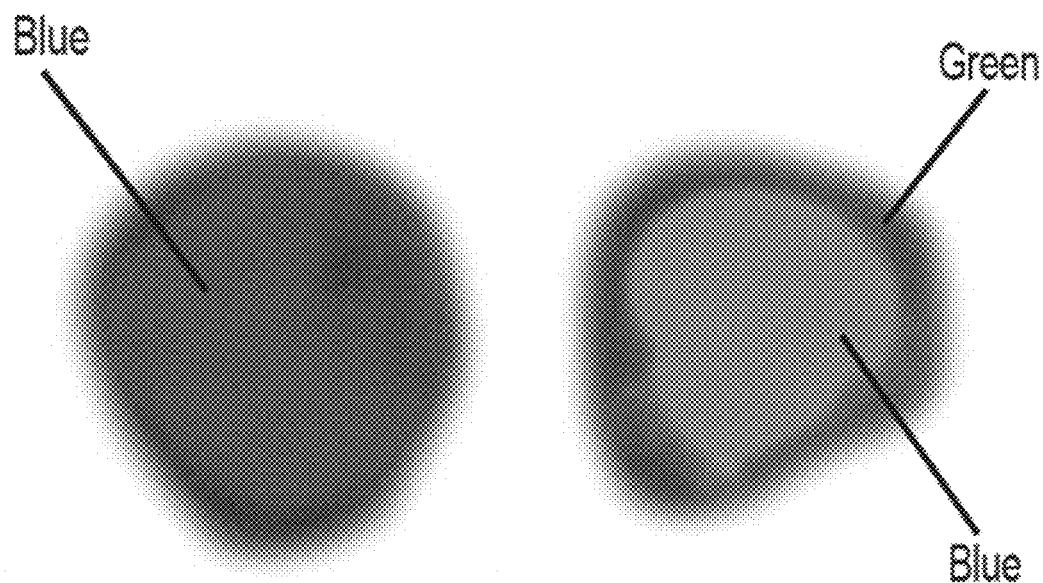
FIGS. 24A-24B show results from an example based on an embodiment of the instant invention.

The results demonstrates a normal blood cell with almost no green cytoplasmic fluorescence corresponding to acid pHi (FIG. 24A); and an embryonic cell with strong green florescence of cytoplasm, corresponding to an alkaline pHi (FIG. 24B). It is believed that cancer cells vs. healthy cells in human tissues would show similar differential outcomes.

Example 15

This example demonstrates experiments in which embryonic stem cells in peripheral maternal blood with totipotent properties were identified and isolated. Totipotent cells can form all the cell types in a body, as well as extra-embryonic, or placental, cells. These isolated unmodified cells can also be expanded in culture to allow physiological or genetic analysis of the cells, or the totipotent cells can be expanded and modified in culture to adapt them for therapeutic or other applications. The identification and isolation takes advantage of the characteristic of these cells to maintain a more basic intracellular pH than is observed in the surrounding media or in other blood cells using the methods of the present invention.

In this example, an intracellular pH sensitive fluorescent dye was added to samples of the peripheral blood of pregnant women. The fluorescent signal corresponding to the dye internalized in blood cells was significantly higher for cells with more basic intracellular pH. This signal was used for detection, counting, and separation in a flow cytometer using a FACS system. The isolated cells in this example were placed into cell culture in media designed to maintain human embryonic stem cells, and the growth, inter-cellular interaction and structure formation and the differentiation of these cultured cells was characterized using microscopic characterization of multicellular structures.

2 ml of whole blood was collected from women, with pregnancy status confirmed by HCG testing and gestational age established by ultrasound examination. The collection of samples was after consent. One de-identified sample was marked 147. The gestational age of the pregnancy of this subject was 7 weeks, 2 days. The blood was processed within 36 hours of collection and the blood was examined and sorted using a BD FACSARIA II SORP cell sorting machine following incubation with a fluorescent dye (BCECF AM) and lysis of red blood cells according to the method of the present invention. The sample was kept at 4° C. after collection and before processing.

For staining of cells, 1 mg of BCECF AM (Invitrogen) was dissolved in 1 ml of DMSO and 10 aliquots were prepared. 2 aliquots were dissolved in 10 ml of Hank's Balanced Salt Solution in order to make a working solution (0.016 mM). The working solution of BCECF AM was added to blood samples (2 ml of BCECF AM to 2 ml of sample) and incubated in room temperature for 40 minutes in the dark.

Lysis of RBCs then was performed after staining by fluorescent dye (BCECF AM) by adding to the sample 16 ml of distilled water for 30 seconds at room temperature. After this short incubation, PBS was added up to 50 ml total volume, followed by centrifugation (800 rpm for 10 min) to collect the pelleted unlysed cells and to remove the lysed cells and supernatant.

The stained sample was then introduced for analysis and sorting by a cell sorter (BD FACSARIA II SORP) and cytometry data analyzed by the system software. Embryonic stem cells were identified and sorted according their high intracellular pH status and sorted into single wells of 6 well Matrigel plates intended for Embryonic Stem Cell Culture (Corning). Each well was preloaded with 3 ml of TeSR-E8 medium (Stemcell Technologies) equilibrated to the room temperature prior to cell addition. After cell addition, the plate was placed in a $CO_2$ incubator (37° C., 5% $CO_2$), and the medium was replaced every 24 hours with fresh medium. Pictures of blastocyst-like structure in culture were taken by digital camera connected to an inverted microscope. After 5 days of culture, the medium was removed and the plate was stained using an H&E protocol. The stained cells and colonies on the plate were examined under bright visible wavelength Kohler illumination on a microscope (Olympus BX51) and pictures were taken by using an Olympus DP73 digital camera to capture images of the cells and structures formed during culture.

Figure 25A:
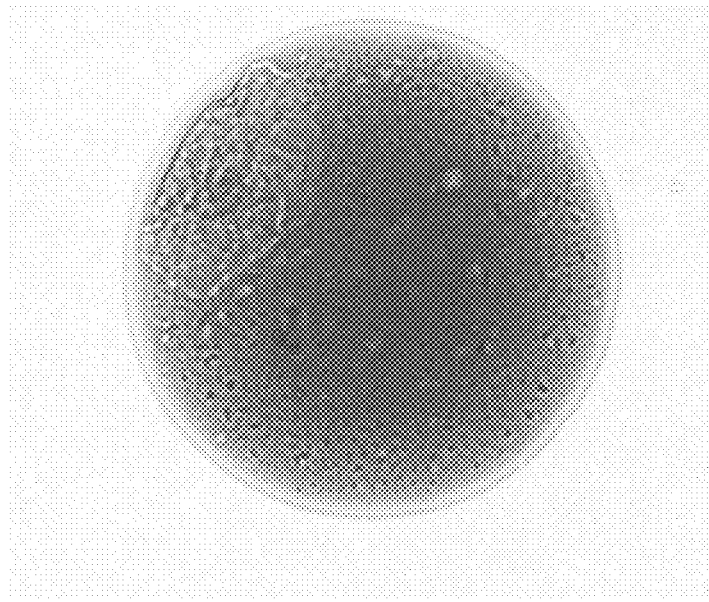
FIGS. 25A-25B shows an example in which cells isolated in accordance with an embodiment of the instant invention can be cultured in vitro.
Figure 25B:
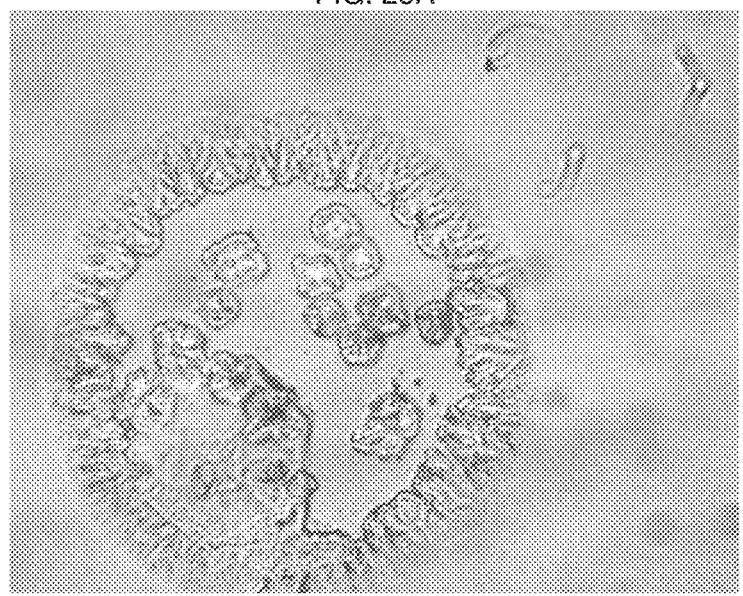

FIGS. 25A & 25B show that isolated cells could be cultured in vitro and shown to undergo morphogenesis to form complex structures resembling morula and blastocyst structures of early human embryogenesis. FIG. 25A (light microscopy, H&E) and FIG. 25B (inverted microscope) each show blastocyst-like structures formed from the cells. Multicellular structures formed in culture resembled blastocyst-like structures corresponding to the hollow sphere of cells comprising the developing trophoectodermal extra-embryonic membrane, and the asymmetrically placed cluster of cells of the inner cell mass.

Example 16

This example demonstrates that fetal/embryonic pluripotent stem cells in peripheral mother blood could be identified and isolated, and these cells then grown and characterized in cell culture to establish their expression of pluripotential stem cell markers. The identification and isolation of these cells exploited the preferential maintenance of a more alkaline intracellular pH by the stem cells of interest than that observed in the surrounding media or in other blood cells.

In this example, an intracellular pH sensitive fluorescent dye was added to peripheral blood of pregnant women, and the fluorescent signal corresponding to the dye internalized in cells was significantly higher for cells with more basic pH. This signal was then used for detection, counting, and separation in a flow cytometer using a FACS system. The isolated cells were placed into cell culture for 2-5 days in media designed to maintain human embryonic stem cells. After plating, growth, inter-cellular interaction and structure formation, the expression of markers of the pluripotential stages of stem cell differentiation was characterized in the cultured cells using microscopic imaging of multicellular structures and immunofluorescent detection of markers for pluripotent cells.

2 ml of whole blood was collected from women, with pregnancy status confirmed by HCG testing and gestational age established by ultrasound examination. The collection of samples was after consent. One de-identified sample was marked 147. The gestational age of the pregnancy in this subject was 7 weeks, 2 days. The blood was processed within 36 hours of collection and the blood was examined and sorted using a BD FACSARIA II SORP cell sorting machine following incubation with a fluorescent dye (BCECF AM) and lysis of red blood cells. The sample was kept in 4° C. after collection and before processing.

For the staining of cells, 1 mg of BCECF AM (Invitrogen) was dissolved in 1 ml of DMSO and 10 aliquots were prepared. 2 aliquots were dissolved in 10 ml of Hank's Balanced Salt Solution to make a working solution (0.016 mM). The working solution of BCECF AM was added to blood samples (2 ml of BCECF AM to 2 ml of sample) and incubated in room temperature for 40 minutes in the dark.

Lysis of RBCs was performed after staining by fluorescent dye (BCECF AM) by adding to the sample 16 ml of distilled water for 30 seconds at room temperature. After this short incubation, PBS was added up to 50 ml total volume, followed by centrifugation (800 rpm for 10 min) to collect the pelleted unlysed cells and to remove the lysed cells and supernatant.

The stained sample was then introduced for analysis and sorting by a cell sorter (BD FACSARIA II SORP) and cytometry data analyzed by the system software. Embryonic stem cells were identified and sorted according their high intracellular pH status and sorted into single wells of 6 well Matrigel plates intended for Embryonic Stem Cell Culture (Corning). Each well was preloaded with 3 ml of TeSR-E8 medium (Stemcell Technologies) equilibrated to the room temperature prior to cell addition. After cell addition, the plate was placed in a $CO_2$ incubator (37° C., 5% $CO_2$), and the medium was replaced every 24 hours with fresh medium.

After 5 days of culture, the medium was removed and the plate was stained by a PSC 4-Marker Immunocytochemistry Kit (Molecular Probes) according to the manufacturer's instructions. The colonies were examined under a microscope (Olympus BX51) and pictures were taken by using an Olympus DP73 digital camera for fluorescent microscopy to capture images of the cells and structures formed during culture.

Figure 26A:
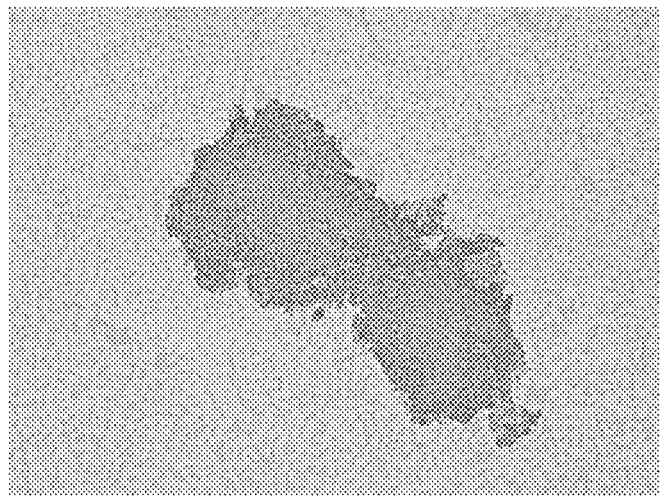
FIGS. 26A-26B shows an example in which cells isolated in accordance with an embodiment of the instant invention can be cultured in vitro.
Figure 26B:
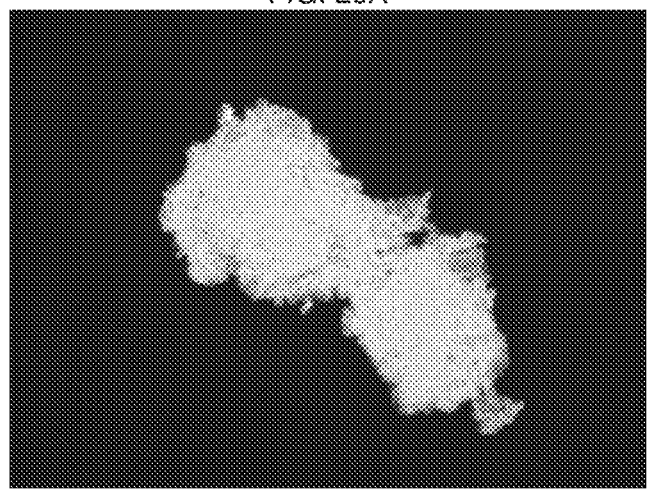

FIGS. 26A-26B show that the isolated cells were cultured in vitro and shown to express immunologically detected protein markers of pluripotent stem cells.

Figure 27A:
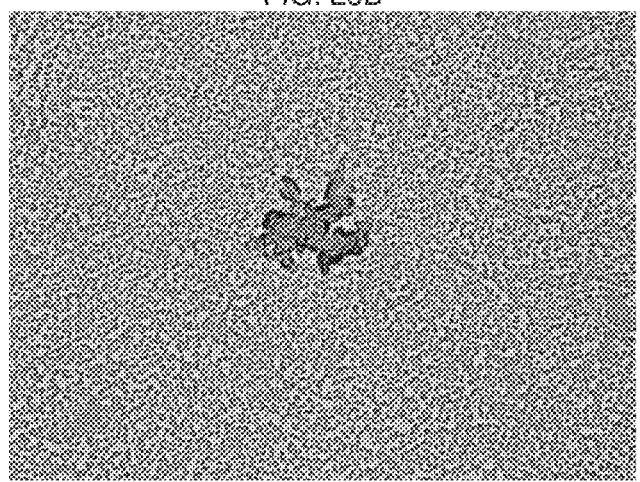
FIGS. 27A-27B shows an example in which cells isolated in accordance with an embodiment of the instant invention can be cultured in vitro.
Figure 27B:
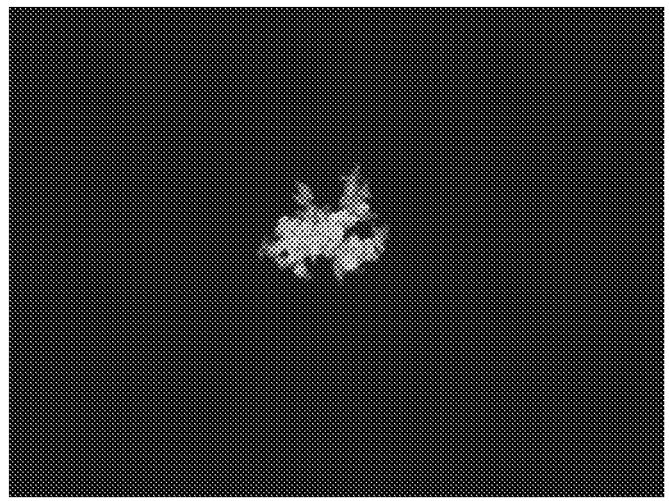

These figures show colony formation (visible wavelength light microscopy, FIG. 26A), and immunofluorescence detection of pluripotential marker expression (fluorescence microscopy, FIG. 26B. FIGS. 27A and 27B show another example of colony formation (visible wavelength light microscopy, FIG. 27A), and immunofluorescence detection of the expression of a different set of pluripotential markers (FIG. 27B). Thus, these cells have been shown to express other immunologically-detected protein markers of pluripotent stem cells.

Example 17

This example demonstrates that fetal/embryonic pluripotent stem cells in peripheral mother blood could be identified and isolated, and that these cells could then be grown and allowed to differentiate in cell culture to establish their later expression of markers of germ layer differentiation and their decreased expression of pluripotent stem cell markers. The identification and isolation of these cells exploited the preferential maintenance of a more alkaline intracellular pH by the stem cells of interest than that observed in the surrounding media or in other blood cells.

In this example, an intracellular pH sensitive fluorescent dye was added to peripheral blood of pregnant women, and the fluorescent signal corresponding to the dye internalized in cells was significantly higher for cells with more basic pH. This signal was then used for detection, counting, and separation in a flow cytometer using a FACS system. The isolated cells in this example were further placed into cell culture for 3 to 10 days in media designed to maintain human embryonic stem cells. After plating, the growth, inter-cellular interaction and structure formation, and the expression of markers of germ layer differentiation and markers of pluripotential stages of stem cell differentiation were then characterized in these cultured cells and in multicellular structures using microscopic imaging of morphology and immunofluorescent detection of marker epitopes.

2 ml of whole blood was collected from pregnant women, with pregnancy status confirmed by HCG testing and gestational age established by ultrasound examination. The collection of samples was after consent. The gestational age of the pregnancy in one subject was 7 weeks 2 days. The blood was processed within 36 hours of collection and the blood was examined and sorted using a BD FACSARIA II SORP cell sorting machine following incubation with a fluorescent dye (BCECF AM) and lysis of red blood cells. The sample was kept at 4° C. after collection and before processing.

For staining of cells, 1 mg of BCECF AM (Invitrogen) was dissolved in 1 ml of DMSO and 10 aliquots were prepared. 2 aliquots were dissolved in 10 ml of Hank's Balanced Salt Solution in order to make a working solution (0.016 mM). The working solution of BCECF AM was added to the blood samples (2 ml of BCECF AM to 2 ml of sample) and incubated in room temperature for 40 minutes in the dark.

Lysis of RBCs then was performed after staining by fluorescent dye (BCECF AM) by adding to the sample 16 ml of distilled water for 30 seconds at room temperature. After this incubation, PBS was added up to 50 ml total volume, followed by centrifugation (800 rpm for 10 min) to collect the pelleted unlysed cells and to remove the lysed cells and supernatant.

The stained sample was then introduced for analysis and sorting by a cell sorter (BD FACSARIA II SORP) and cytometry data analyzed by the system software. Embryonic stem cells were identified and sorted according their high intracellular pH status and sorted into single wells of 6 well Matrigel plates intended for Embryonic Stem Cell Culture. Each well was preloaded with 3 ml of TeSR-E8 medium (Stemcell Technologies) equilibrated to the room temperature prior to cell addition. After cell addition, the plate was placed into a $CO_2$ incubator (37° C., 5% $CO_2$), and the medium was replaced every 24 hours with fresh medium. After 5 days of culture, the medium was removed and the plate was stained by a 3-Germ Layer Immunocytochemistry Kit (Molecular Probes) according to the manufacturer's instructions. The colonies were examined under a microscope (Olympus BX51) and pictures were taken by using an Olympus DP73 digital camera for fluorescent microscopy.

Figure 28:
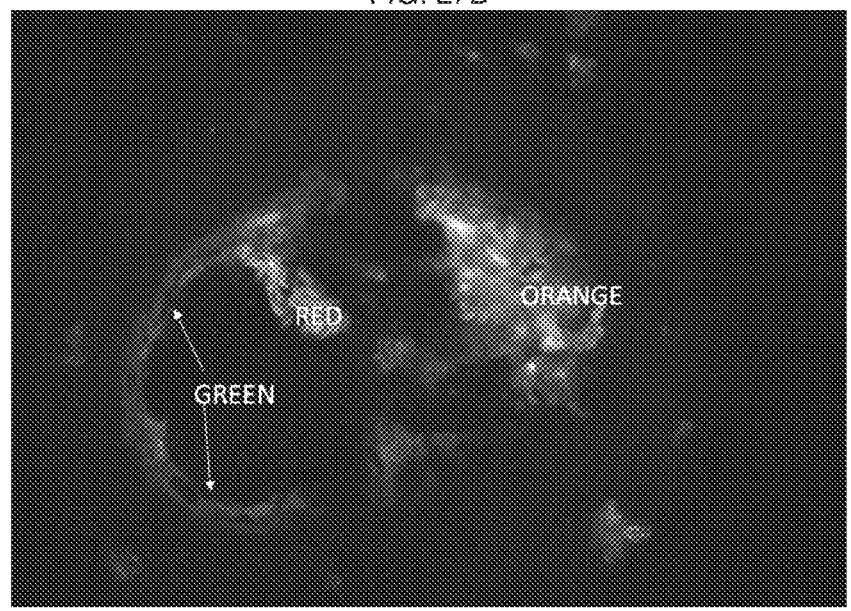
FIG. 28 shows an additional example in which cells isolated in accordance with an embodiment of the instant invention can be cultured in vitro.

FIG. 28 shows germ layer epitope expression in multicellular structured tissues in culture. Immunodetection of the expression of the TUJ1, AFP and SMA epitopes are used as markers for the three germ layers, with expression of the different markers indicated by the green, red, and orange colors in the micrograph. The cells were able to differentiate to express immunologically-detected protein markers of the three germ layers formed early in human embryogenesis.

Example 18

This example shows that totipotent stem cells could be identified and isolated from the freshly collected peripheral blood of a non-pregnant adult, and that these cells could be grown and allowed to differentiate in cell culture in order to establish complex tissue morphology similar to that observed during normal human development. Formation of these complex tissue morphologies was also accompanied by the progressive changes in the expression of markers of cell pluripotentiality, germ layer differentiation and more mature tissue differentiation. The identification and isolation of these cells exploited the preferential maintenance of a more alkaline intracellular pH by the stem cells of interest than that observed in the surrounding media or in other blood cells.

In this example, an intracellular pH sensitive fluorescent dye was added to peripheral blood of pregnant women, and the fluorescent signal corresponding to the dye that is internalized in cells is significantly higher for cells with more basic pH. This signal was then used for detection, counting, and separation in a flow cytometer using a FACS system. The isolated cells in this example were further placed into cell culture for 3 to 10 days in media designed to maintain human embryonic stem cells. After plating, the growth, inter-cellular interaction and structure formation, and the expression of markers of germ layer differentiation and markers of pluripotential stages of stem cell differentiation were then characterized in these cultured cells and in multicellular structures using microscopic imaging of morphology and immunofluorescent detection of marker epitopes.

2 ml of whole blood was collected from healthy adult volunteer. The blood was processed within 1 hour of collection and the blood was examined and sorted using a BD FACSARIA II SORP cell sorting machine following incubation with a fluorescent dye (BCECF AM) and lysis of red blood cells according to the method of the present invention. The sample was kept at 4° C. after collection and before processing.

For staining of cells, 1 mg of BCECF AM (Invitrogen) was dissolved in 1 ml of DMSO and 10 aliquots were prepared. 2 aliquots were dissolved in 10 ml of Hank's Balanced Salt Solution in order to make a working solution (0.016 mM). The working solution was added to blood samples (2 ml of BCECF AM to 2 ml of sample) and incubated in room temperature for 40 minutes in the dark.

Lysis of RBCs then was performed after staining by fluorescent dye (BCECF AM) by adding to the sample 16 ml of distilled water for 30 seconds at room temperature. After this short incubation, PBS was added up to 50 ml total volume, followed by centrifugation (800 rpm for 10 min) to collect the pelleted unlysed cells and to remove the lysed cells and supernatant.

The stained sample was introduced for analysis and sorting by a cell sorter (BD FACSARIA II SORP) and cytometry data analyzed by the system software. Adult stem cells were identified and sorted according their high intracellular pH status and sorted into single wells of 6 well Matrigel plates intended for Embryonic Stem Cell Culture (Corning). Each well was preloaded with 3 ml of TeSR-E8 medium (Stemcell Technologies) equilibrated to the room temperature prior to cell addition. After cell addition, the plate was placed in a $CO_2$ incubator (37° C., 5% $CO_2$), and the medium replaced every 24 hours with fresh medium. After 5 days of culture, the medium was removed and the plate was stained using an H&E protocol. The stained cells and colonies on the plate were examined under bright visible wavelength Kohler illumination on a microscope (Olympus BX51) and pictures were taken by using an Olympus DP73 digital camera to capture images of the cells and structures formed during culture.

Figure 29:
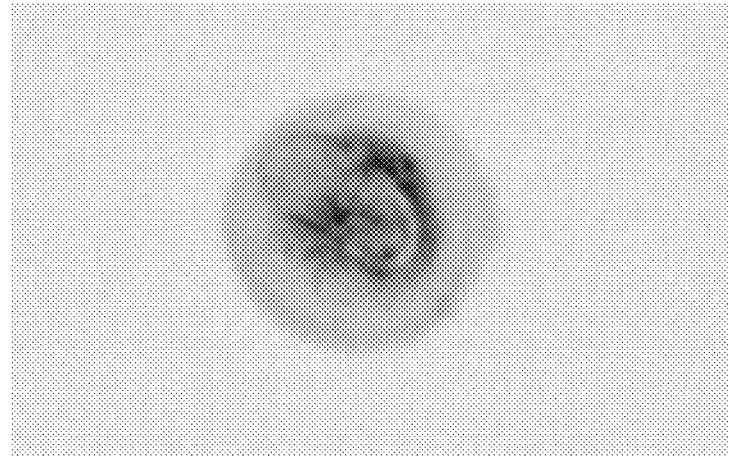
FIG. 29 shows an additional example in which cells isolated in accordance with an embodiment of the instant invention can be cultured in vitro.

FIG. 29 shows formation of complex multicellular structured tissues during culture of stem cell populations isolated from non-pregnant adult blood. The image illustrates one example of H&E stained multicellular structure comprised of central complex embryo-like tissue morphology encapsulated by a more uniform sphere of cells. The cells were able to undergo morphogenesis to form complex layered and tubular structures characteristic of tissue structures formed early in human embryogenesis.

Example 19

This example demonstrates that fetal/embryonic stem cells in peripheral mother blood can be identified and isolated, and these cells can be grown in cell culture and inoculated into nude mice for successful teratoma formation. The identification and isolation of these cells exploited the preferential maintenance of a more alkaline intracellular pH by the stem cells of interest than that observed in the surrounding media or in other blood cells using the methods of the present invention.

In this example, an intracellular pH sensitive fluorescent dye was added to the peripheral blood of pregnant women, and a fluorescent signal corresponding to the dye internalized in the cells was observed to be significantly higher for cells with more basic intracellular pH. This signal was used for detection, counting, and separation in a flow cytometer using a FACS system. The isolated cells in this example were further placed into cell culture for 2-5 days in media designed to maintain human embryonic stem cells, then frozen in liquid nitrogen and regrown in cell culture for additional several days, and inoculated subcutaneously to nude mice. After allowing the teratomas to grow to about 5 mm in diameter, these tumors were resected and stained by FISH using probes for the human X and Y chromosome.

2 ml of whole blood was collected from each of several pregnant women, with pregnancy status confirmed by HCG testing and gestational age established by ultrasound examination. The collection of samples was after consent. One de-identified sample was marked 149. The gestational age of the pregnancy in this subject was 5 weeks, 5 days. Blood was processed within 36 hours of collection and the blood was examined and sorted using a BD FACSARIA II SORP cell sorting machine following incubation with a fluorescent dye (BCECF AM) and lysis of red blood cells. The sample was kept at 4° C. after collection and before processing.

For staining of cells, 1 mg of BCECF AM (Invitrogen) was dissolved in 1 ml of DMSO and 10 aliquots were prepared. 1 aliquot was dissolved in 10 ml of Hank's Balanced Salt Solution at a working solution (0.016 mM). The working solution of BCECF AM was added to blood samples (2 ml of BCECF AM to 2 ml of sample) and incubated in room temperature for 40 minutes in the dark.

Lysis of RBCs was performed after staining by fluorescent dye (BCECF AM) by adding to the sample 16 ml of distilled water for 30 seconds at room temperature. After this short incubation, PBS was added up to 50 ml total volume, followed by centrifugation (800 rpm for 10 min) to collect the pelleted unlysed cells and to remove the lysed cells and supernatant.

The stained sample was introduced for analysis and sorting by a cell sorter (BD FACSARIA II SORP) and cytometry data analyzed by the system software. Embryonic stem cells were identified and sorted according their high intracellular pH status and sorted into single wells of 6 well Matrigel plates intended for Embryonic Stem Cell Culture (Corning). Each well was preloaded with 3 ml of TeSR-E8 medium (Stemcell Technologies) equilibrated to the room temperature prior to cell addition. After cell addition, the plate was placed in a $CO_2$ incubator (37° C., 5% $CO_2$), and the medium replaced every 24 hours with fresh medium. After 5 days, the cells were detached from the plastic using an enzyme-free protocol by pipetting and scraping. The cells were centrifuged at 300 g for 5 minutes at room temperature. The aspirate was removed, and the cells were resuspend in cold (2-8° C.) CryoStor CS10 solution (Stemcell Technologies). The cells were kept at −20° C. for 2 hours and then storage in liquid nitrogen for 3 weeks.

The cryo-vial containing the cells was thawed in a 37° C. water bath, and the cells placed into Matrigel plates (Corning 354671) preloaded with 3 ml of TeSR-E8 medium (StemCell Technologies) equilibrated to the room temperature prior to cell addition. The plate was placed in a $CO_2$ incubator (37° C., 5% $CO_2$) and the medium was replaced every 24 hours with fresh medium. The cells were detached from the plastic using an enzyme-free protocol by pipetting and scraping. The cells were centrifuged at 300 g for 5 minutes at room temperature. The aspirate was removed and cells were resuspend in 1 ml of fresh TeSR-E8 medium.

The cell suspension were transferred to a lab where subcutaneous inoculation of three nude mice was performed. After formation of subcutaneous tumors about 5 mm in diameter, the mice were sacrificed and the tumors resected. The tumors were formalin fixation and embedded in paraffin imbedding in 4 micron sections. The slides underwent DNA FISH staining (AneuVysion Multicolor DNA probe Kit, Abbott) for Y and X human chromosomes and H&E staining.

Figure 30:
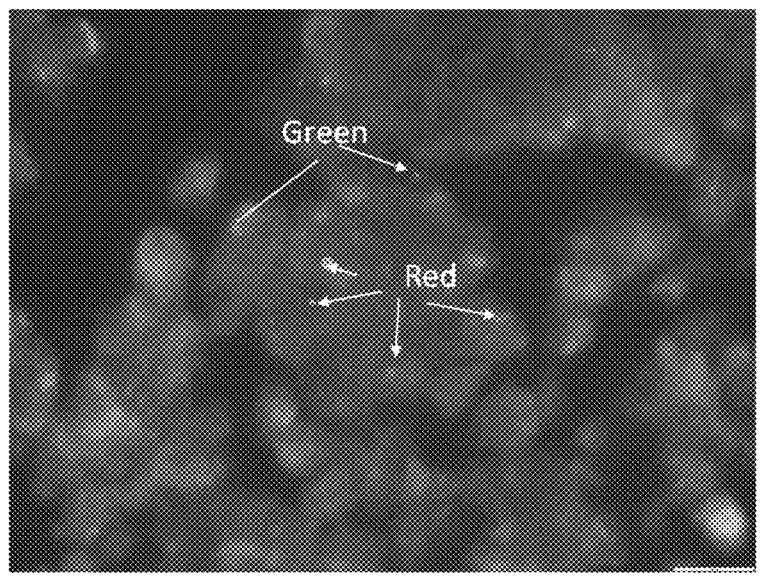
FIG. 30 shows FISH hybridization of X and Y chromosome probes to cells within a teratoma formed from a CFC isolated in accordance with an embodiment of the instant invention.

FISH analysis showed multiple positive X and Y FISH signals in all three subcutaneous tumors, and there was an absence of FISH signals in the remaining mice skin tissue present in the same slides. FIG. 30 shows FISH hybridization of Y (red) and X (green) chromosome probes in male tumors that have been passaged in culture and then transplanted into a immunocompromised mouse host where they implanted and grew to form a teratoma. The implanted male tumor cells were differentiated from the female host mouse cells by their ability to punctate hybridization to human Y chromosome specific FISH probes against the background of female mouse cells which did not specifically bind these probes.

Figure 31:
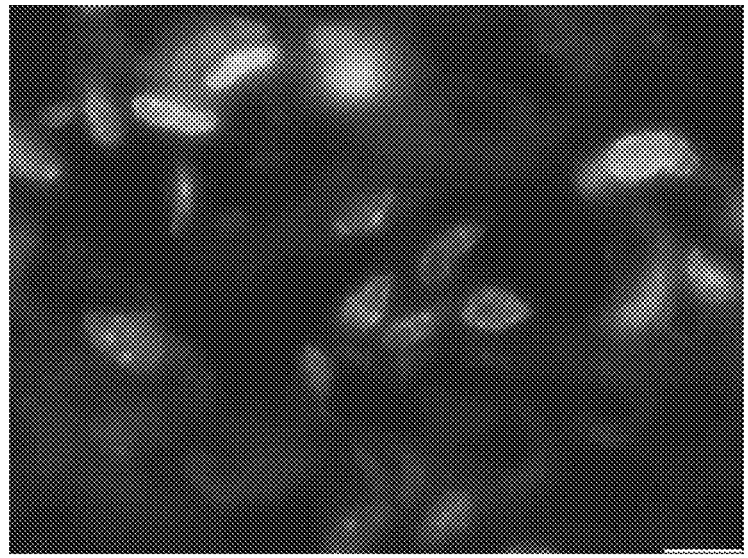
FIG. 31 shows FISH hybridization to cells at the margin of the CFC teratoma in an immunocompromised mouse host, in another embodiment of the invention.
Figure 32:
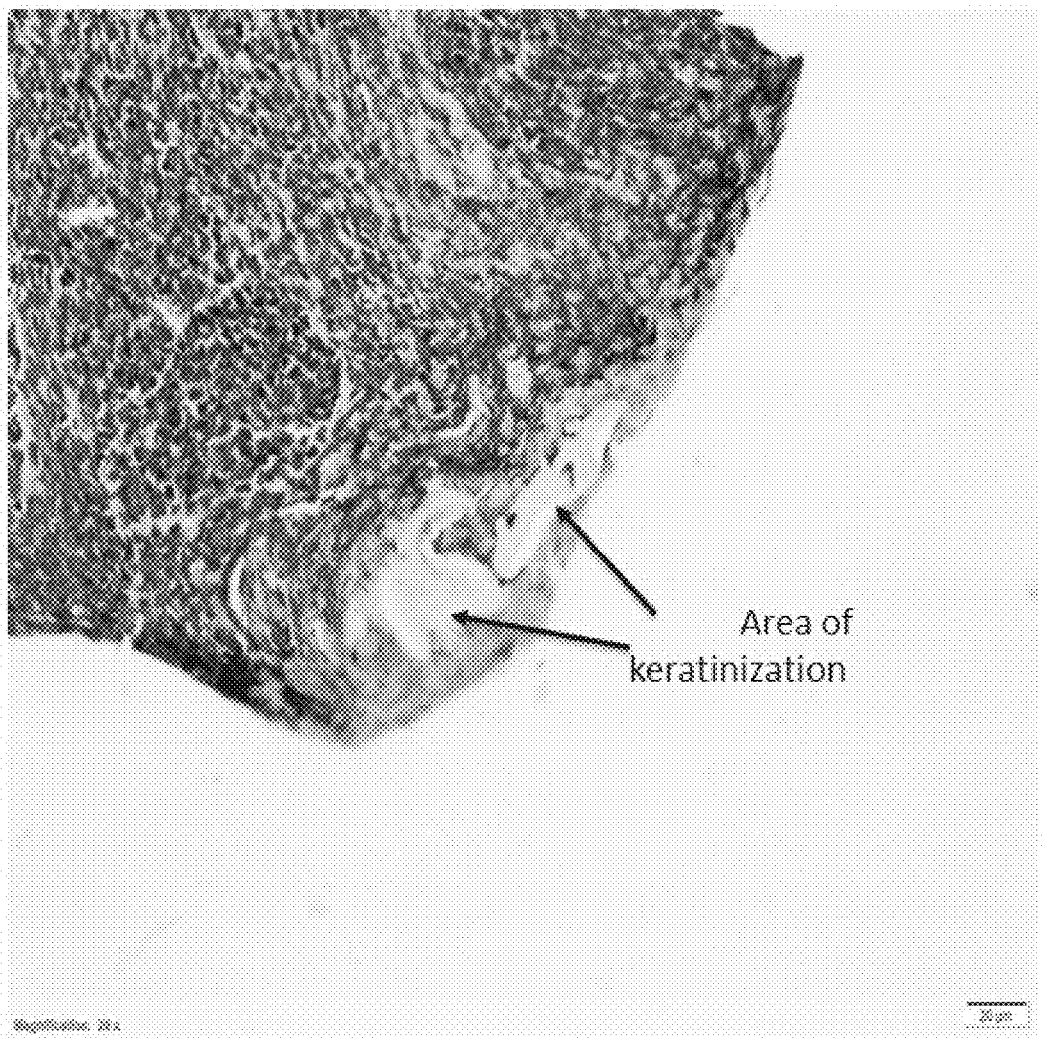
FIG. 32 shows H&E staining of a section of a teratoma formed from CFC isolated in accordance with an embodiment of the instant invention.

The tumor cells used in these xenotransplantation experiments were FACS sorted for high BCECF fluorescence from blood samples of pregnant women in early pregnancy. After isolation from the pregnant human donor, these cells were expanded in cell culture, successfully cryopreserved, thawed and replated in culture, and these cells formed tumors in immunocompromised animals when implanted in these hosts. FIG. 31 shows a region just at the margin of the teratoma that was primarily comprised of skin tissue of the female mouse host, showing no punctate human FISH signal in its nuclei. FIG. 32 shows an hematoxylin and eosin (H&E) stained section of the margin of the teratoma, and keratinized tissue indicative of differentiation of the teratoma can be seen. Such teratoma growth and differentiation is a unique property of pluripotent stem cells implanted and grown in vivo in an immunocompromised or autologous host. This ability of the CFC isolated to form differentiating teratomas in immunocompromized hosts supports the pluripotent stem cell nature of the isolated CFC.

This example specifically demonstrates that Y (red) and X (green) chromosomes shown as positive by DNA FISH (from male fetus) fetal stem cells could be separated by a FACS sorter from the blood samples of pregnant women in early pregnancy. These cells could be expanded in cell culture, successfully cryopreserved and thawed, and these cells retained the ability to form tumors in immunocompromised animals.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. In addition, as used herein the term "about" refers to +/−10%. In addition, when the word "about" is used herein in reference to a number, it should be understood that still another embodiment of the invention includes that number not modified by the presence of the word "about."

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

It is appreciated that certain features, which are, for clarity, described in the context of separate embodiments, may also be provided in combination in a single embodiment. Conversely, various features, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. For example, certain embodiments may include design features that allow for easy attachment and removal of an electrical device to and from a case.

All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of determining stem cells in a biological fluid arising from a subject, the method comprising:
    exposing a biological fluid arising from a subject to a pH-sensitive entity, wherein the biological fluid is suspected of containing stem cells, and wherein the pH-sensitive entity is more fluorescent or less fluorescent in the stem cells relative to non-stem cells in the biological fluid;
    determining the pH-sensitive entity internally within at least some of the cells within the biological fluid by determining fluorescence of the cells;
    isolating cells based on the determination of the fluorescence of the cells; and
    confirming that at least some of the isolated cells are stem cells arising from the subject.

2. The method of claim 1, further comprising confirming the identity of the stem cells.

3. The method of claim 1, wherein the stem cells are fetal stem cells, cord blood stem cells, embryonic stem cells, adult stem cells, tissue-specific stem cells, or induced pluripotent stem cells.

4. The method of claim 1, wherein the biological fluid is blood, cervical fluid, vaginal fluid, cerebral spinal fluid, urine, nipple aspirate, sputum, pleural or abdominal exudate or transudate.

5. The method of claim 1, wherein the fluid arises from a homogenized tissue sample.

6. The method of claim 1, wherein the fluid comprises a cell fraction.

7. The method of claim 1, further comprising acidifying the biological fluid.

8. The method of claim 1, further comprising counting the stem cells.

9. The method of claim 1, wherein the pH-sensitive entity comprises one or more of 2',7'-bis(2-carboxyethyl)-5(6)-carboxyfluorescein tetrakis(acetoxymethyl) ester (BCECF AM), 5(6)-carboxy-2',7'-dichlorofluorescein, 5(6)-carboxyfluorescein, 5(6)-carboxyfluorescein diacetate, 5(6)-carboxyfluorescein N-hydroxysuccinimide ester, 3,6-diacetoxyphthalonitrile, 6,8-dihydroxy-1,3-pyrenedisulfonic acid disodium salt, Eosin diacetate, or naphthofluorescein.

10. The method of claim 1, wherein the pH-sensitive entity is fluorescent at a pH of greater than about 7.5 and substantially less fluorescent at a pH of less than about 7.

11. The method of claim 1, comprising isolating at least some of the cells using a fluorescent microscope.

12. The method of claim 1, further comprising determining genotype of the stem cells.

13. The method of claim 1, further comprising culturing the stem cells.

14. The method of claim 1, further comprising performing genetic analysis of the stem cells.

15. The method of claim 14, wherein said genetic analysis includes searching for genetic abnormalities.

16. The method of claim 1, comprising sequencing DNA from the stem cells.

17. The method of claim 1, further comprising performing morphology analysis and/or cytopathology analysis of the stem cells.

18. The method of claim 1, further comprising determining gene expression of the stem cells.

19. The method of claim 1, further comprising determining a metabolic profile of the stem cells.

\* \* \* \* \*